(12) United States Patent
Hölder et al.

(10) Patent No.: US 7,776,864 B2
(45) Date of Patent: Aug. 17, 2010

(54) FUSED BICYCLIC PYRIMIDINES

(75) Inventors: Swen Hölder, London (GB); Matthias Vennemann, Constance (DE); Gerrit Beneke, Allensbach (DE); Armin Zülch, Schriesheim (DE); Volker Gekeler, Constance (DE); Thomas Beckers, Constance (DE); Astrid Zimmermann, Constance (DE); Hemant Joshi, Navi Mumbai (IN)

(73) Assignee: Bayer Schering Pharma AG, Berlin (DE)

( * ) Notice: Subject to any disclaimer, the term of this patent is extended or adjusted under 35 U.S.C. 154(b) by 0 days.

(21) Appl. No.: 12/191,703

(22) Filed: Aug. 14, 2008

(65) Prior Publication Data

US 2009/0137607 A1 May 28, 2009

(30) Foreign Application Priority Data

Aug. 14, 2007 (IN) .................. 1572/MUM/2007
Oct. 18, 2007 (EP) .................. 07118736

(51) Int. Cl.
| | |
|---|---|
| A61K 31/4965 | (2006.01) |
| A61K 31/505 | (2006.01) |
| A61K 31/519 | (2006.01) |
| A61K 31/445 | (2006.01) |
| C07D 471/04 | (2006.01) |
| C07D 471/22 | (2006.01) |
| C07D 487/00 | (2006.01) |
| C07D 491/00 | (2006.01) |
| C07D 403/00 | (2006.01) |
| C07D 239/02 | (2006.01) |
| A01N 43/54 | (2006.01) |
| A01N 43/90 | (2006.01) |
| A01N 43/40 | (2006.01) |

(52) U.S. Cl. ............... 514/255.05; 514/257; 514/259.1; 514/259.31; 514/259.3; 514/269; 514/273; 514/322; 544/247; 544/263; 544/281; 544/295; 544/330

(58) Field of Classification Search ............ 514/255.05, 514/257, 259.1, 259.3, 259.31, 269, 273, 514/322; 544/247, 263, 281, 295, 322, 330
See application file for complete search history.

(56) References Cited

FOREIGN PATENT DOCUMENTS

| WO | 2006036395 A | 4/2006 |
|---|---|---|
| WO | 2006071819 A | 7/2006 |
| WO | PCTEP2008060690 R | 1/2009 |

*Primary Examiner*—Sreeni Padmanabhan
*Assistant Examiner*—Sarah Pihonak
(74) *Attorney, Agent, or Firm*—MIllen, White, Zelano & Branigan, P.C.

(57) ABSTRACT

Compounds of formula (I)

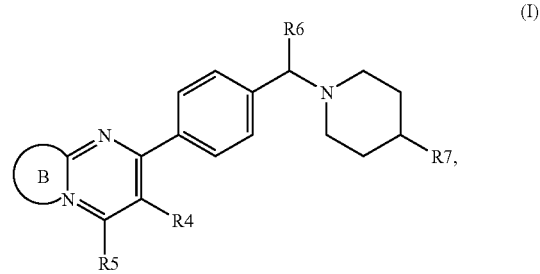

a tautomer or stereoisomer thereof, or a salt thereof, wherein ring B and the pyrimidine to which it is fused, R4, R5, R6 and R7 have the meanings as given in the description and the claims, are effective inhibitors of the Pi3K/Akt pathway.

20 Claims, No Drawings

FUSED BICYCLIC PYRIMIDINES

FIELD OF APPLICATION OF THE INVENTION

The invention relates to fused pyrimidine compounds, which are used in the pharmaceutical industry for the manufacture of pharmaceutical compositions.

KNOWN TECHNICAL BACKGROUND

Cancer is the second most prevalent cause of death in the United States, causing 450,000 deaths per year. While substantial progress has been made in identifying some of the likely environmental and hereditary causes of cancer, there is a need for additional therapeutic modalities that target cancer and related diseases. In particular there is a need for therapeutic methods for treating diseases associated with dysregulated growth/proliferation.

Cancer is a complex disease arising after a selection process for cells with acquired functional capabilities like enhanced survival/resistance towards apoptosis and a limitless proliferative potential. Thus, it is preferred to develop drugs for cancer therapy addressing distinct features of established tumors.

One pathway that has been shown to mediate important survival signals for mammalian cells comprises receptor tyrosine kinases like platelet-derived growth factor receptor (PDGF-R), human epidermal growth factor 2/3 receptor (HER2/3), or the insulin-like growth factor 1 receptor (IGF-1R). After activation the respectives by ligand, these receptors activate the phoshatidylinositol 3-kinase (Pi3K)/Akt pathway. The phoshatidylinositol 3-kinase (Pi3K)/Akt protein kinase pathway is central to the control of cell growth, proliferation and survival, driving progression of tumors. Therefore within the class of serine-threonine specific signalling kinases, Akt (protein kinase B; PKB) with the isoenzmyes Akt1 (PKBα), Akt2 (PKB β) and Akt3 (PKB γ) is of high interest for therapeutic intervention. Akt is mainly activated in a Pi3-kinase dependent manner and the activation is regulated through the tumor suppressor PTEN (phosphatase and tensin homolog), which works essentially as the functional antagonist of Pi3K.

The Pi3K/Akt pathway regulates fundamental cellular functions (e.g. transcription, translation, growth and survival), and is implicated in human diseases including diabetes and cancer. The pathway is frequently overactivated in a wide range of tumor entities like breast and prostate carcinomas. Upregulation can be due to overexpression or constitutively activation of receptor tyrosine kinases (e.g. EGFR, HER2/3), which are upstream and involved in its direct activation, or gain- or loss-of-function mutants of some of the components like loss of PTEN. The pathway is targeted by genomic alterations including mutation, amplification and rearrangement more frequently than any other pathway in human cancer, with the possible exception of the p53 and retinoblastoma pathways. The alterations of the Pi3K/Akt pathway trigger a cascade of biological events, that drive tumor progression, survival, angiogenesis and metastasis.

Activation of Akt kinases promotes increased nutrient uptake, converting cells to a glucose-dependent metabolism that redirects lipid precursors and amino acids to anabolic processes that support cell growth and proliferation. These metabolic phenotype with overactivated Akt lead to malignancies that display a metabolic conversion to aerobic glycolysis (the Warburg effect). In that respect the Pi3K/Akt pathway is discussed to be central for survival despite unfavourable growth conditions such as glucose depletion or hypoxia.

A further aspect of the activated PI3K/Akt pathway is to protect cells from programmed cell death ("apoptosis") and is hence considered to transduce a survival signal. By acting as a modulator of anti-apoptotic signalling in tumor cells, the Pi3K/Akt pathway, particular Akt itself is a target for cancer therapy. Activated Akt phosphorylates and regulates several targets, e.g. BAD, GSK3 or FKHRL1, that affect different signalling pathways like cell survival, protein synthesis or cell movement. This Pi3K/Akt pathway also plays a major part in resistance of tumor cells to conventional anti-cancer therapies. Blocking the Pi3K/Akt pathway could therefore simultaneously inhibit the proliferation of tumor cells (e.g. via the inhibition of the metabolic effect) and sensitize towards pro-apoptotic agents.

Akt inhibition selectively sensitized tumor cells to apoptotic stimuli like Trail, Campthothecin and Doxorubicin. Dependent on the genetic background/molecular apperations of tumors, Akt inhibitors might induce apoptotic cell death in monotherapy as well.

In the International patent application WO200202563 substituted triazolopyrimidines are disclosed for the treatment of cancer. In the International patent applications WO2004096131, WO2005100344, WO2006036395, WO2006065601, WO2006091395 and WO2006135627 Akt inhibitors are described.

DESCRIPTION OF THE INVENTION

It has now been found that the fused pyrimidine compounds, which are described in detail below, have surprising and advantageous properties.

In accordance with a first aspect, the invention relates to compounds of formula (I)

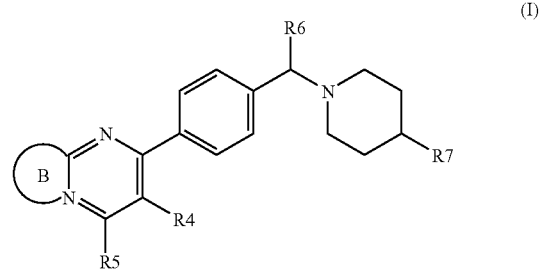

wherein ring B and the pyrimidine to which it is fused form a ring system selected from

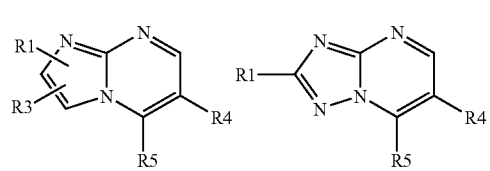

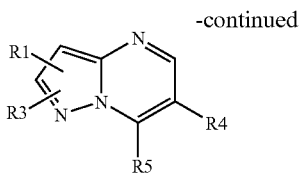

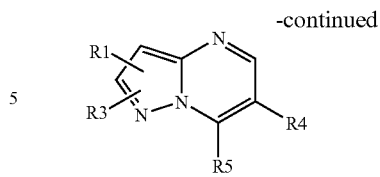

wherein
R1 is hydrogen, 1-4C-alkyl, halogen, amino, 1-4C-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl,
R2 is hydrogen or 1-4C-alkyl,
R3 is hydrogen, 1-4C-alkyl or halogen,
R4 is phenyl or thienyl,
R5 is hydrogen, 1-4C-alkoxy, amino, mono- or di-1-4C-alkylamino, 1-4C-alkyl or 3-7C-cycloalkyl,
R6 is hydrogen or 1-4C-alkyl,
R7 is —W—Y,
W is a monocyclic 5-membered heteroarylene comprising 1 nitrogen atom and optionally 1 or 2 further heteroatoms independently selected from oxygen, nitrogen and sulphur, and wherein the heteroarylene is optionally substituted by R8,
R8 is 1-4C-alkyl or 3-7C-cycloalkyl,
Y is phenyl or a monocyclic 5 or 6 membered heteroaryl comprising 1 nitrogen atom and optionally 1 or 2 further heteroatoms independently selected from oxygen, nitrogen, sulphur,
and wherein the heteroaryl is optionally substituted by R9,
R9 is 1-4C-alkyl, 1-4C-alkoxy or halogen, or a salt, particularly a pharmaceutically acceptable salt, a tautomer, or a stereoisomer of said compound, or a salt, particularly a pharmaceutically acceptable salt, of said tautomer or said stereoisomer.

In accordance with a second aspect, the invention relates to compounds of formula (I)

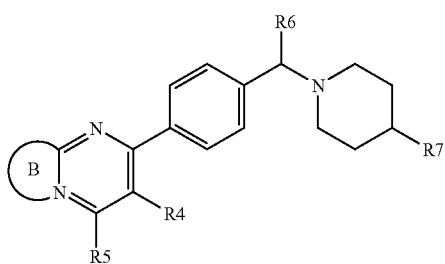

wherein ring B and the pyrimidine to which it is fused form a ring system selected from

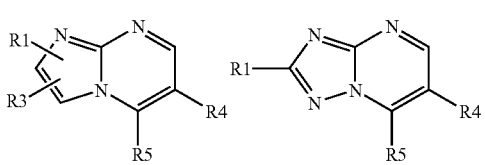

wherein
R1 is hydrogen, 1-4C-alkyl, halogen, amino, 1-4C-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl,
R2 is hydrogen or 1-4C-alkyl,
R3 is hydrogen, 1-4C-alkyl or halogen,
R4 is phenyl or thienyl,
R5 is hydrogen, 1-4C-alkoxy, amino, mono- or di-1-4C-alkylamino, 1-4C-alkyl or 3-7C-cycloalkyl,
R6 is hydrogen or 1-4C-alkyl,
R7 is —W—Y,
W is a monocyclic 5-membered heteroarylene comprising 1 nitrogen atom and optionally 1 or 2 further heteroatoms independently selected from oxygen, nitrogen and sulphur, and wherein the heteroarylene is optionally substituted by R8,
R8 is 1-4C-alkyl or 3-7C-cycloalkyl, Y is a monocyclic 5 or 6 membered heteroaryl comprising 1 nitrogen atom and optionally 1 or 2 further heteroatoms independently selected from oxygen, nitrogen and sulphur,
and wherein the heteroaryl is optionally substituted by R9,
R9 is 1-4C-alkyl, 1-4C-alkoxy or halogen, or a salt, particularly a pharmaceutically acceptable salt, a tautomer, or a stereoisomer of said compound, or a salt, particularly a pharmaceutically acceptable salt, of said tautomer or said stereoisomer.

1-4C-Alkyl is a straight-chain or branched alkyl group having 1 to 4 carbon atoms. Examples are methyl, ethyl, n-propyl, iso-propyl, n-butyl, iso-butyl, sec-butyl and tert-butyl.

Mono- or di-1-4C-alkylamino radicals contain in addition to the nitrogen atom, one or two of the abovementioned 1-4C-alkyl radicals. Examples are the methylamino, the ethylamino, the isopropylamino, the dimethylamino, the diethylamino and the diisopropylamino radical.

Mono- or di-1-4C-alkylaminocarbonyl radicals contain in addition to the carbonyl group one of the abovementioned mono- or di-1-4C-alkylamino radicals. Examples are the N-methylaminocarbonyl, the N,N-dimethylaminocarbonyl, the N-ethylaminocarbonyl, the N-propylaminocarbonyl, the N,N-diethylaminocarbonyl and the N-isopropylaminocarbonyl.

Halogen within the meaning of the present invention is iodine, or particularly bromine, chlorine and fluorine.

1-4C-Alkoxy represents radicals, which in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy, ethoxy and methoxy radicals.

3-7C-Cycloalkyl stands for cyclopropyl, cyclobutyl, cyclopentyl, cyclohexyl or cycloheptyl.

3-7C-Cycloalkyloxy stands for cyclopropyloxy, cyclobutyloxy, cyclopentyloxy, cyclohexyloxy or cycloheptyloxy.

2-4C-Alkenyl is a straight chain or branched alkenyl radical having 2 to 4 carbon atoms. Examples are the but-2-enyl, but-3-enyl (homoallyl), prop-1-enyl, prop-2-enyl (allyl) and the ethenyl (vinyl) radicals.

2-4C-Alkynyl is a straight chain or branched alkynyl radical having 2 to 4 carbon atoms. Examples are the but-2-ynyl, but-3-ynyl (homopropargyl), prop-1-ynyl, 1-methylprop-2-ynyl (1-methylpropargyl), prop-2-ynyl (propargyl) and the ethynyl radicals.

The term "monocyclic 5- or 6-membered heteroaryl" comprised without being restricted thereto, the 5-membered heteroaryl radicals furyl, thienyl, pyrrolyl, oxazolyl, isoxazolyl, thiazolyl, isothiazolyl, imidazolyl, pyrazolyl, triazolyl (1,2,4-triazolyl, 1,3,4-triazolyl or 1,2,3-triazolyl), thiadiazolyl (1,3,4-thiadiazolyl, 1,2,5-thiadiazolyl, 1,2,3-thiadiazolyl or 1,2,4-thiadiazolyl) and oxadiazolyl (1,3,4-oxadiazolyl, 1,2,5-oxadiazolyl, 1,2,3-oxadiazolyl or 1,2,4-oxadiazolyl), as well as the 6-membered heteroaryl radicals pyridinyl, pyrimidinyl, pyrazinyl and pyridazinyl. Preferred 5- or 6-membered heteroaryl radicals are furanyl, thiophenyl, pyrrolyl, thienyl, thiazolyl, oxazolyl, thiadiazolyl, oxadiazolyl, pyridinyl, pyrimidinyl, pyrimidinyl, pyrazinyl or pyridazinyl. More preferred 5- or 6-membered heteroaryl radicals are furan-2-yl, thiophen-2-yl, pyrrol-2-yl, thien-2-yl, thiazolyl, oxazolyl, 1,3,4-thiadiazolyl, 1,3,4-oxadiazolyl, pyridin-2-yl, pyridin-4-yl, pyrimidin-2-yl, pyrimidin-4-yl, pyrazin-2-yl or pyridazin-3-yl.

The term "monocyclic 5-membered heteroarylene" is a divalent radical in which arbitrary one hydrogen atom is eliminated from the above described "heteroaryl" and may include, without being restricted thereto, the 5-membered heteroaryl radicals furylene, thienylene, pyrrolylene, oxazolylene, isoxazolylene, thiazolylene, isothiazolylene, imidazolylene, pyrazolylene, triazolylene (1,2,4-triazolylene, 1,3,4-triazolylene or 1,2,3-triazolylene), thiadiazolylene (1,3,4-thiadiazolylene, 1,2,5-thiadiazolylene, 1,2,3-thiadiazolylene or 1,2,4-thiadiazolylene) and oxadiazolylene (1,3,4-oxadiazolylene, 1,2,5-oxadiazolylene, 1,2,3-oxadiazolylene or 1,2,4-oxadiazolylene). Preferred 5-membered heteroaryl radicals are triazolylene, pyrazolylene, oxadiazolylene or imidazolylene. More preferred 5-membered heteroaryl radicals are 1,2,4-triazolylene, pyrazolylene, 1,2,4-oxadiazolylene or imidazolylene.

In general and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

Constituents which are optionally substituted as stated herein, may be substituted, unless otherwise noted, at any possible position.

The heteroarylic or heteroarylenic groups mentioned herein may be substituted by their given substituents or parent molecular groups, unless otherwise noted, at any possible position, such as e.g. at any substitutable ring carbon or ring nitrogen atom.

Unless otherwise noted, rings containing quaternizable amino- or imino-type ring nitrogen atoms (—N═) may be preferably not quaternized on these amino- or imino-type ring nitrogen atoms by the mentioned substituents or parent molecular groups.

Unless otherwise noted, any heteroatom of a heteroarylic or heteroarylenic ring with unsatisfied valences mentioned herein is assumed to have the hydrogen atom(s) to satisfy the valences.

When any variable occurs more than one time in any constituent, each definition is independent.

In a preferred embodiment of the above-mentioned first or second aspect, the invention relates to compounds of formula (I), wherein ring B and the pyrimidine to which it is fused form a ring system selected from

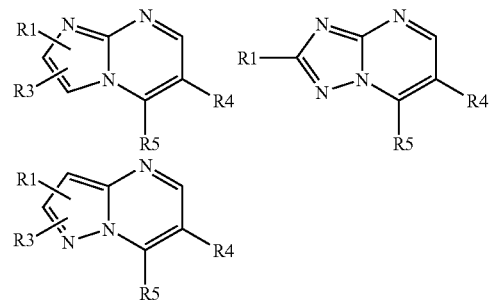

wherein

R1 is hydrogen, 1-4C-alkyl, halogen, amino, 1-4C-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl, R2 is hydrogen or 1-4C-alkyl, R3 is hydrogen, 1-4C-alkyl or halogen, R4 is phenyl or thienyl, R5 is hydrogen, 1-4C-alkoxy, amino, mono- or di-1-4C-alkylamino, 1-4C-alkyl or 3-7C-cycloalkyl, R6 is hydrogen or 1-4C-alkyl, R7 is —W—Y, W is a monocyclic 5-membered heteroarylene comprising 1 nitrogen atom and optionally 1 or 2 further heteroatoms independently selected from oxygen, nitrogen and sulphur, and wherein the heteroarylene is optionally substituted by R8, R8 is 1-4C-alkyl or 3-7C-cycloalkyl, Y is a monocyclic 5 or 6 membered heteroaryl comprising 1 nitrogen atom and optionally 1 or 2 further heteroatoms independently selected from oxygen, nitrogen, sulphur, and wherein the heteroaryl is optionally substituted by R9, R9 is 1-4C-alkyl or halogen, and the salts, as well as the stereoisomers and salts of the stereoisomers thereof.

In further embodiment the invention relates to compounds of formula (I), wherein ring B and the pyrimidine to which it is fused form a ring system selected from

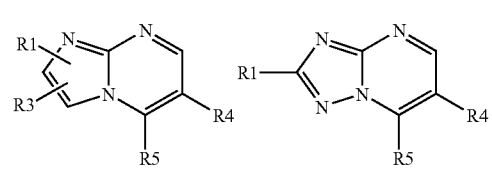

-continued

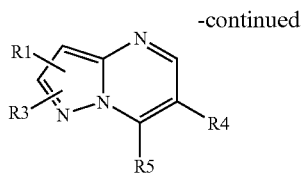

wherein
R1 is hydrogen, 1-4C-alkyl, halogen, amino, 1-4C-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl,
R2 is hydrogen or 1-4C-alkyl,
R3 is hydrogen, 1-4C-alkyl or halogen,
R4 is phenyl or thienyl,
R5 is hydrogen, 1-4C-alkoxy, amino, mono- or di-1-4C-alkylamino, 1-4C-alkyl or 3-7C-cycloalkyl,
R6 is hydrogen or 1-4-C-alkyl,
R7 is —W—Y,
W is a monocyclic 5-membered heteroarylene comprising 1 nitrogen atom and optionally 1 or 2 further heteroatoms independently selected from oxygen, nitrogen and sulphur, and wherein the heteroarylene is optionally substituted by R8,
R8 is 1-4C-alkyl or 3-7C-cycloalkyl,
Y is a monocyclic 5 or 6 membered heteroaryl comprising 1 nitrogen atom and optionally 1 or 2 further heteroatoms independently selected from oxygen, nitrogen, sulphur, and wherein the heteroaryl is optionally substituted by R9,
R9 is 1-4C-alkyl or halogen, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused form a ring system selected from

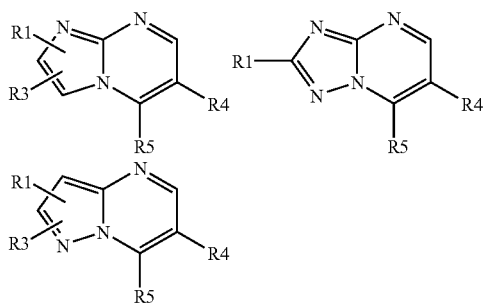

wherein
R1 is hydrogen, 1-4C-alkyl, halogen, amino, 1-4C-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl,
R2 is hydrogen or 1-4C-alkyl,
R3 is hydrogen,
R4 is phenyl or thienyl,
R5 is hydrogen, 1-4C-alkoxy, amino, mono- or di-1-4C-alkylamino, 1-4C-alkyl or 3-7C-cycloalkyl,
R6 is hydrogen or 1-4-C-alkyl,
R7 is —W—Y,
W is triazolylene, pyrazolylene or imidazolylene, each of which is optionally substituted by R8,
R8 is 1-4C-alkyl or 3-7C-cycloalkyl,
Y is thiazolyl, oxazolyl, thiadiazolyl, oxadiazolyl, pyridinyl, pyrimidinyl, pyrazinyl or pyridazinyl, each of which is optionally substituted by R9,
R9 is 1-4C alkyl or halogen, and the salts, as well as the stereoisomers and salts of the stereoisomers thereof.

In a further preferred embodiment of the above-mentioned first or second aspect, the invention relates to compounds of formula (I), wherein ring B and the pyrimidine to which it is fused form a ring system selected from

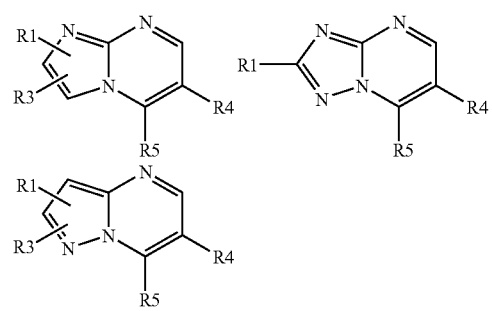

wherein
R1 is hydrogen, 1-4C-alkyl, halogen, amino, 1-4C-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl,
R2 is hydrogen or 1-4C-alkyl,
R3 is hydrogen,
R4 is phenyl or thienyl,
R5 is hydrogen, 1-4C-alkoxy, amino, mono- or di-1-4C-alkylamino, 1-4C-alkyl or 3-7C-cycloalkyl,
R6 is hydrogen or 1-4-C-alkyl,
R7 is —W—Y,
W is triazolylene, pyrazolylene or imidazolylene, each of which is optionally substituted by R8,
R8 is 1-4C-alkyl or 3-7C-cycloalkyl,
Y is thiazolyl, oxazolyl, thiadiazolyl, oxadiazolyl, pyridinyl, pyrimidinyl, pyrazinyl or pyridazinyl, each of which is optionally substituted by R9,
R9 is 1-4C alkyl or halogen, or a salt, particularly a pharmaceutically acceptable salt, a tautomer, or a stereoisomer of said compound, or a salt, particularly a pharmaceutically acceptable salt, of said tautomer or said stereoisomer.

In another embodiment the invention relates to compounds of formula (I), wherein ring B and the pyrimidine to which it is fused form a ring system selected from

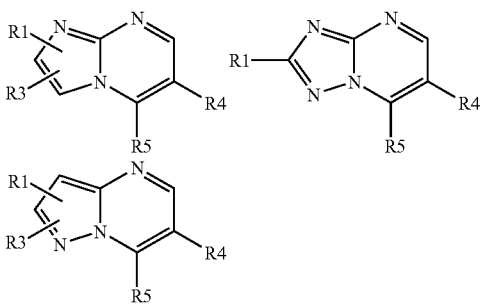

wherein
R1 is hydrogen, 1-4C-alkyl, halogen, amino, 1-4C-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl,
R2 is hydrogen or 1-4C-alkyl,
R3 is hydrogen,
R4 is phenyl,
R5 is hydrogen, 1-4C-alkoxy, amino, mono- or di-1-4C-alkylamino, 1-4C-alkyl or 3-7C-cycloalkyl,
R6 is hydrogen or methyl,
R7 is —W—Y,
W is 1,2,4-triazolylene, pyrazolylene or imidazolylene,
Y is thiazol-2-yl, thiazol-4-yl, oxazol-2-yl, oxazol-4-yl, 1,3,4-thiadiazol-2-yl, 1,3,4-oxadiazol-2-yl, pyridin-2-yl, pyrimidin-2-yl, pyrimidin-4-yl, pyrazin-2-yl or pyridazin-3-yl, and the salts, as well as the stereoisomers and salts of the stereoisomers thereof.

In another embodiment the invention relates to compounds of formula (I), wherein ring B and the pyrimidine to which it is fused form a ring system selected from

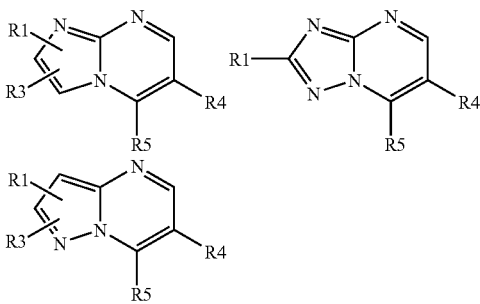

wherein
R1 is hydrogen, 1-4C-alkyl, halogen, amino, 1-4C-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl,
R2 is hydrogen or 1-4C-alkyl,
R3 is hydrogen,
R4 is phenyl,
R5 is hydrogen, 1-4C-alkoxy, amino, mono- or di-1-4C-alkylamino, 1-4C-alkyl or 3-7C-cycloalkyl,
R6 is hydrogen or methyl,
R7 is —W—Y,
W is 1,2,4-triazolylene, pyrazolylene or imidazolylene,
Y is thiazol-2-yl, thiazol-4-yl, oxazol-2-yl, oxazol-4-yl, 1,3,4-thiadiazol-2-yl, 1,3,4-oxadiazol-2-yl, pyridin-2-yl, pyrimidin-2-yl, pyrimidin-4-yl, pyrazin-2-yl or pyridazin-3-yl, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused form a ring system selected from

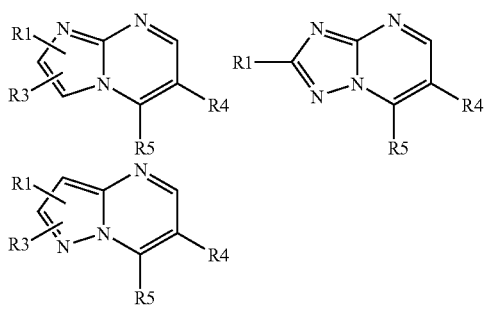

wherein
R1 is hydrogen, 1-4C-alkyl, halogen, cyano, 3-7C-cycloalkyl, 2-4C-alkenyl, 2-4C-alkynyl, —C(O)OR2 or trifluoromethyl,
R2 is 1-4C-alkyl,
R3 is hydrogen,
R4 is phenyl,
R5 is hydrogen, mono- or di-1-4C-alkylamino or 1-4C-alkyl,
R6 is hydrogen or methyl,
R7 is —W—Y,
W is 1,2,4-triazolylene, pyrazolylene or imidazolylene,
Y is pyridin-2-yl, pyrimidin-2-yl, pyrazin-2-yl, pyrimidin-4-yl or pyridazin-3-yl, and the salts, as well as the stereoisomers and salts of the stereoisomers thereof.

In a further preferred embodiment of the above-mentioned first or second aspect, the invention relates to compounds of formula (I), wherein ring B and the pyrimidine to which it is fused form a ring system selected from

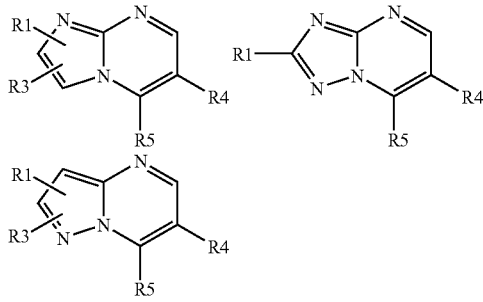

wherein
R1 is hydrogen, 1-4C-alkyl, halogen, cyano, 3-7C-cycloalkyl, 2-4C-alkenyl, 2-4C-alkynyl, —C(O)OR2 or trifluoromethyl,
R2 is 1-4C-alkyl,
R3 is hydrogen, R4 is phenyl,
R5 is hydrogen, mono- or di-1-4C-alkylamino or 1-4C-alkyl,
R6 is hydrogen or methyl,
R7 is —W—Y,
W is 1,2,4-triazolylene, pyrazolylene or imidazolylene,
Y is pyridin-2-yl, pyrimidin-2-yl, pyrazin-2-yl, pyrimidin-4-yl or pyridazin-3-yl, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused form a ring system selected from

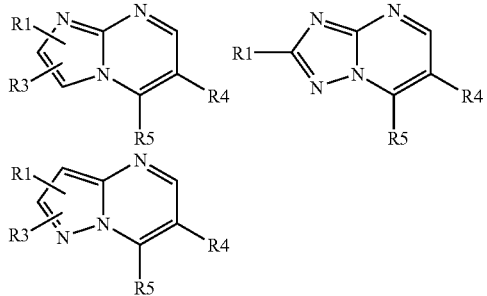

wherein
R1 is hydrogen, methyl, ethyl, halogen, cyclopropyl, cyclobutyl, —C≡CH or —CH═CH2,
R3 is hydrogen,
R4 is phenyl,
R5 is hydrogen or —NHMe,
R6 is hydrogen,
R7 is —W—Y,
W is 1,2,4-triazolylene,
Y is pyridin-2-yl or pyrimidin-2-yl, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused form a ring system selected from

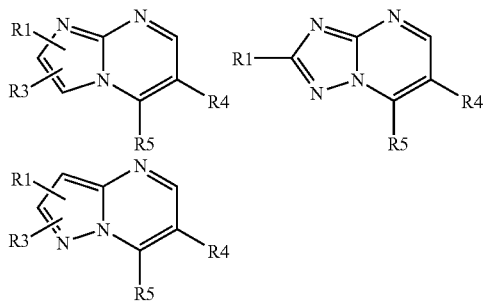

wherein
R1 is hydrogen, methyl, ethyl, halogen, cyclopropyl, cyclobutyl, —C≡CH or —CH═CH2,
R3 is hydrogen,
R4 is phenyl,
R5 is hydrogen or —NHMe,
R6 is hydrogen,
R7 is —W—Y,
W is 1,2,4-triazolylene,
Y is pyridin-2-yl or pyrimidin-2-yl, and the salts, as well as the stereoisomers and salts of the stereoisomers thereof.

In a further preferred embodiment of the above-mentioned first aspect, the invention relates to compounds of formula (I), wherein ring B and the pyrimidine to which it is fused form a ring system selected from

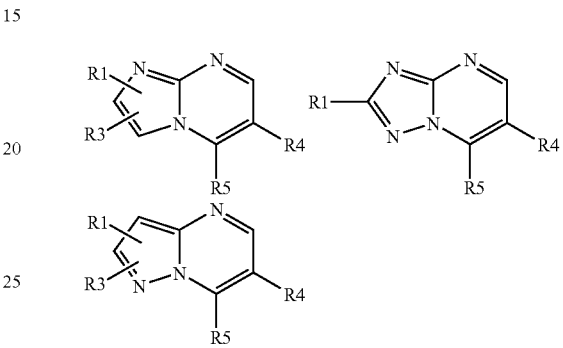

wherein
R1 is hydrogen, 1-4C-alkyl, halogen, amino, 1-4C-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl,
R2 is hydrogen or 1-4C-alkyl,
R3 is hydrogen,
R4 is phenyl or thienyl,
R5 is hydrogen, 1-4C-alkoxy, amino, mono- or di-1-4C-alkylamino, 1-4C-alkyl or 3-7C-cycloalkyl,
R6 is hydrogen or 1-4-C-alkyl,
R7 is —W—Y,
W is triazolylene, pyrazolylene or imidazolylene,
  each of which is optionally substituted by R8,
R8 is 1-4C-alkyl or 3-7C-cycloalkyl,
Y is pyrrolyl, furanyl, thienyl, thiazolyl, oxazolyl, thiadiazolyl, oxadiazolyl, pyridinyl, pyrimidinyl, pyrazinyl or pyridazinyl, each of which is optionally substituted by R9,
R9 is 1-4C-alkyl, 1-4C-alkoxy or halogen, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first aspect, the invention relates to compounds of formula (I), wherein ring B and the pyrimidine to which it is fused form a ring system selected from

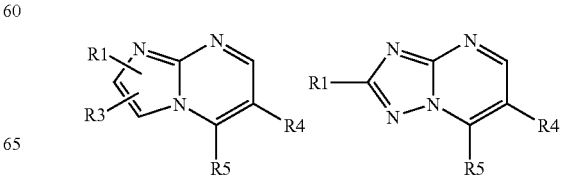

-continued

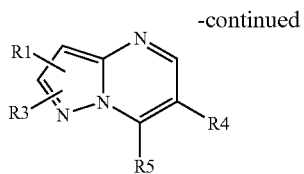

R1 is hydrogen, 1-4C-alkyl, halogen, amino, 1-4C-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl, R2 is hydrogen or 1-4C-alkyl, R3 is hydrogen, R4 is phenyl or thienyl, R5 is hydrogen, 1-4C-alkoxy, amino, mono- or di-1-4C-alkylamino, 1-4C-alkyl or 3-7C-cycloalkyl, R6 is hydrogen or methyl, R7 is —W—Y, W is 1,2,4-triazolylene, pyrazolylene or imidazolylene, Y is furan-2-yl, pyrrol-2-yl, thien-2-yl, thiazol-2-yl, thiazol-4-yl, oxazol-2-yl, oxazol-4-yl, 1,3,4-thiadiazol-2-yl, 1,3,4-oxadiazol-2-yl, pyridin-2-yl, pyridin-4-yl, pyrimidin-2-yl, pyrimidin-4-yl, pyrazin-2-yl or pyridazin-3-yl, each of which is optionally substituted by R9, R9 is 1-4C-alkyl, 1-4C-alkoxy or halogen, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first aspect, the invention relates to compounds of formula (I), wherein ring B and the pyrimidine to which it is fused form a ring system selected from

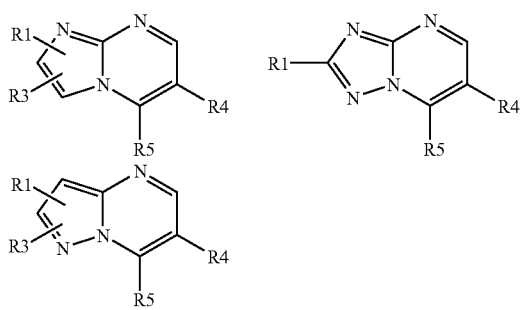

wherein

R1 is hydrogen, 1-4C-alkyl, halogen, amino, 1-4C-alkoxy, cyano, 3-7C-cycloalkyl, 2-4C-alkenyl, 2-4C-alkynyl, mono- or di-1-4C-alkylamino, —C(O)OR2 or trifluoromethyl, R2 is 1-4C-alkyl, R3 is hydrogen, R4 is phenyl or thienyl, R5 is hydrogen, 1-4C-alkoxy, mono- or di-1-4C-alkylamino or 1-4C-alkyl, R6 is hydrogen or methyl, R7 is —W—Y, W is 1,2,4-triazolylene, pyrazolylene or imidazolylene, Y is furan-2-yl, pyrrol-2-yl, pyridin-4-yl, thiazol-2-yl, thien-2-yl, pyridin-2-yl, pyrimidin-2-yl, pyrazin-2-yl, pyrimidin-4-yl or pyridazin-3-yl, each of which is optionally substituted by R9, R9 is 1-4C-alkyl, 1-4C-alkoxy or halogen, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned second aspect, the invention relates to compounds of formula (I), wherein ring B and the pyrimidine to which it is fused form a ring system selected from

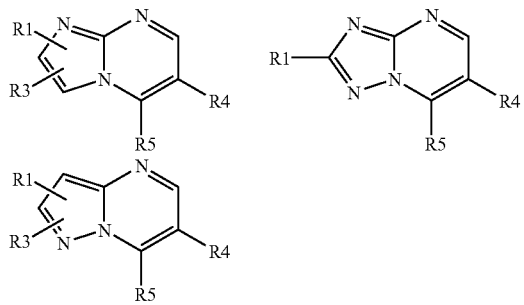

wherein

R1 is hydrogen, 1-4C-alkyl, halogen, amino, 1-4C-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl, R2 is hydrogen or 1-4C-alkyl, R3 is hydrogen, R4 is phenyl or thienyl, R5 is hydrogen, 1-4C-alkoxy, amino, mono- or di-1-4C-alkylamino, 1-4C-alkyl or 3-7C-cycloalkyl, R6 is hydrogen or 1-4-C-alkyl, R7 is —W—Y, W is triazolylene, pyrazolylene or imidazolylene, each of which is optionally substituted by R8, R8 is 1-4C-alkyl or 3-7C-cycloalkyl, Y is phenyl, pyrrolyl, furanyl, thienyl, thiazolyl, oxazolyl, thiadiazolyl, oxadiazolyl, pyridinyl, pyrimidinyl, pyrazinyl or pyridazinyl, each of which is optionally substituted by R9, R9 is 1-4C-alkyl, 1-4C-alkoxy or halogen, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned second aspect, the invention relates to compounds of formula (I), wherein ring B and the pyrimidine to which it is fused form a ring system selected from

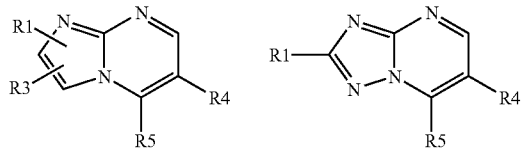

-continued

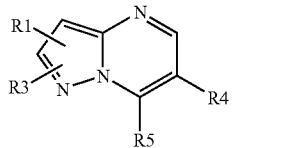

wherein
R1 is hydrogen, 1-4C-alkyl, halogen, amino, 1-4C-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl,
R2 is hydrogen or 1-4C-alkyl,
R3 is hydrogen,
R4 is phenyl or thienyl,
R5 is hydrogen, 1-4C-alkoxy, amino, mono- or di-1-4C-alkylamino, 1-4C-alkyl or 3-7C-cycloalkyl,
R6 is hydrogen or methyl,
R7 is —W—Y,
W is 1,2,4-triazolylene, pyrazolylene or imidazolylene,
Y is phenyl, furan-2-yl, pyrrol-2-yl, thien-2-yl, thiazol-2-yl, thiazol-4-yl, oxazol-2-yl, oxazol-4-yl, 1,3,4-thiadiazol-2-yl, 1,3,4-oxadiazol-2-yl, pyridin-2-yl, pyridin-4-yl, pyrimidin-2-yl, pyrimidin-4-yl, pyrazin-2-yl or pyridazin-3-yl, each of which is optionally substituted by R9,
R9 is 1-4C-alkyl, 1-4C-alkoxy or halogen, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned second aspect, the invention relates to compounds of formula (I), wherein ring B and the pyrimidine to which it is fused form a ring system selected from

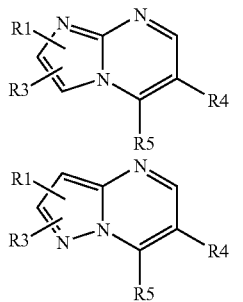

wherein
R1 is hydrogen, 1-4C-alkyl, halogen, amino, 1-4C-alkoxy, cyano, 3-7C-cycloalkyl, 2-4C-alkenyl, 2-4C-alkynyl, mono- or di-1-4C-alkylamino, —C(O)OR2 or trifluoromethyl,
R2 is 1-4C-alkyl,
R3 is hydrogen,
R4 is phenyl or thienyl,
R5 is hydrogen, 1-4C-alkoxy, mono- or di-1-4C-alkylamino or 1-4C-alkyl,
R6 is hydrogen or methyl,
R7 is —W—Y,
W is 1,2,4-triazolylene or pyrazolylene,
Y is phenyl, furan-2-yl, pyrrol-2-yl, pyridin-4-yl, thiazol-2-yl, pyridin-2-yl, pyrimidin-2-yl, pyrazin-2-yl, pyrimidin-4-yl or pyridazin-3-yl, each of which is optionally substituted by R9,
R9 is 1-4C-alkyl, 1-4C-alkoxy or halogen, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first aspect, the invention relates to compounds of formula (I), wherein ring B and the pyrimidine to which it is fused form a ring system selected from

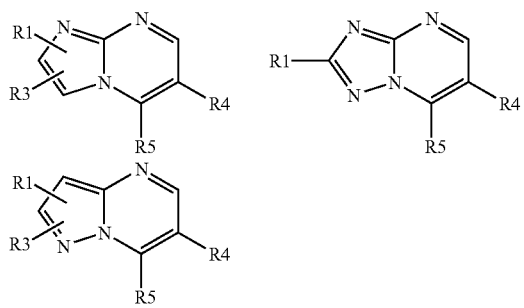

wherein
R1 is hydrogen, 1-4C-alkyl, halogen, amino, 1-4C-alkoxy, cyano, 3-7C-cycloalkyl, 2-4C-alkenyl, 2-4C-alkynyl, mono- or di-1-4C-alkylamino, —C(O)OR2 or trifluoromethyl,
R2 is 1-4C-alkyl,
R3 is hydrogen,
R4 is phenyl or thienyl,
R5 is hydrogen, 1-4C-alkoxy, mono- or di-1-4C-alkylamino or 1-4C-alkyl,
R6 is hydrogen,
R7 is —W—Y,
W is 1,2,4-triazolylene or pyrazolylene,
Y is phenyl, furan-2-yl, pyrrol-2-yl, thiazol-2-yl, pyridin-4-yl, pyridin-2-yl, pyrimidin-2-yl, pyrazin-2-yl, pyrimidin-4-yl or pyridazin-3-yl, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned second aspect, the invention relates to compounds of formula (I), wherein ring B and the pyrimidine to which it is fused form a ring system selected from

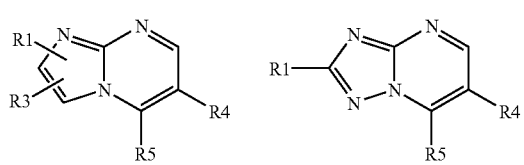

-continued

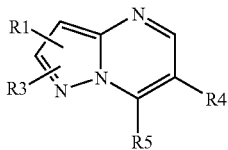

wherein
R1 is hydrogen, 1-4C-alkyl, halogen, amino, 1-4C-alkoxy, cyano, 3-7C-cycloalkyl, 2-4C-alkenyl, 2-4C-alkynyl, mono- or di-1-4C-alkylamino, —C(O)OR2 or trifluoromethyl,
R2 is 1-4C-alkyl,
R3 is hydrogen,
R4 is phenyl or thienyl,
R5 is hydrogen, 1-4C-alkoxy, mono- or di-1-4C-alkylamino or 1-4C-alkyl,
R6 is hydrogen,
R7 is —W—Y,
W is 1,2,4-triazolylene or pyrazolylene,
Y is furan-2-yl, pyrrol-2-yl, thiazol-2-yl, pyridin-4-yl, pyridin-2-yl, pyrimidin-2-yl, pyrazin-2-yl, pyrimidin-4-yl or pyridazin-3-yl, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused form a ring system selected from

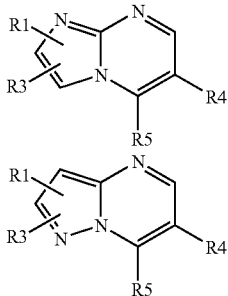 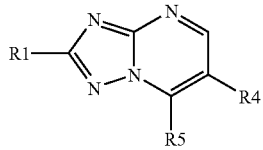

wherein
R1 is hydrogen, methyl, ethyl, isopropyl, halogen, amino, cyano, cyclopropyl, cyclobutyl, —C≡CH or —CH=CH2, trifluoromethyl, —C(O)OEt or methoxy,
R3 is hydrogen,
R4 is phenyl,
R5 is hydrogen, methyl, methoxy, dimethylamino or —NHMe,
R6 is hydrogen,
R7 is —W—Y,
W is 1,2,4-triazolylene,
Y is pyridin-2-yl or pyrimidin-2-yl, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused form the following ring system

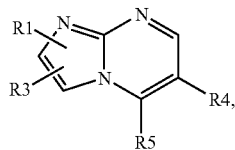

R3 is hydrogen and R1, R2, R4, R5, R6, R7, R8, R9, W and Y are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused form the following ring system

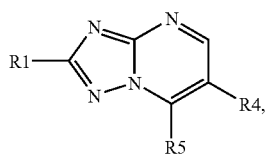

R1, R2, R4, R5, R6, R7, R8, R9, W and Y are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused form the following ring system

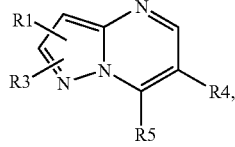

R3 is hydrogen and R1, R2, R4, R5, R6, R7, R8, R9, W and Y are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused form the following ring system

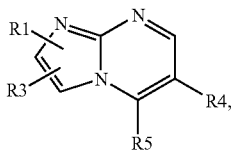

R3 is hydrogen, R6 is hydrogen, R4 is phenyl and R1, R2, R7, R8, R9, W and Y are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused form the following ring system

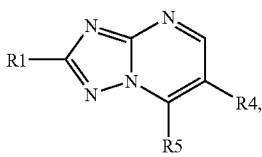

R6 is hydrogen, R4 is phenyl and R1, R2, R7, R8, R9, W and Y are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused form the following ring system

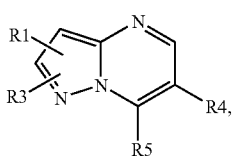

R3 is hydrogen, R6 is hydrogen, R4 is phenyl and R1, R2, R7, R8, R9, W and Y are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused form the following ring system

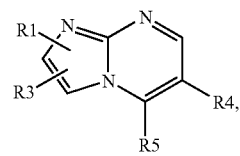

R3 is hydrogen, R6 is methyl, R4 is phenyl and R1, R2, R7, R8, R9, W and Y are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused form the following ring system

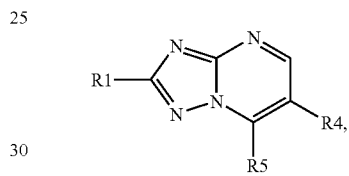

R6 is methyl, R4 is phenyl and R1, R2, R7, R8, R9, W and Y are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused form the following ring system

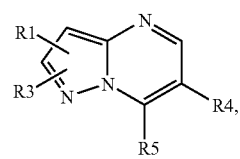

R3 is hydrogen, R6 is methyl, R4 is phenyl and R1, R2, R7, R8, R9, W and Y are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused is

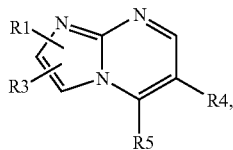

R3 is hydrogen, R6 is hydrogen, R4 is phenyl, R7 is —W—Y, W is 1,2,4-triazolylene, Y is pyridin-2-yl and R1 and R2 are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused is

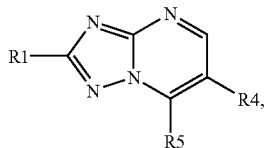

R6 is hydrogen, R4 is phenyl, R7 is —W—Y, W is 1,2,4-triazolylene, Y is pyridin-2-yl and R1 and R2 are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused is

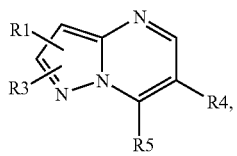

R3 is hydrogen, R6 is hydrogen, R4 is phenyl, R7 is —W—Y, W is 1,2,4-triazolylene, Y is pyridin-2-yl and R1 and R2 are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused is

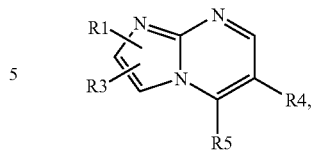

R3 is hydrogen, R6 is hydrogen, R4 is phenyl, R7 is —W—Y, W is 1,2,4-triazolylene, Y is pyrimidin-2-yl and R1 and R2 are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused is

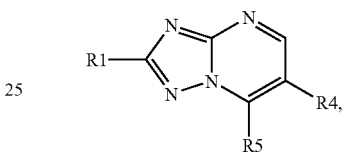

R6 is hydrogen, R4 is phenyl, R7 is —W—Y, W is 1,2,4-triazolylene, Y is pyrimidin-2-yl and R1 and R2 are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the pyrimidine to which it is fused is

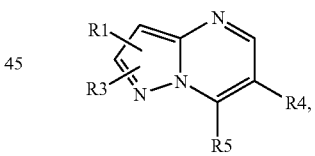

R3 is hydrogen, R6 is hydrogen, R4 is phenyl, R7 is —W—Y, W is 1,2,4-triazolylene, Y is pyrimidin-2-yl and R1 and R2 are as described above, or a salt, particularly a pharmaceutically acceptable salt, a tautomer, or a stereoisomer of said compound, or a salt, particularly a pharmaceutically acceptable salt, of said tautomer or said stereoisomer.

Salts of the compounds according to the invention include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

One aspect of the invention are salts of the compounds according to the invention including all inorganic and organic acid addition salts, especially all pharmaceutically acceptable inorganic and organic acid addition salts, particularly all pharmaceutically acceptable inorganic and organic acid addition salts customarily used in pharmacy. Another aspect of the invention are the salts with di- and tricarboxylic acids.

Examples of acid addition salts include, but are not limited to, hydrochlorides, hydrobromides, phosphates, nitrates, sulfates, salts of sulfamic acid, formates, acetates, propionates, citrates, D-gluconates, benzoates, 2-(4-hydroxybenzoyl)benzoates, butyrates, salicylates, sulfosalicylates, lactates, maleates, laurates, malates, fumarates, succinates, oxalates, malonates, pyruvates, acetoacetates, tartarates, stearates, benzensulfonates, toluenesulfonates, methanesulfonates, trifluoromethansulfonates, 3-hydroxy-2-naphthoates, benzenesulfonates, naphthalinedisulfonates and trifluoroacetates.

Examples of salts with bases include, but are not limited to, lithium, sodium, potassium, calcium, aluminum, magnesium, titanium, meglumine, ammonium, salts optionally derived from $NH_3$ or organic amines having from 1 to 16 C-atoms such as e.g. ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylendiamine, N-methylpiperindine and guanidinium salts.

The salts include water-insoluble and, particularly, water-soluble salts.

According to the person skilled in the art the compounds of formula (I) according to this invention as well as their salts may contain, e.g. when isolated in crystalline form, varying amounts of solvents. Included within the scope of the invention are therefore all solvates and in particular all hydrates of the compounds of formula (I) according to this invention as well as all solvates and in particular all hydrates of the salts of the compounds of formula (I) according to this invention.

The compounds according to the invention and their salts can exist in the form of tautomers. In particular, those compounds of the invention which contain a pyrazole moiety for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers

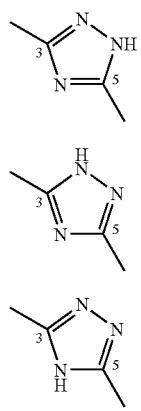

1H-tautomer 2H-tautomer 4H-tautomer

The compounds according to the invention and the salts thereof include stereoisomers. Each of the stereogenic centers present in said stereoisomers may have the absolute configuration R or the absolute configuration S (according to the rules of Cahn, Ingold and Prelog). Accordingly, the stereoisomers (1S) and (1R) in

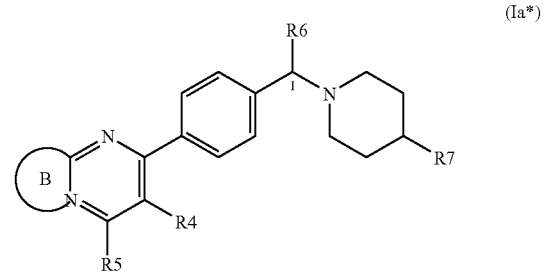

case of a compound of formula (Ia*)

and the salts thereof are part of the invention.

The invention further includes all mixtures of the stereoisomers mentioned above independent of the ratio, including the racemates.

Some of the compounds and salts according to the invention may exist in different crystalline forms (polymorphs) which are within the scope of the invention.

Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

The intermediates used for the synthesis of the compounds of claims 1-5 as described below as well as their use for the synthesis of the compounds of claims 1-5 are one further aspect of the present invention.

The compounds according to the invention can be prepared as follows.

As shown in reaction scheme 1 the compounds of formula (I), wherein ring B and the pyrimidine to which it is fused, R4, R5 and R7 have the above mentioned meanings and R6 is hydrogen or 1-4C-alkyl, can be obtained by a reductive amination reaction of a corresponding compound of formula (III), wherein R has the meaning —C(O)R6, with a piperidine derivative of formula (II), wherein R7 has the above-mentioned meanings. The reductive amination can be carried out according to standard procedures, for example by the use of NaBH(OAc)3 or NaBH3CN in a suitable solvent exemplified by dimethylformamide (DMF) or methanol or mixtures of methanol and DMF.

The piperidine derivatives of formula (II), wherein R7 has the above-mentioned meanings are known or can be prepared according to known procedures (they may contain protecting group(s) in certain cases to protect other functionalities such as but not limited to NH functions).

The use of the compounds of formula (II) for the synthesis of the compounds of claims 1-5 is one aspect of the present invention.

Compounds of formula (III), wherein R has the meaning —C(O)H can be obtained from corresponding compounds of formula (III), wherein R has the meaning —C(O)O(1-4C-alkyl), in a one or two step procedure. The ester group is selectively reduced to the aldehyde group by methods known to the skilled person, for example by the use of diisobutylaluminium hydride (DIBALH) under low temperature for example −80 to −60° C. in the one step procedure. Alternatively, the ester group is reduced to the alcohol group (—CH2OH) according to known procedures, for example by the use of LiAlH4 or NaBH4, and then, the resulting alcohol is selectively oxidized to the —C(O)H group by methods known to the skilled person, for example with SO3-pyridine complex or Dess-Martin Periodinane, in the two step procedure.

Alternatively to the reaction sequence described above, the compounds of formula (I), wherein ring B and the pyrimidine to which it is fused, R4, R5 and R7 have the above mentioned meanings and R6 is hydrogen or 1-4C-alkyl, can be obtained by reaction of a corresponding compound of formula (IIIa), wherein X is a suitable leaving group, such as for example a halogen atom or a sulfonester, with piperidine derivatives of formula (II), wherein R7 has the above-mentioned meanings. The reaction is preferably carried out in an inert solvent, such as for example DMF, at a temperature of from 60 to 100° C. in presence of a base, such as for example triethylamine.

Compounds of formula (IIIa), wherein X is a suitable leaving group, for example a halogen atom can be obtained from corresponding compounds of formula (III), wherein R is —CH(R6)OH and R6 is hydrogen or 1-4C-alkyl, by a halogenation reaction. Such a halogenation reaction can be accomplished, for example, by the use of PBr3 in dichloromethane.

Alternatively, compounds of formula (IIIa), wherein X is a suitable leaving group, for example a halogen atom can be obtained by benzylic halogenation from corresponding compounds of formula (III), wherein R is —CH2R6 and R6 is hydrogen or 1-4C-alkyl. Benzylic halogenation can, for example, be achieved by the use of N-bromosuccinimide (NBS).

Compounds of formula (III), wherein R is —CH(R6)OH and R6 is hydrogen or 1-4C-alkyl, can, for example, be obtained from corresponding compounds of formula (III), wherein R is —C(O)R6, by methods known to the person skilled in the art, for example by reduction with NaBH$_4$ or LiAlH$_4$.

Alternatively, compounds of formula (III), wherein R is —CH(R6)OH and R6 is hydrogen or 1-4C-alkyl, can be obtained from corresponding compounds of formula (III), wherein R is —CH2R6, by means of benzylic oxidation, which can be achieved, for example, by the use of catalytic or equimolar amounts of SeO2.

In a further alternative, compounds of formula (III), wherein R is —CH(1-4C-alkyl)OH can be obtained from corresponding compounds of formula (III), wherein R is —C(O)H by the addition of a suitable metal organic reagent, such as, but not limited to Gringnard or Lithium reagents.

If necessary for the reactions in reaction scheme 1, for the synthesis of compounds of formula (III), wherein ring B and the pyrimidine to which it is fused, R4 and R5 have the above mentioned meanings and R is —C(O)R6 or —CH(R6)OH, these groups can be protected in some or all of the precursors by suitable protecting groups known to the person skilled in the art. Compounds of formula (III), wherein ring B and the pyrimidine to which it is fused, R4 and R5 have the above mentioned meanings and R is a protected ketone, aldehyde or alcohol group, can be deprotected by art-known removal of the protecting groups to generate the corresponding deprotected compounds.

Compounds of formula (III), wherein ring B and the pyrimidine to which it is fused and R4 and R5 have the above mentioned meanings and R is —C(O)O(1-4C-alkyl), —C(O)R6, —CH(R6)OH or —CH2R6 and R6 is hydrogen or 1-4C-alkyl, can be obtained by a transition metal catalysed C—C bond formation of a corresponding compound of formula (V), wherein X1 is Cl, Br, I, or —OS(O)$_2$CF$_3$, with a corresponding compound of formula (IV), wherein A, for example, is —B(OH)$_2$,

—Sn(1-4C-alkyl)$_3$, —ZnCl, —ZnBr, —ZnI. This transition metal catalysed C—C bond formation reaction can, for example, be achieved if A has the meaning of —B(OH)$_2$ in a mixture of 1,2-dimethoxyethane and Na2CO3 solution at a temperature between 60-100° C. and by employing a Pd catalyst such as but not limited to 1,1'-bis(diphenylphosphino)ferrocene]palladium or Pd(PPh3)4.

Compounds of formula (IV) are either commercially available or can be prepared from commercially available compounds by methods known to the person skilled in the art.

Reaction Scheme 1:

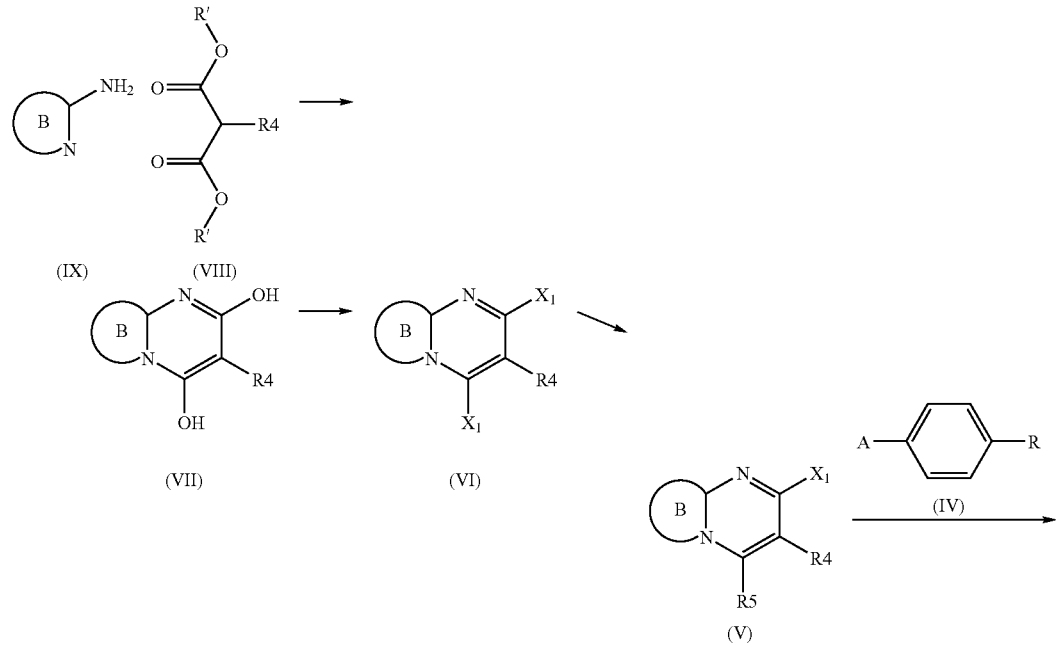

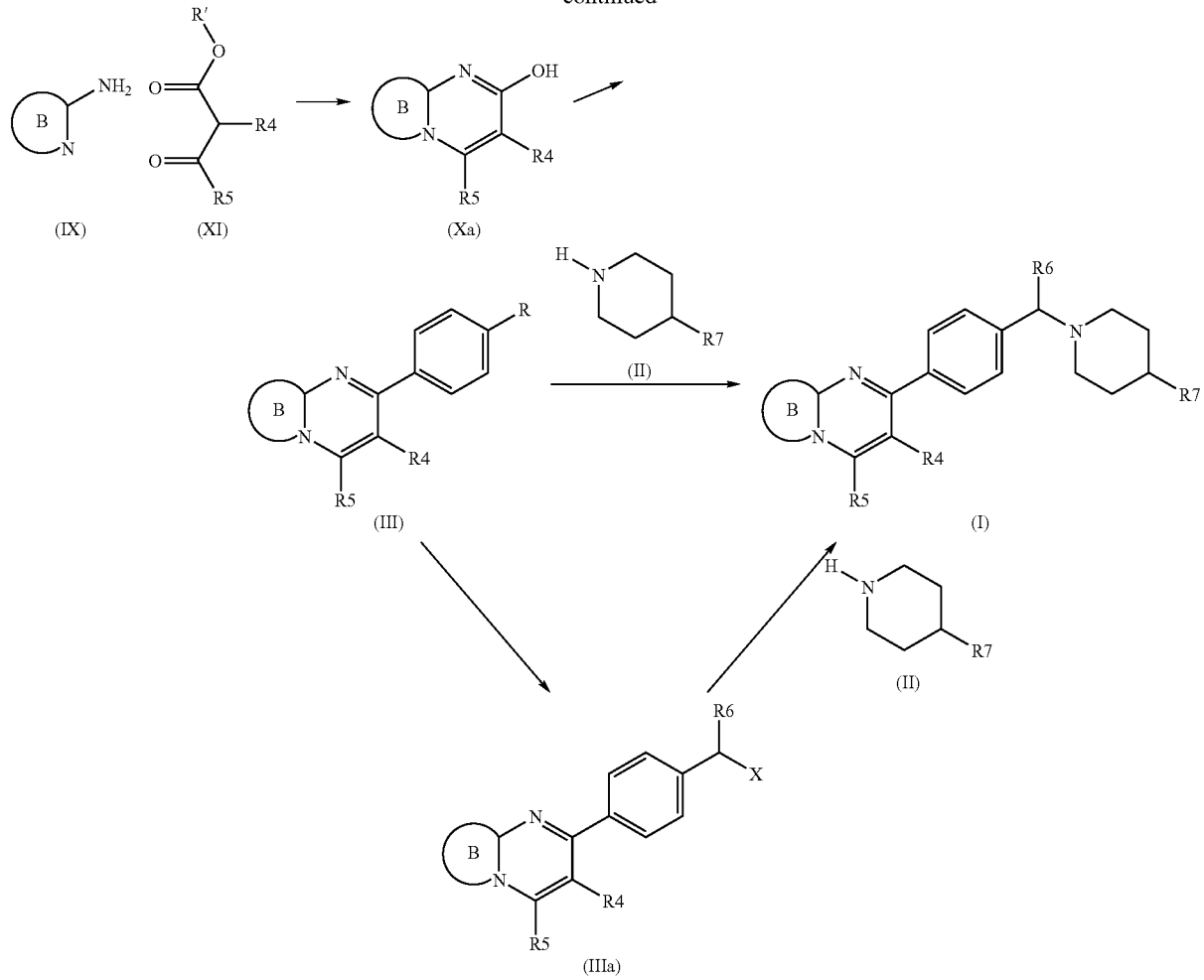

Compounds of formula (V), wherein ring B and the pyrimidine to which it is fused and R4 have the above mentioned meanings and X1 is a halogen or —OS(O)2CF3 and R5 is hydrogen, can be obtained by reaction of a corresponding compound of formula (VI). This reaction can for example be achieved by reaction with a Zinc/Copper pair in a mixture of glacial acetic acid, methanol and tetrahydrofurane (THF) at elevated temperatures of from 70 to 130° C. Alternative this reaction can for example be achieved by reaction with zinc in a mixture of ammonia solution, dichloromethane and brine at elevated temperatures of from 0 to 80° C.

Alternatively, compounds of formula (V), wherein R5 is a amino or mono- or di-1-4C-alkylamino, can be obtained by reaction of a corresponding compound of formula (VI) with the respective corresponding amino compound, for example NHCH3.

Alternatively, compounds of formula (V), wherein R5 is a 1-4C-alkyl or 3-7C-cycloalkyl, can be obtained by reaction of a corresponding compound of formula (VI) with reagents suitable for catalyzed or uncatalyzed C—C bond formation such as but not limited to boronic acids, zinc reagents, tin reagents, cyanide salts and Gringnard reagents. Catalysts suitable for these conversions are for example certain Pd or Cu complexes such as Pd(PPh3)4.

Alternatively, compounds of formula (V), wherein R5 is a 1-4C-alkoxy, can be obtained by reaction of a corresponding compound of formula (VI) with the respective compounds of formula NaO(1-4C-alkyl) in the respective solvents of formula HO(1-4C-alkyl).

A further alternatively, compound of formula (V), wherein ring B and the pyrimidine to which it is fused and R4 have the meanings described above and X1 is a halogen or —OS(O)2CF3 and R5 has the meaning of 1-4C-alkyl or 3-7-cycloalkyl, can for example be prepared from corresponding compounds of formula (Xa) by treatment with POCl3 in the case that X1 has the meaning of Cl, PBr3 or POBr in the case that X1 has the meaning of Br and or treatment with trifluorosulfonic acid anhydride if X1 has the meaning of —OS(O)2CF3.

Compounds of formula (VI), wherein ring B and the pyrimidine to which it is fused and R4 have the meanings described above and X1 is halogen or —OS(O)2CF3, can be synthesized from corresponding compounds of formula (VII) with, for example, POCl3, PBr3, POBr or trifluorosulfonic acid anhydride.

Compounds of formula (VII), wherein ring B and the pyrimidine to which it is fused and R4 have the above mentioned meanings, can be prepared with a condensation of the corresponding amino heteroaromates of formula (IX) and the malonat esters of formula (VIII), wherein R' has the meaning of 1-4C alkyl. This reaction can, for example, be accomplished in DMF at elevated temperatures of from 80 to 200° C. and by employing a base such diaza(1,3)bicyclo[5.4.0]undecane (DBU) or tributylamine.

Compounds of formula (Xa), wherein ring B and the pyrimidine to which it is fused and R4 have the above mentioned meanings and R5 is 1-4C-alkyl or 3-7-cycloalkyl can, for example, be prepared from corresponding compounds of formula (XI) with corresponding compounds of formula (IX). This reaction can, for example, be accomplished in DMF at elevated temperatures of from 80 to 200° C. and by employing a base such DBU or tributylamine.

Compounds of formulae (VIII), (IX) and (XI) are either commercially available or can be prepared from commercially available compounds by methods known to the person skilled in the art.

Reaction scheme 2

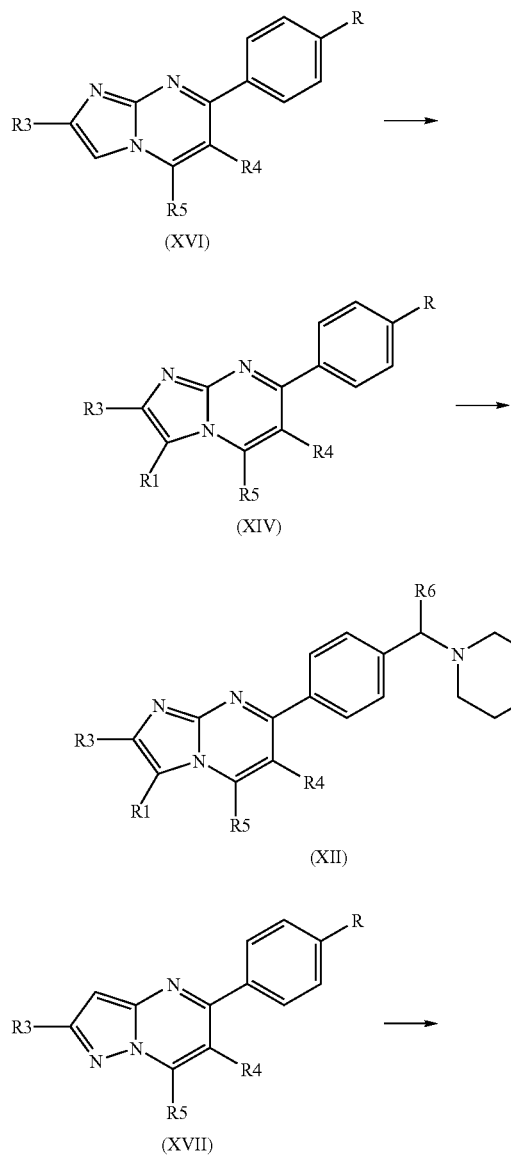

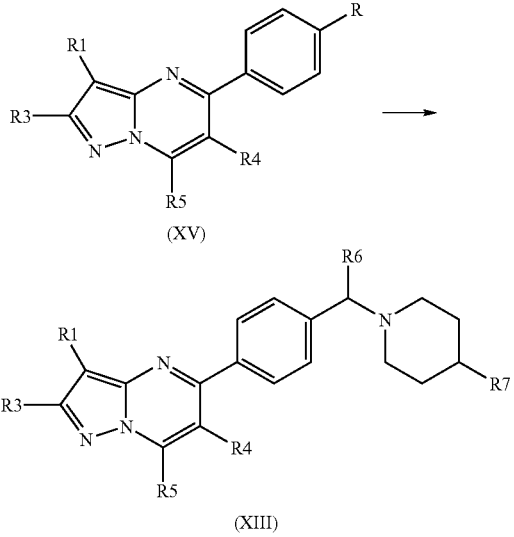

Compounds of formula (XII) and (XIII) in reaction scheme 2, wherein R1, R3, R4, R5, R6 and R7 have the meanings described above, can be prepared from corresponding compounds of formula (XIV) and (XV), wherein R is —C(O)O (1-4C-alkyl), —C(O)R6, —CH(R6)OH or —CH2R6 and R6 is hydrogen or 1-4C-alkyl, by a reductive amination reaction analogously as described above for the conversion of compounds of formula (III) to compounds of formula (I) in reaction scheme 1.

Compounds of formula (XIV) and (XV) wherein R3, R4 and R5 have the above mentioned meanings and R is —C(O)O(1-4C-alkyl), —C(O)R6, —CH(R6)OH or —CH2R6 and R6 is hydrogen or 1-4C-alkyl and R1 is halogen, can be directly synthesized by a halogenation reaction of the corresponding compounds of formula (XVI) and (XVII). For example by treatment with N-bromosuccinimide if R1 has the meaning of Br or N-chlorosuccinimide if R1 has the meaning of Cl or N-iodosuccinimide if R1 has the meaning of 1. If R1 has the meaning of F in compounds of formula (XIV) and (XV), this conversion can for example be achieved by treatment of compounds of formula (XVI) and (XVI) respectively with 1-chloromethyl-4-fluoro-1,4-diazoniabicyclo[2.2.2]octane bis(tetrafluoroborate), for example in chloroform at temperatures such as 80-130° C.

Compounds of formula (XIV) and (XV), wherein R1 has the meaning of 1-3C-alkyl, 3-7C-cycloalkyl, —CN, 2-4C-alkenyl and 2-4C-alkynyl can be obtained from corresponding compounds of formula (XIV) and (XV), wherein R1 has the meaning of a halogen, by reaction with a metal organic reagent, such as, but not limited to 1-3C-alkyl-B(OH)2, 1-3C-alkyl-ZnCl, 1-3C-alkyl-ZnBr, 1-3C-alkyl-ZnI, 3-7C-cycloalkyl-B(OH)2, 3-7C-cycloalkyl-ZnCl, 3-7C-cycloalkyl-ZnBr, 3-7C-cycloalkyl-ZnI, 2-4C-alkenyl-B(OH)2, 2-4C-alkenyl-ZnCl, 2-4C-alkenyl-ZnBr, 2-4C-alkenyl-ZnI, 2-4C-alkynyl-B(OH)2, 2-4C-alkynyl-ZnCl, 2-4C-alkynyl-ZnBr, 2-4C-alkynyl-ZnI, Zn(CN)2 and 2-4C-alkynyls with a terminal triple bond, for example by employing Pd catalysts know to the person skilled in the art, for example Pd(PPh3)4 or 1,1'-bis(diphenylphosphino)ferrocene]palladium.

Compounds of formula (XIV) and (XV) wherein R1 has the meaning 1-4C-alkyl can be synthesized from respective compounds formula (XIV) and (XV) wherein R1 has the meaning of 1-4C-alkenyl or 1-4C-alkynyl for example by means of hydrogenation.

Compounds of formula (XVI) and (XVII) in reaction scheme 2, wherein R3, R4 and R5 have the meaning described above and R is —C(O)O(1-4C-alkyl), —C(O)R6, —CH(R6)OH or —CH2R6 and R6 is hydrogen or 1-4C-alkyl can prepared as described in reaction scheme 1 for compounds of formula (III).

If necessary for the reactions in reaction scheme 2, for the synthesis of compounds of formula (XII) and (XIII), wherein R is —C(O)R6 or —CH(R6)OH and R6 is hydrogen or 1-4C-alkyl, these groups can be protected in some or all of the pre-cursors by suitable protecting groups known to the person skilled in the art. Compounds of formula (XII) and (XIII), in which R is a protected ketone, aldehyde or alcohol group, can be deprotected by art-known removal of the protecting groups to generate the corresponding deprotected compounds.

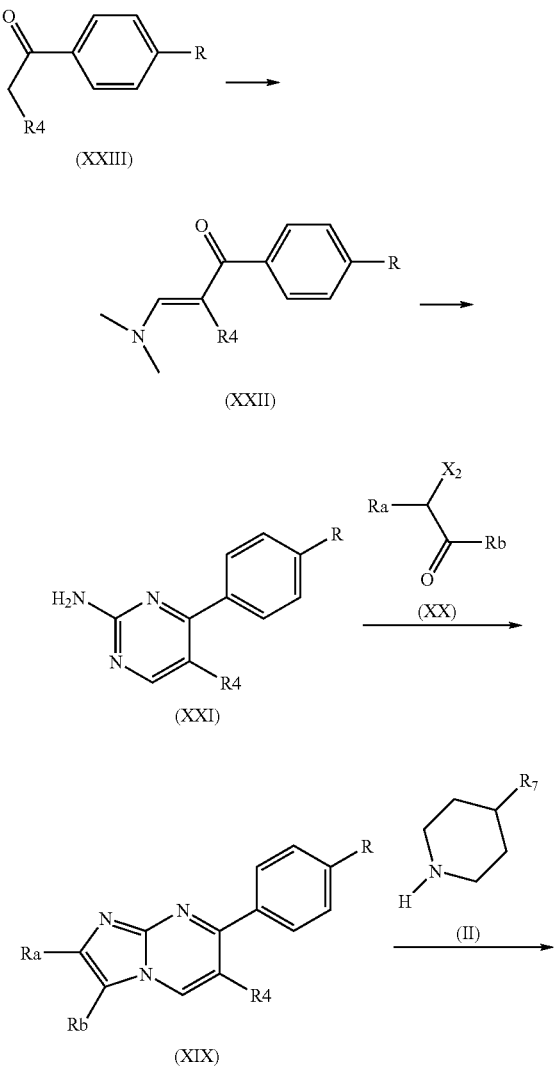

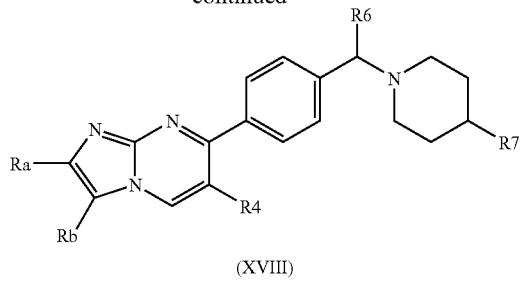

(XVIII)

As shown in reaction scheme 3, compounds of formula (XVIII), wherein one of Ra and Rb has the meaning of R1 and the other of R3 and wherein R1, R3, R4, R6 and R7 have the meanings described above, can be prepared by a reductive amination reaction from corresponding compounds of formula (XIX), wherein R is —C(O)O(1-4C-alkyl), —C(O)R6, —CH(R6)OH or —CH2R6 and R6 is hydrogen or 1-4C-alkyl, with a compound of formula (II). This reductive amination reaction can be achieved analogously as described above in reaction scheme 1 for the conversion of compounds of formula (III) to compounds of formula (I).

Compounds of formula (XIX), wherein one of Ra and Rb has the meaning of R1 and the other of R3 and wherein R1, R3, R4 have the meanings described above and wherein R is —C(O)O(1-4C-alkyl), —C(O)R6, —CH(R6)OH or —CH2R6 and R6 is hydrogen or 1-4C-alkyl, can be prepared by reaction of a compound of formula (XX), wherein X2 has the meaning of a halogen or a sulfonester, with a corresponding compound of formula (XXI). This reaction can for example achieved in refluxing ethanol.

Compounds of formula (XX) are either commercially available or can be prepared from commercially available compounds by methods known to the person skilled in the art.

Compounds of formula (XXI), wherein R4 has the meaning described above and R has the meanings of —C(O)O(1-4C-alkyl), —C(O)R6, —CH(R6)OH or —CH2R6 and R6 is hydrogen or 1-4C-alkyl, can for example be prepared from corresponding compounds of formula (XXII) by reaction with guanidine hydrochloride and NaOCH3 in methanol.

Compounds of formula (XXII), wherein R4 has the meaning described above and R has the meaning of —C(O)O(1-4C-alkyl), —C(O)R6, —CH(R6)OH or —CH2R6 and R6 is hydrogen or 1-4C-alkyl, can be prepared from corresponding compounds of formula (XXIII). This can for example be achieved by reaction with N,N-dimethylformamide dimethylacetal in DMF at elevated temperature of from 80 to 120° C.

Compounds of formula (XXIII) are either commercially available or can be prepared from commercially available compounds by methods known to the person skilled in the art.

If necessary for the reactions in reaction scheme 3, for the synthesis of compounds of formula (XIX), wherein R is —C(O)O(1-4C-alkyl), —C(O)R6 or —CH(R6)OH and R6 is hydrogen or 1-4C-alkyl these groups can be protected in some or all of the precursors by suitable protecting groups known to the person skilled in the art. Compounds of formula (XIX), in which R is a protected ketone, aldehyde or alcohol group, can be deprotected by art-known removal of the protecting groups to generate the corresponding deprotected compounds.

One preferred aspect of the invention is the process for the preparation of the compounds of claims 1-5 according to the examples.

Optionally, compounds of the formula (I) can be converted into their salts, or, optionally, salts of the compounds of the formula (I) can be converted into the free compounds. Corresponding processes are customary for the skilled person.

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the compounds and salts according to the invention can be obtained e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids such as e.g. mandelic acid can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

EXAMPLES

The following abbreviations are used: In the examples, m.p. stands for melting point, h or hrs for hour(s), min for minutes, conc. for concentrated, calc. for calculated, fnd. for found, EF for elemental formula, MS for mass spectrometry, M for molecular ion in mass spectrometry, TLC: thin layer chromatography, HPLC for high performance liquid chromatography, $^1$H-NMR for $^1$H nuclear magnetic resonance spectroscopy (chemical shifts are reported as ppm against tetramethylsilane as internal standard, coupling constants J are reported in Hz), w/w for weight by weight, RT for room temperature (20-25° C.), DCM for dichloromethane, THF for tetrahydrofurane, DMSO for dimethylsulfoxide, DBU for 1,8-diazabicyclo[5.4.0]undec-7-ene, EtOAc for ethyl acetate, DIBAL for diisobutylaluminium hydride, DCM for dichloromethane, ACN for acetonitril and other abbreviations have their meanings customary per se to the skilled person.

Example 1

6-phenyl-7-(4-{[4-(3-pyridin-2-yl-1,2,4-triazol-5-yl) piperidin-1-yl]methyl}phenyl)imidazo[1,2-a]pyrimidine Step 1: 6-phenylimidazo[1,2-a]pyrimidine-5,7-diol 18.3 g (0.0776 mol) diethylphenylmalonate and 20.5 g (0.0776 mol) 2-aminoimidazole sulfate are dissolved in 93 ml DMF and 35 ml DBU and the mixture heated to 100° C. for 15 h. The solvent is removed, the residue dissolved in water and re-precipitated by adjusting the pH to 1 with 2 mol/l HCl. The precipitate is collected by filtration to obtain the desired product.

MS (M+1): 228

Step 2: 5,7-dichloro-6-phenylimidazo[1,2-a]pyrimidine 8 g 6-phenylimidazo[1,2-a]pyrimidine-5,7-diol is dissolved in 40 ml POCl$_3$ and 6.7 ml (52.8 mmol) dimethylaniline. The mixture is heated to 100° C. for 2 h. The solvent is removed, the residue dissolved in a mixture of dichloromethane, water and ice, the organic phase separated and the water-phase extracted with dichloromethane. The combined dichloromethane phase is washed with sodium chloride-solution, dried over Na$_2$SO$_4$ and evaporated. The residue is purified by silica gel chromatography (dichloromethane/ethyl acetate) yielding the desired product.

MS (M+1) 264

Characteristic 1H NMR signals (200 MHz, dDMSO): 8.1 (d, 1H); 7.9 (d, 1H)

Step 3: 7-chloro-6-phenylimidazo[1,2-a]pyrimidine 10 g 5,7-dichloro-6-phenylimidazo[1,2-a]pyrimidine and 7.3 g Zinc/Copper pair are suspended in 5 ml glacial acetic acid, 10 ml methanol and 60 ml THF and the mixture is heated to 50° C. for 1 h. The mixture is filtered over celite, diluted with dichloromethane and washed with water. The organic phase is dried over sodium sulfate and evaporated to obtain the crude product, a mixture of the desired product and 6-phenylimidazo[1,2-a]pyrimidine. This mixture is used for the next reaction without further purification.

MS (M+1): 230/232

Characteristic 1H NMR signals (200 MHz, dDMSO): 9.1 ppm (s, 1H); 7.8 (d, 1H); 7.9 (d, 1H)

Step 4: 4-(6-phenylimidazo[1,2-a]pyrimidin-7-yl) benzaldehyde

To a mixture of 6 g of the crude product obtained in step 3 and 5.1 g 4-formylphenylboronic acid in 210 ml 1,2-dimethoxyethane are added 0.96 g dichloro[1,1'-bis(diphenylphosphino)ferrocene]palladium (II) dichloromethane adduct and 42 ml of a 10% w/w sodium carbonate solution. The resulting mixture is heated to 80° C. under an inert gas atmosphere for 15 h. The work up is performed by diluting the reaction mixture with water and dichloromethane, separating the phases and extraction of the aqueous phase with dichloromethane. The combined organic layers are dried over sodium sulphate and evaporated. The residue is suspended in ethyl acetate and the resulting mixture stirred for 2 h at room temperature. The product is collected by filtration and used without further purification.

MS (M+1): 300

Characteristic 1H NMR (300 MHz, dDMSO) signals: 10 ppm (s, 1H), 9.1 ppm (s, 1H), 8.0 ppm (d, 1H)

Step 5: 6-phenyl-7-(4-{[4-(3-pyridin-2-yl-1,2,4-triazol-5-yl)piperidin-1-yl]methyl}phenyl)imidazo[1,2-a]pyrimidine 0.55 ml triethylamine is added to a solution of 0.5 g 4-(6-phenylimidazo[1,2-a]pyrimidin-7-yl)benzaldehyde in 15 ml methanol. To this solution a solution of 0.6 g 2-(5-Piperidin-[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 15 ml DMF is added, followed by 0.25 ml glacial acetic acid and 700 mg NaBH(OAc)$_3$. The resulting mixture is stirred at room temperature. Three additional portions of 2 equivalents NaBH(OAc)$_3$ are added after 2, 4 and 20 hours.

The solvens is removed by evaporation after 24 h and the residue is purified by chromatography on silica gel (dichlormethan/methanol) to yield the desired product.

MS (M+1): 513

Characteristic 1H NMR (400 MHz, dDMSO) signals: 9 ppm (s, 1H); 8.2 ppm (1H), 3.5 ppm (s, 2H)

Example 2

6-phenyl-5-(4-{[4-(5-pyridin-2-yl-1,2,4-triazol-3-yl) piperidin-1-yl]methyl}phenyl)[1,2,4]triazolo[1,5-a] pyrimidine Step 1:
6-phenyl[1,2,4]triazolo[1,5-a]pyrimidine-5,7-diol A solution of 10 g 1,2,4-triazol-3-amine and 33.7 g diethyl phenylmalonate in N,N-dibutylbutan-1-amine is stirred at 185° C. over night. The solution is diluted with 10% w/w NaOH solution, the resulting mixture is stirred for 30 min and the organic phase is separated. The aqueous layer is extracted with diethylether, acidified with concentrated HCl until precipition of the product is complete and the precipitate collected by filtration to yield the product, which is used without further purification.

MS (M+1): 229

Characteristic 1H NMR (200 MHz, dDMSO) signals: 8.7 ppm (s, 1H)

Step 2: 5,7-dichloro-6-phenyl[1,2,4]triazolo[1,5-a] pyrimidine 2.45 g 6-phenyl[1,2,4]triazolo[1,5-a]pyrimidine-5,7-diol is suspended in 4.1 ml POCl$_3$ and the mixture is stirred for 4 h at 100° C. for 2 h. The solvent is removed, the residue dissolved in a mixture of dichloromethane, water and ice, the organic phase is separated and water-phase is extracted with dichloromethane. The combined dichloromethane phase is dried over Na$_2$SO$_4$ and evaporated. The crude product is used without further purification.

MS (M+1): 265

Characteristic 1H NMR (200 MHz, dDMSO) signals: 8.8 ppm (s, 1H)

Step 3:
5-chloro-6-phenyl[1,2,4]triazolo[1,5-a]pyrimidine

A mixture of 0.5 g 5,7-dichloro-6-phenyl[1,2,4]triazolo[1,5-a]pyrimidine, 0.22 ml glacial acetic acid, 0.5 ml methanol, 3 ml THF and 366 mg of Zn/Cu pair are stirred for 3 h at ambient temperature. The mixture is filtered through celite, evaporated to dryness and the residue is purified on silica gel (dichloromethane/ethyl acetate) to yield the desired product.

MS (M+1): 231/233

Characteristic 1H NMR (400 MHz, dDMSO) signals: 9.6 ppm (s, 1H); 8.8 ppm (s, 1H)

Step 4: 4-(6-phenyl[1,2,4]triazolo[1,5-a]pyrimidin-5-yl)benzaldehyde

To a mixture of 130 mg 5-chloro-6-phenyl[1,2,4]triazolo[1,5-a]pyrimidine and 93 mg 4-formylphenylboronic acid in 5 ml 1,2-dimethoxyethane are added 1.2 ml of a 10% w/w sodium carbonate solution and 65 mg tetrakis(triphenylphosphine) palladium(0) and the resulting mixture is heated to 90° C. under an inert gas atmosphere for 18 h. The work up is performed by diluting the reaction mixture with water and dichloromethane, separating the phases and extraction of the aqueous phase with dichloromethane. The combined organic layers are dried over sodium sulphate, evaporated and the residue suspended in methanol. The crystalline product is isolated by filtration yielding the desired product. The filtrate is evaporated to dryness, dissolved in ethyl acetate and additional product precipitated by the addition of petrolether.

MS (M+1): 301
Characteristic 1H NMR (400 MHz, dDMSO) signals: 10 ppm (s, 1H), 9.6 ppm (s, 1H); 8.8 ppm (d, 1H)

Step 5: 6-phenyl-5-(4-{[4-(5-pyridin-2-yl-1,2,4-triazol-3-yl)piperidin-1-yl]methyl}phenyl)[1,2,4]triazolo[1,5-a]pyrimidine 0.09 ml triethylamine is added to a solution of 80 mg 4-(6-phenyl[1,2,4]triazolo[1,5-a]pyrimidin-5-yl)benzaldehyde in 3 ml methanol. To this solution a solution of 97 mg 2-(5-Piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 3 ml DMF is added, followed by 0.04 ml glacial acetic acid and 114 mg NaBH(OAc)$_3$. The resulting mixture is stirred at room temperature. Three additional portions of 2 equivalents NaBH(OAc)$_3$ are added after 2, 4 and 5 hours.

The solvent is removed by evaporation after 6 h and the residue is purified by chromatography on silica gel (dichloromethane/methanol) to yield the crude product, which is further purified by RP HPLC (Water, 10 mM NH$_4$COOH, pH 3.7/ACN).
MS (M+1): 514
Characteristic 1H NMR (dDMSO, 400 MHz) signals: 9.5 ppm (s, 1H); 8.7 ppm (s, 1H), 3.5 ppm (s, 2H)

Example 3

2-methyl-6-phenyl-5-(4-{[4-(5-pyridin-2-yl-1,2,4-triazol-3-yl)piperidin-1-yl]methyl}phenyl)[1,2,4]triazolo[1,5-a]pyrimidine This compound is prepared in a manner according to example 2 or example 37 by using 5-methyl-1,2,4-triazol-3-amine in the first step.
MS (M+1): 528
Characteristic 1H NMR (dDMSO, 400 MHz) signals: 9.3 ppm (s, 1H); 8.7 ppm (d, 1H), 3.5 ppm (s, 2H); 2.6 ppm (s, 3H)

Example 4

2-cyclopropyl-6-phenyl-5-(4-{[4-(5-pyridin-2-yl-1,2,4-triazol-3-yl)piperidin-1-yl]methyl}phenyl)[1,2,4]triazolo[1,5-a]pyrimidine This compound is prepared in a manner according to example 2 or example 37 by using 5-cyclopropyl-1,2,4-triazol-3-amine in the first step.
MS (M+1): 554
Characteristic 1H NMR (dDMSO, 300 MHz) signals: 9.3 ppm (s, 1H); 8.7 ppm (s, broad, 1H)

Example 5

6-phenyl-7-(4-{[4-(3-pyridin-2-yl-pyrazol-5-yl)piperidin-1-yl]methyl}phenyl)imidazo[1,2-a]pyrimidine Example 5 is synthesized in a manner according to example 1 by using 2-(5-piperidin-4-yl-pyrazol-3-yl)pyridine*HCl instead of 2-(5-Piperidin-[1,2,4]triazol-3-yl)-pyridine in the last step which was prepared as described in Bioorg. Med. Chem. Lett.; EN; 12; 3; 2002; 383-386.

MS (M+1): 512
Characteristic 1H NMR (300 MHz, dDMSO) signals: 9.0 ppm (s, 1H); 6.6 ppm (s, 1H); 3.5 ppm (s, 2H)

Example 6

6-phenyl-7-(4-{[4-(5-pyridin-4-yl-1,2,4-triazol-3-yl)piperidin-1-yl]methyl}phenyl)imidazo[1,2-a]pyrimidine Example 6 is synthesized in a manner according to example 1 by using 4-(5-piperidin-4-yl-4H-1,2,4-triazol-3-yl)pyridine instead of 2-(5-Piperidin-[1,2,4]triazol-3-yl)-pyridine, which is synthesized from tert-butyl 4-(hydrazinocarbonyl)piperidine-1-carboxylate and pyridine-4-carbonitrile according to a procedure described in U.S. Pat. No. 4,011,218 or WO2005100344.
MS (M+1): 513
Characteristic 1H NMR (400 MHz, dDMSO) signals: 9.0 ppm (s, 1H); 3.5 ppm (s, 2H)

Example 7

2-cyclobutyl-6-phenyl-5-(4-{[4-(5-pyridin-2-yl-1,2,4-triazol-3-yl)piperidin-1-yl]methyl}phenyl)[1,2,4]triazolo[1,5-a]pyrimidine This compound is prepared in a manner according to example 2 or example 37 by using 5-cyclobutyl-1,2,4-triazol-3-amine in the first step.
MS (M+1): 568
Characteristic 1H NMR (dDMSO, 400 MHz) signals: 9.3 ppm (s, 1H); 3.8 ppm (quint., 1H)

Example 8

6-phenyl-7-(4-{[4-(5-pyridin-2-yl-1,2,4-triazol-3-yl)piperidin-1-yl]methyl}phenyl)imidazo[1,2-a]pyrimidine-3-carbonitrile Step 1: 7-(4-formylphenyl)-6-phenylimidazo[1,2-a]pyrimidine-3-carbonitrile 350 mg 4-(3-bromo-6-phenylimidazo[1,2-a]pyrimidin-7-yl)benzaldehyde (prepared as described in example 11), 5.6 mg Zn, 63.7 mg Zn(CN)2 and dichloro[1,1'-bis(diphenylphosphino)ferrocene]palladium (II) dichloromethane adduct are suspended in dimethylacetamide and the mixture is heated for 45 min under microwave irradiation to 160° C. The workup is performed by diluting the mixture with water and dichlormethane, extracting the aqueous layer twice and drying the combined organic layers over Na$_2$SO$_4$. The compound is isolated by evaporation of the solvent and chromatography on silica gel (dichloromethane/methanol).
MS (M+1): 325
Characteristic 1H NMR (300 MHz, dDMSO) signals: 10.0 ppm (s, 1H), 9.1 ppm (s, 1H), 8.7 ppm (s, 1H);

Step 2: 6-phenyl-7-(4-{[4-(5-pyridin-2-yl-1,2,4-triazol-3-yl)piperidin-1-yl]methyl}phenyl)imidazo[1,2-a]pyrimidine-3-carbonitrile 0.2 ml triethylamine is added to a solution of 260 mg of the product of step 1 in 5 ml methanol. To this solution a solution of 219 mg 2-(5-Piperidin-[1,2,4]triazol-3-yl)pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 5 ml DMF is added, followed by 0.091 ml glacial acetic acid and 127 mg NaBH(OAc)$_3$. The resulting mixture is stirred at room temperature. Additional portions of 2 equivalents NaBH(OAc)$_3$ are added after 1.5, 3 and 4 hours. The solvent is removed by evaporation after 6 h and the residue is purified by chromatography on silica gel (dichloromethane/methanol) to yield the desired compound.

MS (M+1): 538

Characteristic 1H NMR (400 MHz, dDMSO) signals: 9.0 ppm (s, 1H), 3.5 ppm (s, 2H);

Example 9

3-fluoro-6-phenyl-7-(4-{[4-(5-pyridin-2-yl-1H-1,2,4-triazol-3-yl)piperidin-1-yl]methyl}phenyl)imidazo[1,2-a]pyrimidine

Step 1: 4-(3-fluoro-6-phenylimidazo[1,2-a]pyrimidin-7-yl)benzaldehyde 500 mg 4-(6-phenylimidazo[1,2-a]pyrimidin-7-yl)benzaldehyde (prepared as described under example 1) and 880 mg 1-chloromethyl-4-fluoro-1,4-diazoniabicyclo[2.2.2]octane bis(tetrafluoroborate are dissolved in 25 ml chloroform and heated under microwave irradiation to 120° C. After for 45 min and 4 h additional portions of 200 mg of 1-chloromethyl-4-fluoro-1,4-diazoniabicyclo[2.2.2]octane bis(tetrafluoroborate are added and heating continued at 120° C. The reaction is worked up after 5 h by diluting with water and extraction with dichloromethane. The combined organic layers are dried over Na$_2$SO$_4$ and the solvens evaporated. The crude material is purified on silica gel (dichloromethane/ethyl acetate.

MS (M+1): 318

Characteristic 1H NMR (300 MHz, dDMSO) signals: 10.0 ppm (s, 1H); 8.9 ppm (s, 1H); 7.6 ppm (d, 1H);

Step 2: 3-fluoro-6-phenyl-7-(4-{[4-(5-pyridin-2-yl-1,2,4-triazol-3-yl)piperidin-1-yl]methyl}phenyl)imidazo[1,2-a]pyrimidine 0.25 ml triethylamine is added to a solution of 391 mg of the product of step 1 in 5 ml methanol. To this solution a solution of 269 mg 2-(5-Piperidin-[1,2,4]triazol-3-yl)pyridine*2HCl in 5 ml DMF is added, followed by 0.11 ml glacial acetic acid and 314 mg NaBH(OAc)3. The resulting mixture is stirred at room temperature. An additional portions of 2 equivalents NaBH(OAc)$_3$ is added after 5 hours and the solvents are removed by evaporation after 22 h. The residue is purified by chromatography on silica gel (dichloromethane/methanol) and subsequent RP HPLC (Water, 10 mM NH$_4$COOH, pH 3.7/ACN) to yield the desired compound.

MS (M+1): 531

Characteristic 1H NMR (400 MHz, dDMSO) signals: 8.8 ppm (s, 1H); 7.6 ppm (d, 1H); 3.5 ppm (s, 2H);

Example 10

N-methyl-6-phenyl-7-(4-{[4-(5-pyridin-2-yl-1,2,4-triazol-3-yl)piperidin-1-yl]methyl}phenyl)imidazo[1,2-a]pyrimidin-5-amine

Step 1: 7-chloro-N-methyl-6-phenylimidazo[1,2-a]pyrimidin-5-amine 850 mg 5,7-dichloro-6-phenylimidazo[1,2-a]pyrimidine (prepared as described for example 1) is dissolved in 18 ml of a 8M Solution of MeNH$_2$ in methanol and stirred at room temperature for 1.5 h. The product precipitates upon dilution with water and cooling to 0° C. The solid material is collected by filtration and washed twice with water to yield the desired material.

MS (M+1): 259

Characteristic 1H NMR (300 MHz, dDMSO) signals: 8.0 ppm (d, 1H); 2.3 ppm (d, 3H)

Step 2: 4-[5-(methylamino)-6-phenylimidazo[1,2-a]pyrimidin-7-yl]benzaldehyde To a mixture of 550 mg of the product of step 1 and 350 mg 4-formylphenylboronic acid in 10 ml 1,2-dimethoxyethane are, 55 mg tetrakis(triphenylphosphine) palladium(0) and 4 ml of a 10% w/w sodium carbonate solution are added and the resulting mixture is heated by microwave for 2 h. The work up is performed by diluting the reaction mixture with water and dichloromethane, separating the phases and extraction of the aqueous phase with dichloromethane. The combined organic layers are dried over sodium sulphate and evaporated. The residue is suspended in ethyl acetate and the resulting mixture is stirred for 2 h at room temperature. The product is collected by filtration and used without further purification.

MS (M+1): 329

Characteristic 1H NMR (300 MHz, dDMSO) signals: 9.9. ppm (s, 1H), 2.4 ppm (d, 3H)

Step 3: N-methyl-6-phenyl-7-(4-{[4-(5-pyridin-2-yl-1,2,4-triazol-3-yl)piperidin-1-yl]methyl}phenyl)imidazo[1,2-a]pyrimidin-5-amine 0.15 ml triethylamine is added to a solution of 150 mg of the product of reaction 2 in 5 ml methanol. To this solution a solution of 166 mg 2-(5-Piperidin-[1,2,4]triazol-3-yl)-pyridine*2HCl in 5 ml DMF is added, followed by 0.07 ml glacial acetic acid and 195 mg NaBH(OAc)$_3$. The resulting mixture is stirred at room temperature. Additional portions of 2 equivalents NaBH(OAc)$_3$ are added after 4 and 6 hours. The solvent is removed by evaporation after 24 h and the residue is purified by chromatography on silica gel (dichloromethane/[dichloromethane+8M NH$_3$ in methanol]) to yield the desired compound.

MS (M+1): 329

Characteristic 1H NMR (400 MHz, dDMSO) signals: 3.4 ppm (s, 2H), 2.4 ppm (d, 3H)

Example 11

3-bromo-6-phenyl-7-(4-{[4-(5-pyridin-2-yl-1,2,4-triazol-3-yl)piperidin-1-yl]methyl}phenyl)imidazo[1,2-a]pyrimidine

Step 1: 4-(3-bromo-6-phenylimidazo[1,2-a]pyrimidin-7-yl)benzaldehyde 1.5 g 4-(6-phenylimidazo[1,2-a]pyrimidin-7-yl)benzaldehyde (prepared as described under example 1) and 0.9 g NBS are refluxed in 30 ml chloroform for 1 h. The solvent is removed by distillation and the crude product is purified by column chromatography (dichloromethane/methanol).

MS (M+1): 378/380

Characteristic 1H NMR (300 MHz, dDMSO) signals: 10 ppm (s, 1H), 9.7 ppm (s, 1H); 8.0 (s, 1H)

Step 2: 3-bromo-6-phenyl-7-(4-{[4-(5-pyridin-2-yl-1,2,4-triazol-3-yl)piperidin-1-yl]methyl}phenyl)imidazo[1,2-a]pyrimidine 0.177 ml triethylamine is added to a solution of 200 mg 4-(3-bromo-6-phenylimidazo[1,2-a]pyrimidin-7-yl)benzaldehyde in 3 ml methanol. To this solution a solution of 199 mg 2-(5-Piperidin-[1,2,4]triazol-3-yl)-pyridine*2HCl in 5 ml DMF is added, followed by 0.081 ml glacial acetic acid and 225 mg NaBH(OAc)$_3$. The resulting mixture is stirred at room temperature. Three additional portions of 2 equivalents NaBH(OAc)$_3$ are added after 2, 5 and 22 hours.

The solvens is removed by evaporation after 24 h and the residue is purified by chromatography on silica gel (dichloromethane/methanol) to yield the desired product.

MS (M+1): 591/593

Example 12

3-chloro-6-phenyl-7-(4-{[4-(5-pyridin-2-yl-1,2,4-triazol-3-yl)piperidin-1-yl]methyl}phenyl)imidazo[1,2-a]pyrimidine Example 12 is synthesized in a manner according to example 11 by using NCS instead of NBS in step 1.

MS (M+1): 547

Characteristic 1H NMR (300 MHz, dDMSO) signals: 8.7 ppm (s, 1H), 7.9 ppm (s, 1H)

Example 13

3-ethynyl-6-phenyl-7-(4-{[4-(5-pyridin-2-yl-1,2,4-triazol-3-yl)piperidin-1-yl]methyl}phenyl)imidazo[1,2-a]pyrimidine Step 1: 4-{6-phenyl-3-[(trimethylsilyl)ethynyl]imidazo[1,2-a]pyrimidin-7-yl}benzaldehyde 400 mg 4-(3-bromo-6-phenylimidazo[1,2-a]pyrimidin-7-yl)benzaldehyde (prepared as described under example 11), 820 mg trimethyl[(tributylstannyl)ethynyl]silane and 60 mg Pd(PPh$_3$)$_4$ are suspended in 8 ml toluene under a nitrogen atmosphere. The mixture is heated (microwave) to 130° C. for 1 h. The solvent is evaporated and the crude product is purified by column chromatography (dichloromethane/methanol)

MS (M+1): 396

Characteristic 1H NMR (300 MHz, dDMSO) signals: 10 ppm (s, 1H), 8.7 ppm (s, 1H); 8.2 ppm (s, 1H); 0.3 ppm (s, 9H)

Step 2: 6-phenyl-7-(4-{[4-(5-pyridin-2-yl-1,2,4-triazol-3-yl)piperidin-1-yl]methyl}phenyl)-3-[(trimethylsilyl)ethynyl]imidazo[1,2-a]pyrimidine 0.34 ml triethylamine is added to a solution of 400 mg of the product of step 1 in 5 ml methanol. To this solution a solution of 367 mg 2-(5-Piperidin-[1,2,4]triazol-3-yl)pyridine*2HCl in 5 ml DMF is added, followed by 0.15 ml glacial acetic acid and 428 mg NaBH(OAc)$_3$. The resulting mixture is stirred at room temperature. An additional portions of 2 equivalents NaBH(OAc)$_3$ is added after 5 hours.

The solvent is removed by evaporation after 22 h and the residue is purified by chromatography on silica gel (dichloromethane/methanol) to yield a mixture of the desired compound and the compound without the trimethylsilyl-group. This mixture is used for the next reaction.

MS (M+1): 609

Step 3: 3-ethynyl-6-phenyl-7-(4-{[4-(5-pyridin-2-yl-1,2,4-triazol-3-yl)piperidin-1-yl]methyl}phenyl)imidazo[1,2-a]pyrimidine 350 mg of the mixture obtained in the previous step and 79 mg K$_2$CO$_3$ are stirred in 5 ml methanol for 3 h. The precipitated product is collected by filtration.

MS (M+1): 537

Characteristic 1H NMR (400 MHz, dDMSO) signals: 8.2 ppm (s, 1H), 5.0 ppm (s, 1H)

Example 14

3-methyl-6-phenyl-7-(4-{[4-(5-pyridin-2-yl-1,2,4-triazol-3-yl)piperidin-1-yl]methyl}phenyl)imidazo[1,2-a]pyrimidine Example 14 is synthesized in a manner according to example 8 by using MeZnCl instead of Zn and ZnCN$_2$ in step 1.

MS (M+1): 527

Characteristic 1H NMR (400 MHz, dDMSO) signals: 8.7 ppm (s, 1H), 8.2 ppm (s, 1H), 2.6 ppm (s, 3H)

Example 15

6-phenyl-7-(4-{[4-(5-pyridin-2-yl-1,2,4-triazol-3-yl)piperidin-1-yl]methyl}phenyl)-3-vinylimidazo[1,2-a]pyrimidine Step 1: 4-(6-phenyl-3-vinylimidazo[1,2-a]pyrimidin-7-yl)benzaldehyde 500 mg 4-(3-bromo-6-phenylimidazo[1,2-a]pyrimidin-7-yl)benzaldehyde (prepared as described under example 11), 180 mg K$_2$CO$_3$, 215 mg Et$_4$NCl, 25 mg PdCl2(PPh$_3$)$_2$ and 620 mg tributyl(vinyl)stannane are suspended in 10 ml THF. The mixture is heated to 110° C. for 45 min. This mixture is worked up by diluting with water and extraction with dichloromethane. The organic layers are dried over Na2SO4 and concentrated to yield the crude product, which is purified by chromatography on silica gel (ethyl acetate/dichloromethane).

MS (M+1): 326

Characteristic 1H NMR (300 MHz, dDMSO) signals: 10.0 ppm (s, 1H); 9.1 ppm (s, 1H); 8.2 ppm (s, 1H), 6.0 ppm (d, 1H) 5.4 ppm (d, 1H), Step 2: 6-phenyl-7-(4-{[4-(5-pyridin-2-yl-1H-1,2,4-triazol-3-yl)piperidin-1-yl]methyl}phenyl)-3-vinylimidazo[1,2-a]pyrimidine 0.12 ml triethylamine is added to a solution of 120 mg of the product of reaction 1 in 3 ml methanol. To this solution a solution of 134 mg 2-(5-Piperidin-[1,2,4]triazol-3-yl)-pyridine*2HCl in 5 ml DMF is added, followed by 0.055 ml glacial acetic acid and 157 mg NaBH(OAc)$_3$. The resulting mixture is stirred at room temperature. Additional portions of 2 equivalents NaBH(OAc)$_3$ are added after 1, 2, 3.5, 5 and 20 hours.

The solvent is removed by evaporation after 24 h and the residue is purified by chromatography on silica gel (dichloromethane/methanol) to yield the desired compound.

Characteristic 1H NMR (400 MHz, dDMSO) signals: 9.0 ppm (s, 1H); 8.1 ppm (s, 1H); 5.9 ppm (d, 1H); 5.3 ppm (d, 1H); 3.5 ppm (s, 2H)

MS (M+1): 539

Example 16

Ethyl 6-phenyl-7-(4-{[4-(5-pyridin-2-yl-1,2,4-triazol-3-yl)piperidin-1-yl]methyl}phenyl)imidazo[1,2-a]pyrimidine-2-carboxylate Step 1: 1-[4-(dimethoxymethyl)phenyl]-2-phenylethanol A mixture of Mg turnings 2.4 g (0.1 mol) and 2 ml 1-bromo-4-(dimethoxymethyl)benze (0.012 mol) in THF (10 ml) is heated under nitrogen atmosphere over until the reaction starts. Subsequently additional 1-bromo-4-(dimethoxymethyl)benze 14.71 ml (0.088 mol) dissolved in 30 ml THF is added slowly and the reaction refluxed for 1 h mixture to complete formation of the Gringnard reagent. A solution of 11.70 ml phenylacetaldehyde (0.1 mol) in 100 ml THF is added at to 0° C. and the reaction refluxed for 2 h upon completion of the addition. The mixture is worked up by pouring into saturated aqueous NH4Cl and extraction with ethyl acetate. The combined organic layers are washed with brine, dried over $MgSO_4$ and the solvents evaporated under reduced pressure. The brown-black oily product is used for the next step without purification.

Step 2: 1-[4-(dimethoxymethyl)phenyl]-2-phenylethanone 29.16 g (0.183 mol) sulfur trioxide pyridine complex is added in portions to a solution of 33 g 1-[4-(dimethoxymethyl)phenyl]-2-phenylethanol in dichlormethan (540 ml), DMSO (140 ml) and triethylamine (25.5 ml) at 10° C. The mixture is slowly warmed to room temperature and stirred for 2 h. Water is added and the organic phase is separated, washed with 1 mol/l HCl, 3 times with 5% w/w sodium thiosulfate solution and saturated NaCl solution. The combined organic phases are dried over sodium sulfate and the solvens is evaporated. The residue is purified on a silica gel column chromatography (n-Hexan/EtOAc) to yield the desired product.

MS (M+1): 271

Characteristic 1H NMR (300 MHz, dDMSO) signals: 8.1 ppm (d, 2H); 7.6 ppm (d, 2H); 5.4 ppm (s, 1H), 4.3 ppm (s, 2H)

Step 3: 1-[4-(dimethoxymethyl)phenyl]-3-(dimethylamino)-2-phenylprop-2-en-1-one 5 g 1-[4-(dimethoxymethyl)phenyl]-2-phenylethanone and 4.43 g N,N-dimethylformamid dimethylacetal are stirred for 18 h at 100° C. in DMF. The solvent is removed and the crude product used without further purification.

MS (M+1): 326.

Step 4: 4-[4-(dimethoxymethyl)phenyl]-5-phenylpyrimidin-2-amine 5 g of the product of step 1 and 3 g guanidine hydrochloride are dissolved in 100 ml methanol and 2.7 g of NaOMe is added. The mixture is heated to reflux for 17 h. The product is precipitated upon dilution of the mixture with water and is collected by filtration and washed twice with water.

MS (M+1): 322

Step 5: Ethyl 7-(4-formylphenyl)-6-phenylimidazo[1,2-a]pyrimidine-2-carboxylate 200 mg of the product of step 2 are suspended in 5 ml EtOH and 183 mg of ethyl 3-bromo-2-oxopropanoate is added and the solution stirred under reflux for 5 h. The solvents is evaporated, the residue is suspended in a mixture of water and isopropanol, stirred for 24 h and finally collected by filtration. This material (118 mg) is used for the next step without further purification.

MS (M+1): 372

Step 6: Ethyl 6-phenyl-7-(4-{[4-(5-pyridin-2-yl-1,2,4-triazol-3-yl)piperidin-1-yl]methyl}phenyl)imidazo[1,2-a]pyrimidine-2-carboxylate 0.1 ml triethylamine is added to a solution of 110 mg of the product of step 3 in 5 ml methanol. To this solution a solution of 108 mg 2-(5-Piperidin-[1,2,4]triazol-3-yl)pyridine*2HCl in 5 ml DMF is added, followed by 0.045 ml glacial acetic acid and 127 mg NaBH(OAc)$_3$. The resulting mixture is stirred at room temperature. Additional portions of 2 equivalents NaBH(OAc)$_3$ are added after 1.5 and 4 hours. The solvent is removed by evaporation after 5 h and the residue is purified by chromatography on silica gel (dichloromethane/methanol) to yield the desired compound.

MS (M+1): 585

Characteristic 1H NMR (400 MHz, dDMSO) signals: 9 ppm (s, 1H), 8.4 ppm (s, 1H), 1.4 ppm (t, 3H)

Example 17

2-ethyl-6-phenyl-7-(4-{[4-(5-pyridin-2-yl-1,2,4-triazol-3-yl)piperidin-1-yl]methyl}phenyl)imidazo[1,2-a]pyrimidine This compound is prepared in a manner according to example 16 by using 1-bromobutan-2-one instead of ethyl 3-bromo-2-oxopropanoate in step 5.

MS (M+1): 541

Characteristic 1H NMR (dDMSO, 400 MHz) signals: 9.0 pm (s, 1H); 7.7 ppm (s, 1H), 1.2 ppm (t, 3H)

Example 18

6-phenyl-7-(4-{[4-(5-pyrimidin-2-yl-1,2,4-triazol-3-yl)piperidin-1-yl]methyl}phenyl)imidazo[1,2-a]pyrimidine Example 18 is synthesized in a manner according to example 1 by using 2-(3-piperidin-4-yl-1H-1,2,4-triazol-5-yl)pyrimidine instead of 2-(5-Piperidin-[1,2,4]triazol-3-yl)-pyridine, which is synthesized from tert-butyl 4-(hydrazinocarbonyl)piperidine-1-carboxylate and pyrimidine-2-carbonitrile according to a procedure described in U.S. Pat. No. 4,011,218 or WO2005100344.

MS (M+1): 514

Characteristic 1H NMR (dDMSO, 400 MHz) signals: 9.0 pm (s, 1H); 7.9 ppm (d, 1H)); 7.7 ppm (d, 1H), 3.5 ppm (s, 2H)

Example 19

6-phenyl-5-(4-{[4-(5-pyridin-2-yl-1,2,4-triazol-3-yl)piperidin-1-yl]methyl}phenyl)pyrazolo[1,5-a]pyrimidine Step 1: 6-phenylpyrazolo[1,5-a]pyrimidine-5,7-diol A solution of 9 g 3-amino pyrazole and 25.6 g diethyl phenylmalonate in N,N-dibutylbutan-1-amine is stirred at 185° C. over night. The reaction mixture consists of two layers after cooling to room temperature. The top layer is removed and the lower layer is diluted with dichloromethane and methanol. The resulting solution is concentrated and extracted with a mixture of diethyl ether and 10% w/w NaOH solution. The organic layer is discarded and aqueous layer acidified with concentrated HCl. The precipitated product is collected by filtration.

MS (M+1): 228

Characteristic 1H NMR (dDMSO, 400 MHz) signals: 7.9 ppm (d, 1H),

Step 2: 5,7-dichloro-6-phenylpyrazolo[1,5-a]pyrimidine 3 g 6-phenylpyrazolo[1,5-a]pyrimidine-5,7-diol is suspended in 6 ml POCl$_3$ and the mixture is stirred for 20 h at 100° C. for 2 h. The solvent is removed, the residue is dissolved in a mixture of dichloromethane, water and ice, the organic phase is separated and water-phase is extracted with dichloromethane. The combined dichloromethane phase is dried over Na$_2$SO$_4$ and evaporated yielding the crude product, which is purified by column chromatography on silica gel (dichloromethane/methanol).

MS (M+1): 264

Characteristic 1H NMR (dDMSO, 300 MHz) signals: 8.4 ppm (d, 1H), 6.9 ppm (d, 1H), Step 3: 5-chloro-6-phenylpyrazolo[1,5-a]pyrimidine A mixture of 1 g 5,7-dichloro-6-phenylpyrazolo[1,5-a]pyrimidine, 0.5 ml glacial acetic acid, 1 ml methanol, 6 ml THF and 730 mg of Zn/Cu pair are stirred for 3 h at 50° C. The mixture is filtered through celite, evaporated to dryness and the residue is purified on silica gel (hexanes/ethyl acetate) to yield 550 mg of a 1:1 mixture of the desired product and the starting material, which was used without further purification.

MS (M+1): 230

Step 4: 4-(6-phenylpyrazolo[1,5-a]pyrimidin-5-yl)benzaldehyde

To a mixture of 300 mg of the mixture from step 3 and 360 mg 4-formylphenylboronic acid in 9 ml 1,2-dimethoxyethane are added 1.8 ml of a 10% w/w sodium carbonate solution and 36 mg dichloro[1,1'-bis(diphenylphosphino)ferrocene]palladium (II) and the resulting mixture is heated to 80° C. under an inert gas atmosphere for 18 h. The work up is performed by diluting the reaction mixture with water and dichloromethane, separating the phases and extraction of the aqueous phase with dichloromethane. The combined organic layers are dried over sodium sulphate, evaporated and the residue is purified by chromatography on silica gel (dichloromethane/methanol). The product is crystallized from ethyl acetate.

MS (M+1): 300

Characteristic 1H NMR (300 MHz, dDMSO) signals: 10 ppm (s, 1H), 9.2 ppm (s, 1H); 8.3 ppm (m, 1H)

Step 5: 6-phenyl-5-(4-{[4-(5-pyridin-2-yl-1H-1,2,4-triazol-3-yl)piperidin-1-yl]methyl}phenyl)pyrazolo[1,5-a]pyrimidine 0.2 ml triethylamine is added to a solution of 140 mg 4-(6-phenylpyrazolo[1,5-a]pyrimidin-5-yl)benzaldehyde in 7 ml methanol. To this solution a solution of 170 mg 2-(5-Piperidin-[1,2,4]triazol-3-yl)-pyridine*2HCl in 7 ml DMF is added, followed by 0.25 ml glacial acetic acid and 200 mg NaBH(OAc)$_3$. The resulting mixture is stirred at room temperature. Three additional portions of 2 equivalents NaBH(OAc)$_3$ are added after 2, 4 and 20 hours.

The solvens is removed by evaporation after 24 h and the residue is purified by chromatography on silica gel (dichlormethan/methanol) and by reversed phase HPLC (Water, 10 mM NH$_4$COOH, pH 3.7/ACN) to yield the desired product.

MS (M+1): 513

Characteristic 1H NMR (dDMSO, 400 MHz) signals: 9.2 ppm (s, 1H); 8.7 ppm (d, 1H)); 6.8 ppm (d, 1H), 3.5 ppm (s, 2H)

Step 6: 6-phenyl-5-(4-{[4-(5-pyridin-2-yl-1H-1,2,4-triazol-3-yl)piperidin-1-yl]methyl}phenyl)pyrazolo[1,5-a]pyrimidine hydrochloride The hydrochloride can be obtained by adding a hydrochloric acid solution (5.84N in methanol) to a methanolic solution of 6-phenyl-5-(4-{[4-(5-pyridin-2-yl-1H-1,2,4-triazol-3-yl)piperidin-1-yl]methyl}phenyl)pyrazolo[1,5-a]pyrimidine, stirring at room temperature for at least 1 hour and removing the solvent from the solid product.

Example 20

6-phenyl-7-(4-{[4-(4-pyridin-2-yl-imidazol-1-yl)piperidin-1-yl]methyl}phenyl)imidazo[1,2-a]pyrimidine This compound is prepared in a manner according to example 1.

MS (M+1): 512

Characteristic 1H NMR (dDMSO, 400 MHz) signals: 9.0 ppm (s, 1H); 8.5 ppm (d, 1H); 7.9 ppm (d, 1H); 4.1 ppm (m, 1H); 3.5 ppm (s, 2H)

Example 21

6-phenyl-7-(4-{[4-(5-pyrazin-2-yl-1,2,4-triazol-3-yl)piperidin-1-yl]methyl}phenyl)imidazo[1,2-a]pyrimidine Example 21 is synthesized in a manner according to example 1 by using 2-(3-piperidin-4-yl-1H-1,2,4-triazol-5-yl)pyrazine instead of 2-(5-Piperidin-[1,2,4]triazol-3-yl)-pyridine, which is synthesized from tert-butyl 4-(hydrazinocarbonyl)piperidine-1-carboxylate and pyrazine-2-carbonitrile according to a procedure described in U.S. Pat. No. 4,011,218 or WO2005100344.

MS (M+1): 514

Characteristic 1H NMR (dDMSO, 400 MHz) signals: 9.2 ppm (s, 1H); 9.0 ppm (s, 1H); 7.9 ppm (d, 1H); 7.7 ppm (d, 1H); 3.5 ppm (s, 2H)

Example 22

3-ethyl-6-phenyl-7-(4-{[4-(5-pyridin-2-yl-1,2,4-triazol-3-yl)piperidin-1-yl]methyl}phenyl)imidazo[1,2-a]pyrimidine Step 1: 4-(3-ethyl-6-phenylimidazo[1,2-a]pyrimidin-7-yl)benzaldehyde 100 mg 4-(6-phenyl-3-vinylimidazo[1,2-a]pyrimidin-7-yl)benzaldehyde (prepared as described under example 15 are dissolved in a mixture of 5 ml THF and 5 ml EtOH. 10 mg 10% Pd/C are added and the mixture stirred under an atmosphere of hydrogen for 2 h. The mixture is filtered of celite, the solvens is evaporated and the crude product is purified by chromatography on silica gel (dichloromethane/methanol).

MS (M+1): 328

Characteristic 1H NMR (dDMSO, 400 MHz) signals: 10.0 ppm (s, 1H); 8.8 ppm (s, 1H); 7.7 ppm (s, 1H); 3.0 ppm (qu, 2H); 1.3 ppm (t, 3H)

Step 2: 3-ethyl-6-phenyl-7-(4-{[4-(5-pyridin-2-yl-1,2,4-triazol-3-yl)piperidin-1-yl]methyl}phenyl)imidazo[1,2-a]pyrimidine 0.15 ml triethylamine is added to a solution of 150 mg 4-(3-ethyl-6-phenylimidazo[1,2-a]pyrimidin-7-yl)benzaldehyde in 3 ml methanol. To this solution a solution of 160 mg 2-(5-Piperidin-[1,2,4]triazol-3-yl)-pyridine*2HCl in 3 ml DMF is added, followed by 0.07 ml glacial acetic acid and 195 mg NaBH(OAc)$_3$. The resulting mixture is stirred at room temperature. Three additional portions of 2 equivalents NaBH(OAc)$_3$ are added after 6 hours.

The solvens is removed by evaporation after 20 h and the residue is purified by chromatography on silica gel (dichlormethan/methanol).

MS (M+1): 541

Characteristic 1H NMR (dDMSO, 400 MHz) signals: 8.7 ppm (s, 1H); 7.6 ppm (s, 1H); 3.5 ppm (s, 2H); 3.0 ppm (q, 2H); 1.3 ppm (t, 3H)

Example 23

6-phenyl-7-(4-{1-[4-(5-pyridin-2-yl-1H-1,2,4-triazol-3-yl)piperidin-1-yl]ethyl}phenyl)imidazo[1,2-a]pyrimidine (racemic mixture)

Step 1: 1-[4-(6-phenylimidazo[1,2-a]pyrimidin-7-yl)phenyl]ethanol (racemic mixture)

100 mg 4-(6-phenylimidazo[1,2-a]pyrimidin-7-yl)benzaldehyde (prepared as described for example 1) are dissolved in 2 ml THF and 1 ml of a 2M solution of MeZnCl is added. The mixture is heated (100° C., microwave) for 2 h, cooled to room temperature and extracted with a mixture of dichloromethane and water. The organic layers are dried over sodium sulphate and the solvent is evaporated.

The crude product is purified by chromatography on silica gel (dichloromethane/ethyl acetate)

MS (M+1): 316

Characteristic 1H NMR (dDMSO, 300 MHz) signals: 9.0 ppm (s, 1H); 7.9 ppm (d, 1H); 7.8 ppm (d, 1H); 4.7 ppm (m, 1H), 1.2 ppm (d, 3H)

Step 2: 7-[4-(1-bromoethyl)phenyl]-6-phenylimidazo[1,2-a]pyrimidine (racemic mixture)

100 mg of the product of step 1 are dissolved in dichloromethane, cooled to 0° C. and 86 mg PBr$_3$ are added. The mixture is stirred at room temperature for 24 h. Ice is added, the mixture extracted with dichloromethane and water, the organic layer are dried over Na$_2$SO$_4$ and the solvent is evaporated.

The crude product is used without further purification.

MS (M+1): 378/380

Step 3: 6-phenyl-7-(4-{1-[4-(5-pyridin-2-yl-1H-1,2,4-triazol-3-yl)piperidin-1-yl]ethyl}phenyl)imidazo[1,2-a]pyrimidine (racemic mixture)

To a solution of 0.2 g 2-(5-Piperidin-[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 7 ml DMF are added 120 mg of the product obtained in step 2 dissolved in 1 ml methanol and the mixture is stirred for 20 h. The mixture is concentrated and the crude product is purified by reversed phase HPLC (Water, 10 mM NH$_4$COOH, pH 3.7/ACN)

MS (M+1): 527

Characteristic 1H NMR (dDMSO, 400 MHz) signals: 7.8 ppm (d, 1H); 8.0 ppm (d, 1H); 3.5 ppm (m, 1H); 1.3 ppm (d, 3H)

Step 4: 6-phenyl-7-(4-{1-[4-(5-pyridin-2-yl-1H-1,2,4-triazol-3-yl)piperidin-1-yl]ethyl}phenyl)imidazo[1,2-a]pyrimidine with (E)-butendioic acid The butenoate can be obtained by adding to a solution of 6-phenyl-7-(4-{1-[4-(5-pyridin-2-yl-1H-1,2,4-triazol-3-yl)piperidin-1-yl]ethyl}phenyl)imidazo[1,2-a]pyrimidine in acetone an adequate amount of (E)-butendioic acid as a solid. After stirring the mixture at room temperature for 5-24 h the product can be isolated via filtration and dried.

Example 24

3-fluoro-6-phenyl-7-(4-{[4-(5-pyrazin-2-yl-1,2,4-triazol-3-yl)piperidin-1-yl]methyl}phenyl)imidazo[1,2-a]pyrimidine Example 24 is synthesized in a manner according to example 9 by using 2-(3-piperidin-4-yl-1H-1,2,4-triazol-5-yl)pyrazine instead of 2-(5-Piperidin-[1,2,4]triazol-3-yl)-pyridine, which is synthesized from tert-butyl 4-(hydrazinocarbonyl)piperidine-1-carboxylate and pyrazine-2-carbonitrile according to a procedure described in U.S. Pat. No. 4,011,218 or WO2005100344.

MS (M+1): 532

Characteristic 1H NMR (dDMSO, 400 MHz) signals: 9.2 ppm (s, 1H); 8.8 ppm (s, 1H), 7.6 ppm (d, 1H), 3.5 ppm (s, 2H)

Example 25

3-fluoro-6-phenyl-7-(4-{[4-(5-pyrimidin-2-yl-1H-1,2,4-triazol-3-yl)piperidin-1-yl]methyl}phenyl)imidazo[1,2-a]pyrimidine Example 25 is synthesized in a manner according to example 9 by using 2-(3-piperidin-4-yl-1H-1,2,4-triazol-5-yl)pyrimidine instead of 2-(5-Piperidin-[1,2,4]triazol-3-yl)- pyridine, which is synthesized from tert-butyl 4-(hydrazinocarbonyl)piperidine-1-carboxylate and pyrimidine-2-carbonitrile according to a procedure described in U.S. Pat. No. 4,011,218 or WO2005100344.

MS (M+1): 532

Characteristic 1H NMR (dDMSO, 400 MHz) signals: 8.8 ppm (s, 1H), 7.6 ppm (d, 1H), 3.5 ppm (s, 2H)

Example 26

6-phenyl-7-(4-{[4-(5-pyridin-2-yl-1H-1,2,4-triazol-3-yl)piperidin-1-yl]methyl}phenyl)-2-(trifluoromethyl)imidazo[1,2-a]pyrimidine This compound is prepared in a manner according to example 16 by using 3-bromo-1,1,1-trifluoroacetone instead of ethyl 3-bromo-2-oxopropanoate in step 5.

MS (M+1): 581

Characteristic 1H NMR (dDMSO, 400 MHz) signals: 9.0 ppm (s, 1H); 8.4 ppm (s, 1H); 3.5 ppm (s, 2H);

Example 27

5-methyl-6-phenyl-7-(4-{[4-(5-pyridin-2-yl-1H-1,2,4-triazol-3-yl)piperidin-1-yl]methyl}phenyl)imidazo[1,2-a]pyrimidine Step 1:
5-methyl-6-phenylimidazo[1,2-a]pyrimidin-7-ol A solution of 3.8 g 1,2,4-triazol-3-amine and 6 g ethyl 3-oxo-2-phenylbutanoate is suspended in a mixture of 32 ml DMF and 32 ml N,N-dibutylbutan-1-amine and heated by microwave irradiation to 180° C. for 10 h. The reaction mixture is diluted with water and dichloromethane, the phases separated, the aqueous layer extracted twice with dichloromethane, the combined organic layers are dried over Na2SO4 and concentrated to give the crude product. The crude product is purified by column chromatography (silica gel, dichloromethane/methanol).

MS (M+1): 226

Characteristic 1H NMR (dDMSO, 400 MHz) signals: 7.1 ppm (d, 1H); 2.3 ppm (s, 3H)

Step 2:
7-chloro-5-methyl-6-phenylimidazo[1,2-a]pyrimidine 250 mg of the product of step 1 and 10 ml POCl$_3$ are heated to 100° C. for 1 h. The excess POCl$_3$ is removed by distillation and the residue is treated with ice and diluted with dichloromethane. The phases are separated, the aqueous layer is extracted twice with dichloromethane, the combined organic layers are dried over Na$_2$SO$_4$ and concentrated to give the crude product.

MS (M+1): 244

Characteristic 1H NMR (dDMSO, 300 MHz) signals: 8.4 ppm (d, 1H); 8.3 ppm (d, 1H); 2.6 ppm (s, 3H)

Step 3: 4-(5-methyl-6-phenylimidazo[1,2-a]pyrimidin-7-yl)benzaldehyde

To a mixture of 220 mg of the product obtained in step 2 and 131 mg 4-formylphenylboronic acid in 10 ml 1,2-dimethoxyethane are added 25 mg dichloro[1,1'-bis(diphenylphosphino)ferrocene]palladium (II) dichloromethane adduct and 7 ml of a 10% w/w sodium carbonate solution and the resulting mixture is heated to 120° C. by micro wave irradiation under an inert gas atmosphere for 1 h. The work up is performed by diluting the reaction mixture with water and dichloromethane, separating the phases and extraction of the aqueous phase with dichloromethane. The combined organic layers are dried over sodium sulphate and evaporated. The crude product is purified by silica gel chromatography (dichloromethane/methanol).

MS (M+1): 314

Characteristic 1H NMR (dDMSO, 300 MHz) signals: 10.0 ppm (s, 1H); 8.1 ppm (d, 1H); 7.8 ppm (d, 2H); 7.5 ppm (d, 2H); 2.6 ppm (s, 3H)

Step 4: 5-methyl-6-phenyl-7-(4-{[4-(5-pyridin-2-yl-1H-1,2,4-triazol-3-yl)piperidin-1-yl]methyl}phenyl)imidazo[1,2-a]pyrimidine 0.11 ml triethylamine is added to a solution of 105 mg of the product of step 3 in 5 ml methanol. To this solution a solution of 0.122 g 2-(5-Piperidin-[1,2,4]triazol-3-yl)pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 5 ml DMF is added, followed by 0.05 ml glacial acetic acid and 144 mg NaBH(OAc)$_3$. The resulting mixture is stirred at room temperature. Three additional portions of 2 equivalents NaBH(OAc)$_3$ are added after 2, 4, 6 and 7 hours.

The solvent is removed by evaporation after 9 h and the residue is purified by chromatography on silica gel (dichloromethane/methanol) to yield the desired product.

MS (M+1): 527

Characteristic 1H NMR (dDMSO, 400 MHz) signals: 8.1 ppm (d, 1H); 7.8 ppm (d, 1H); 3.5 ppm (s, 2H); 2.5 ppm (s, 3H)

Step 5: 5-methyl-6-phenyl-7-(4-{[4-(5-pyridin-2-yl-1H-1,2,4-triazol-3-yl)piperidin-1-yl]methyl}phenyl)imidazo[1,2-a]pyrimidine with 2,3-dihydroxybutanedioic acid The product can be obtained by adding to a solution of 5-methyl-6-phenyl-7-(4-{[4-(5-pyridin-2-yl-1H-1,2,4-triazol-3-yl)piperidin-1-yl]methyl}phenyl)imidazo[1,2-a]pyrimidine in methanol an adequate amount of 2,3-dihydroxybutanedioic acid. After stirring of the mixture for 5-24 h the product can be obtained by filtration and drying.

Example 28

2-Isopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine Step 1: 2-Isopropyl-6-phenyl[1,2,4]triazolo[1,5-a]pyrimidine-5,7-diol A solution of 5.00 g 3-amino-5-isopropyl-1,2,4-triazol and 11.24 g diethyl phenylmalonate in 18 ml N,N-dibutylbutan-1-amine is stirred at 185° C. over night. The solution is diluted with 20% w/w NaOH solution, the resulting mixture is stirred for 30 min. The aqueous layer is washed with diethylether, acidified at 0° C. with concentrated HCl until precipitation of the product is complete. The precipitate is collected by filtration to yield the product, which is used without further purification.

MS (M+1): 271
Characteristic 1H NMR (300 MHz, dDMSO) signals: 3.1 (s, 1H); 1.3 (d, 6H)

Step 2: 5,7-Dichloro-2-isopropyl-6-phenyl[1,2,4]triazolo[1,5-a]pyrimidine 6.1 g 2-isopropyl-6-phenyl[1,2,4]triazolo[1,5-a]pyrimidine-5,7-diol is suspended in 13 ml POCl₃. 4.20 g N,N-dimethylaniline is added and the mixture is stirred at 100° C. for 2 h. The solvent is removed and the residue is treated with ice and water until precipitation of the product. The precipitate is collected by filtration to yield the product, which is used without further purification MS (M+1): 307
Characteristic 1H NMR (200 MHz, dDMSO) signals: 7.6 ppm (m, 3H); 7.4 ppm (m, 2H); 1.4 ppm (d, 6H)

Step 3: 5-Chloro-2-isopropyl-6-phenyl[1,2,4]triazolo[1,5-a]pyrimidine 6.00 g 5,7-dichloro-2-isopropyl-6-phenyl[1,2,4]triazolo[1,5-a]pyrimidine is dissolved in 360 ml dichloromethane. 360 ml brine, 120 ml ammonia solution 25% w/w and 6.00 g zinc powder are added and the mixture is stirred at room temperature for 3 h. The reaction mixture is filtrated over kieselgur and is washed with dichloromethane and water. The organic phase is separated and the water phase is extracted with dichloromethane. The combined dichloromethane phase is dried over Na₂SO₄ and evaporated. The crude product contains 5,7-dichloro-2-isopropyl-6-phenyl[1,2,4]triazolo[1,5-a]pyrimidine. The crude product is dissolved again in dichloromethane. 360 ml brine, 120 ml ammonia solution 25% w/w and 6.00 g zinc powder are added and the mixture is stirred at room temperature for 2 h. The reaction mixture is filtrated over kieselgur and washed with dichloromethane and water. The organic phase is separated and the water phase is extracted with dichloromethane. The combined organic layers are dried over sodium sulphate and the solvent is evaporated. The product is used without further purification.

MS (M+1): 273
Characteristic 1H NMR (300 MHz, dDMSO) signals: 9.5 ppm (s, 1H); 1.4 ppm (d, 6H)

Step 4: 4-(2-Isopropyl-6-phenyl[1,2,4]triazolo[1,5-a]pyrimidin-5-yl)benzaldehyde To a mixture of 5.30 g 5-chloro-2-isopropyl-6-phenyl[1,2,4]triazolo[1,5-a]pyrimidine and 3.80 g 4-formylphenylboronic acid in 160 ml 1,2-dimethoxyethane are added 33 ml of a 10% w/w sodium carbonate solution and 0.71 g dichloro[1,1'-bis(diphenylphosphino)ferrocene]palladium (II) and the resulting mixture is heated to 90° C. under an inert gas atmosphere for 18 h. The work up is performed by diluting the reaction mixture with water and dichloromethane, separating the phases and extraction of the aqueous phase with dichloromethane. The combined organic layers are dried over sodium sulphate, the solvent is evaporated and the residue suspended in ethyl acetate. The insoluble solid is filtered and the filtrate is evaporated. The residue is purified by chromatography on silica gel (dichloromethane/ethyl acetate) to yield the product.

MS (M+1): 343
Characteristic 1H NMR (300 MHz, dDMSO) signals: 10 ppm (s, 1H); 9.5 ppm (s, 1H); 1.4 ppm (d, 6H)

Step 5: 2-Isopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine 2.2 ml triethylamine is added to a solution of 1.90 g 2-(5-piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 140 ml methanol. To this solution a solution of 2.30 g 4-(2-isopropyl-6-phenyl[1,2,4]triazolo[1,5-a]pyrimidin-5-yl)benzaldehyde in 140 ml DMF is added, followed by 2.4 ml glacial acetic acid and 3.0 g NaBH(OAc)₃. The resulting mixture is stirred at room temperature. Four additional portions of 2 equivalents NaBH(OAc)₃ are added after 2, 4, 5 and 8 hours. The solvent is removed by evaporation after 20 h and the residue is purified by chromatography on silica gel (dichloromethane/[dichloromethane+7M NH₃ in methanol]) to yield the product.

MS (M+1): 556
Characteristic 1H NMR (400 MHz, dDMSO) signals: 9.4 ppm (s, 1H); 3.5 ppm (s, 2H); 1.4 ppm (d, 6H)

Step 6: 2-Isopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine with 2-hydroxypropane.1,2,3-tricarboxylic acid The product can be obtained by adding to a solution of 2-Isopropyl-6-phenyl-5-(4-{[4-(5-pyridin-2-yl-1H-1,2,4-triazol-3-yl)piperidin-1-yl]methyl}phenyl)[1,2,4]triazolo-[1,5-a]pyrimidine in acetone an adequate amount of 2-hydroxypropane.1,2,3-tricarboxylic acid as a solid. After stirring the mixture for 5-24 h the product can be filtered and dried.

Example 29

7-Methoxy-6-phenyl-5-(4-{[4-(5-pyridin-2-yl-1H-1,2,4-triazol-3-yl)piperidin-1-yl]methyl}phenyl)pyrazolo[1,5-a]pyrimidine

Step 1: 5-Chloro-7-methoxy-6-phenylpyrazolo[1,5-a]pyrimidine 1.00 g 5,7-dichloro-6-phenylpyrazolo[1,5-a]pyrimidine (prepared as described under example 19) are dissolved in 20 ml methanol and 20 ml dichlormethane. 1.2 g sodium methylate is added at 0° C. and stirred at room temperature for 2 h. The solution is diluted with water and dichloromethane. The organic phase separated and the water phase is extracted with dichloromethane. The combined organic layers are dried over Na₂SO₄ and the solvent is evaporated. The crude product is used without further purification.

MS (M+1): 260
Characteristic 1H NMR (dDMSO, 400 MHz) signals: 8.3 ppm (d, 1H); 6.7 ppm (d, 1H); 4.1 ppm (s, 3H)

Step 2: 4-(7-Methoxy-6-phenylpyrazolo[1,5-a]pyrimidin-5-yl)benzaldehyde

To a solution of 1.00 g 5-chloro-7-methoxy-6-phenylpyrazolo[1,5-a]pyrimidine and 0.69 g 4-formylphenylboronic acid in 20 ml 1,2-dimethoxyethane are added 7.3 ml of a 10% w/w sodium carbonate solution and 0.14 g dichloro[1,1'-bis(diphenylphosphino)ferrocene]palladium (II). The mixture is heated for 45 min under microwave irradiation to 120° C. This mixture is worked up by diluting with water and extraction with dichloromethane. The organic layers are dried over $Na_2SO_4$ and concentrated to yield the crude product, which is purified by chromatography on silica gel (methanol/dichloromethane).

MS (M+1): 330

Characteristic 1H NMR (300 MHz, dDMSO) signals: 10.0 ppm (s, 1H); 8.3 ppm (d, 1H); 6.7 ppm (d, 1H)

Step 3: 7-Methoxy-6-phenyl-5-(4-{[4-(5-pyridin-2-yl-1H-1,2,4-triazol-3-yl)piperidin-1-yl]methyl}phenyl)pyrazolo[1,5-a]pyrimidine 0.32 ml triethylamine is added to a solution of 0.42 g 2-(5-Piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 10 ml methanol. To this solution a solution of 0.37 g 4-(7-methoxy-6-phenylpyrazolo[1,5-a]pyrimidin-5-yl)benzaldehyde in 10 ml DMF is added, followed by 0.15 ml glacial acetic acid and 0.43 g $NaBH(OAc)_3$. The resulting mixture is stirred at room temperature. Four additional portions of 2 equivalents $NaBH(OAc)_3$ are added after 1, 2, 3 and 7 hours. The solvent is removed by evaporation after 20 h and the residue is purified by chromatography on silica gel (dichloromethane/[dichloromethane+7M $NH_3$ in methanol]) to yield the product.

MS (M+1): 543

Characteristic 1H NMR (dDMSO, 400 MHz) signals: 8.3 ppm (d, 1H); 6.7 ppm (d, 1H); 4.2 ppm (s, 3H); 3.5 ppm (s, 2H)

Example 30

3-Chloro-6-phenyl-5-(4-{[4-(5-pyridin-2-yl-1H-1,2,4-triazol-3-yl)piperidin-1-yl]methyl}phenyl)pyrazolo[1,5-a]pyrimidine Step 1: 4-(3-Chloro-6-phenylpyrazolo[1,5-a]pyrimidin-5-yl)benzaldehyde 0.4 g 6-phenylpyrazolo[1,5-a]pyrimidin-5-yl)benzaldehyde (prepared as described under example 19) and 0.19 g N-chlorosuccinimide are refluxed in 10 ml chloroform for 5 d. The solvent is removed by distillation and the crude product is purified by chromatography on silica gel (dichloromethane/ethyl acetate).

MS (M+1): 334

Characteristic 1H NMR (400 MHz, dDMSO) signals: 10.0 ppm (s, 1H); 9.3 ppm (s, 1H); 8.5 ppm (s, 1H); 7.9 ppm (m, 2H); 7.6 ppm (m, 2H)

Step 2: 3-Chloro-6-phenyl-5-(4-{[4-(5-pyridin-2-yl-1H-1,2,4-triazol-3-yl)piperidin-1-yl]methyl}phenyl)pyrazolo[1,5-a]pyrimidine 0.29 ml triethylamine are added to a solution of 0.33 g 2-(5-Piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 10 ml methanol. To this solution a solution of 0.30 g 4-(3-chloro-6-phenylpyrazolo[1,5-a]pyrimidin-5-yl)benzaldehyde in 10 ml DMF is added, followed by 0.14 ml glacial acetic acid and 0.38 g $NaBH(OAc)_3$. The resulting mixture is stirred at room temperature. Six additional portions of 2 equivalents $NaBH(OAc)_3$ are added every 2 hours.

The solvent is removed by evaporation after 24 h and the residue is purified by chromatography on silica gel (dichloromethane/methanol]) to yield the product. The residue is suspended in methanol. The crystalline product is isolated by filtration yielding the desired product.

MS (M+1): 547

Characteristic 1H NMR (dDMSO, 400 MHz) signals: 9.2 ppm (s, 1H); 8.4 ppm (s, 1H); 3.5 ppm (s, 2H)

Example 31

3-Bromo-6-phenyl-5-(4-{[4-(5-pyridin-2-yl-1H-1,2,4-triazol-3-yl)piperidin-1-yl]methyl}phenyl)pyrazolo[1,5-a]pyrimidine Step 1: 4-(3-Bromo-6-phenylpyrazolo[1,5-a]pyrimidin-5-yl)benzaldehyde 1.0 g 6-phenylpyrazolo[1,5-a]pyrimidin-5-yl)benzaldehyde (prepared as described under example 19) and 0.65 g N-bromosuccinimide are refluxed in 30 ml Chloroform for 5 h. This mixture is worked up by diluting with water and extraction with dichloromethane. The organic layers are dried over $Na_2SO_4$ and concentrated to yield the crude product, which is suspended in ethyl acetate/petrol ether. The solid desired product is isolated by filtration.

MS (M+1): 378/380

Characteristic 1H NMR (400 MHz, dDMSO) signals: 10.0 ppm (s, 1H); 9.3 ppm (s, 1H); 8.5 ppm (s, 1H); 7.9 ppm (m, 2H); 7.6 ppm (m, 2H)

Step 2: 3-Bromo-6-phenyl-5-(4-{[4-(5-pyridin-2-yl-1H-1,2,4-triazol-3-yl)piperidin-1-yl]methyl}phenyl)pyrazolo[1,5-a]pyrimidine 0.29 ml triethylamine is added to a solution of 0.33 g 2-(5-Piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 10 ml methanol. To this solution a solution of 0.34 g 4-(3-Bromo-6-phenylpyrazolo[1,5-a]pyrimidin-5-yl)benzaldehyde in 10 ml DMF is added, followed by 0.14 ml glacial acetic acid and 0.38 g $NaBH(OAc)_3$. The resulting mixture is stirred at room temperature. Fife additional portions of 2 equivalents $NaBH(OAc)_3$ are added every 2 hours. The solvent is removed by evaporation after 24 h and the residue is purified by chromatography on silica gel (dichloromethane/methanol]). The purified product is suspended in methanol and collected by filtration.

MS (M+1): 591/593

Characteristic 1H NMR (dDMSO, 400 MHz) signals: 9.2 ppm (s, 1H); 8.4 ppm (s, 1H); 3.5 ppm (s, 2H)

Step 3: 3-Bromo-6-phenyl-5-(4-{[4-(5-pyridin-2-yl-1H-1,2,4-triazol-3-yl)piperidin-1-yl]methyl}phenyl)pyrazolo[1,5-a]pyrimidine with 4-methylbenzenesulfonic acid The product can be obtained by adding to a solution of 3-Bromo-6-phenyl-5-(4-{[4-(5-pyridin-2-yl-1H-1,2,4-triazol-3-yl]piperidin-1-yl]methyl}phenyl)pyrazolo[1,5-a]pyri-

Example 32

6-Phenyl-5-(4-{[4-(5-pyridin-2-yl-1H-1,2,4-triazol-3-yl)piperidin-1-yl]methyl}phenyl)pyrazolo[1,5-a]pyrimidine-3-carbonitrile Step 1: 5-(4-Formylphenyl)-6-phenylpyrazolo[1,5-a]pyrimidine-3-carbonitrile 400 mg 4-(3-bromo-6-phenylpyrazolo[1,5-a]pyrimidin-5-yl)benzaldehyde (prepared as described under example 31), 7.0 mg zinc powder, 75.0 mg $Zn(CN)_2$ and 39.0 mg dichloride [1,1'-bis(diphenylphosphino)ferrocene]palladium (II) dichloromethane adduct are suspended in 10 ml dimethylacetamide and the mixture is heated for 45 min under microwave irradiation to 160° C. The workup is performed by diluting the mixture with water and dichloromethane, extracting the aqueous layer twice and drying the combined organic layers over $Na_2SO_4$. The compound is isolated by evaporation of the solvent and chromatography on silica gel (dichloromethane/ethyl acetate).

MS (M+1): 325
Characteristic 1H NMR (300 MHz, dDMSO) signals: 10.0 ppm (s, 1H); 9.5 ppm (s, 1H); 8.9 ppm (s, 1H); 7.9 ppm (m, 2H); 7.6 ppm (m, 2H)

Step 2: 6-Phenyl-7-(4-{[4-(5-pyridin-2-yl-1,2,4-triazol-3-yl)piperidin-1-yl]methyl}phenyl)imidazo[1,2-a]pyrimidine-3-carbonitrile 0.12 ml triethylamine is added to a solution of 0.12 g 2-(5-Piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 5 ml methanol. To this solution a solution of 0.13 g 5-(4-Formylphenyl)-6-phenylpyrazolo[1,5-a]pyrimidine-3-carbonitrile in 5 ml DMF is added, followed by 0.06 ml glacial acetic acid and 0.16 g $NaBH(OAc)_3$. The resulting mixture is stirred at room temperature. Additional portions of 2 equivalents $NaBH(OAc)_3$ are added after 1.5, 3, 4, 6 and 8 hours. The solvent is removed by evaporation after 9 h and the residue is purified by chromatography on silica gel (dichloromethane/methanol). The residue is suspended in ammonia solution (7N in methanol). The desired product is isolated by filtration.

MS (M+1): 538
Characteristic 1H NMR (400 MHz, dDMSO) signals: 9.4 ppm (s, 1H); 8.9 ppm (s, 1H); 3.5 ppm (s, 2H)

Example 33

3-Ethynyl-6-phenyl-5-(4-{[4-(5-pyridin-2-yl-1H-1,2,4-triazol-3-yl)piperidin-1-yl]methyl}phenyl)pyrazolo[1,5-a]pyrimidine Step 1: 4-{6-Phenyl-3-[(trimethylsilyl)ethynyl]pyrazolo[1,5-a]pyrimidin-5-yl}benzaldehyde 400 mg 4-(3-bromo-6-phenylpyrazolo[1,5-a]pyrimidin-5-yl)benzaldehyde (prepared as described under example 31), 820 mg trimethyl[(tributylstannyl)ethynyl]silane and 60 mg $Pd(PPh_3)_4$ are suspended in 8 ml toluene under a nitrogen atmosphere. The mixture is heated (microwave irradiation) to 130° C. for 1 h. This mixture is worked up by diluting with water and extraction with dichloromethane. The combined organic layers are dried over $Na_2SO_4$ and concentrated to yield the crude product, which is purified by chromatography on silica gel (ethyl acetate/dichloromethane).

MS (M+1): 396 and 428 [MH⁺+32 (MeOH)]
Characteristic 1H NMR (300 MHz, dDMSO) signals: 10.0 ppm (s, 1H); 9.3 ppm (s, 1H); 8.5 ppm (s, 1H); 7.9 ppm (m, 2H); 7.6 ppm (m, 2H); 0.3 ppm (s, 9H)

Step 2: 6-Phenyl-5-(4-{[4-(5-pyridin-2-yl-1H-1,2,4-triazol-3-yl)piperidin-1-yl]methyl}phenyl)-3-[(trimethylsilyl)ethynyl]pyrazolo[1,5-a]pyrimidine 0.26 ml triethylamine is added to a solution of 0.30 g 2-(5-piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 10 ml methanol. To this solution a solution of 0.33 g 4-{6-phenyl-3-[(trimethylsilyl)ethynyl]pyrazolo[1,5-a]pyrimidin-5-yl}benzaldehyde in 10 ml DMF is added, followed by 0.12 ml glacial acetic acid and 0.35 g $NaBH(OAc)_3$. The resulting mixture is stirred at room temperature. Additional portions of 2 equivalents $NaBH(OAc)_3$ are added after 1.5, 3, 6 and 8 hours. The solvent is removed by evaporation after 22 h and the residue is purified by chromatography on silica gel (dichloromethane/methanol) to yield the desired compound.

MS (M+1): 609
Characteristic 1H NMR (300 MHz, dDMSO) signals: 9.2 ppm (s, 1H); 8.7 ppm (m, 1H); 3.5 ppm (s, 2H); 0.3 ppm (s, 9H)

Step 3: 3-Ethynyl-6-phenyl-5-(4-{[4-(5-pyridin-2-yl-1H-1,2,4-triazol-3-yl)piperidin-1-yl]methyl}phenyl)pyrazolo[1,5-a]pyrimidine 250 mg 6-phenyl-5-(4-{[4-(5-pyridin-2-yl-1H-1,2,4-triazol-3-yl)piperidin-1-yl]methyl}phenyl)-3-[(trimethylsilyl)ethynyl]pyrazolo[1,5-a]pyrimidine and 114 mg $K_2CO_3$ are stirred in 5 ml methanol and 5 ml dichloromethane for 7 h. The solvent is removed by evaporation and the residue is purified by chromatography on silica gel (dichloromethane/methanol) to yield the desired compound MS (M+1): 537
Characteristic 1H NMR (400 MHz, dDMSO) signals: 9.2 ppm (s, 1H); 8.7 ppm (m, 1H); 8.5 ppm (s, 1H); 4.3 ppm (s, 1H); 3.5 ppm (s, 2H)

Example 34

3-Ethyl-6-phenyl-5-(4-{[4-(5-pyridin-2-yl-1H-1,2,4-triazol-3-yl)piperidin-1-yl]methyl}phenyl)pyrazolo[1,5-a]pyrimidine Step 1: 4-(6-Phenyl-3-vinylpyrazolo[1,5-a]pyrimidin-5-yl)benzaldehyde 400 mg 4-(3-bromo-6-phenylpyrazolo[1,5-a]pyrimidin-5-yl)benzaldehyde (prepared as described under example 31), 504 mg tributyl(vinyl)stanane, 176 mg tetraethylammonium chloride, 147 mg $K_2CO_3$ and 19 mg $Pd(PPh_3)_2Cl_2$ are suspended in 10 ml THF under a nitrogen atmosphere. The mixture is heated (microwave irradiation) to 110° C. for 45 min. This mixture is worked up by diluting with water and extraction with dichloromethane. The combined organic layers are dried over $Na_2SO_4$ and concentrated to yield the crude product, which is purified by chromatography on silica gel (ethyl acetate/dichloromethane).

MS (M+1): 326

Characteristic 1H NMR (300 MHz, dDMSO) signals: 10.0 ppm (s, 1H); 9.2 ppm (s, 1H); 8.5 ppm (s, 1H); 7.8 ppm (m, 2H); 7.6 ppm (m, 2H); 6.9 ppm (q, 1H); 6.1 ppm (d, 1H), 5.3 ppm (d, 1H)

Step 2: 4-(3-Ethyl-6-phenylpyrazolo[1,5-a]pyrimidin-5-yl)benzaldehyde 275 mg 4-(6-phenyl-3-vinylpyrazolo[1,5-a]pyrimidin-5-yl)benzaldehyde is dissolved in 10 ml THF and 10 ml ethanol. Pd/C (10% w/w) is added and stirred under $H_2$-atmosphere at room temperature for 1.5 h. The mixture is filtrated over kieselgur. The filtrate is concentrated and the residue is purified by chromatography on silica gel (dichloromethane/ethyl acetate) to yield the desired compound.

MS (M+1): 328

Characteristic 1H NMR (400 MHz, dDMSO) signals: 10.0 ppm (s, 1H); 9.1 ppm (s, 1H); 8.2 ppm (s, 1H); 7.8 ppm (m, 2H); 7.6 ppm (m, 2H); 2.8 ppm (q, 2H); 1.3 ppm (t, 3H)

Step 3: 3-Ethyl-6-phenyl-5-(4-{[4-(5-pyridin-2-yl-1H-1,2,4-triazol-3-yl)piperidin-1-yl]methyl}phenyl)pyrazolo[1,5-a]pyrimidine 0.19 ml triethylamine is added to a solution of 0.22 g 2-(5-piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 5 ml methanol. To this solution a solution of 0.20 g 4-(3-Ethyl-6-phenylpyrazolo[1,5-a]pyrimidin-5-yl)benzaldehyde in 5 ml DMF is added, followed by 0.09 ml glacial acetic acid and 0.26 g $NaBH(OAc)_3$. The resulting mixture is stirred at room temperature. Additional portions of 2 equivalents $NaBH(OAc)_3$ is added after 1, 2, 3, 5 and 8 hours. The solvent is removed by evaporation after 9 h and the residue is purified by chromatography on silica gel (dichloromethane/methanol) to yield the desired compound.

MS (M+1): 541

Characteristic 1H NMR (400 MHz, dDMSO) signals: 9.0 ppm (s, 1H); 8.7 ppm (s, 1H); 3.5 ppm (s, 2H); 1.3 ppm (t, 3H)

Step 4: 3-Ethyl-6-phenyl-5-(4-{[4-(5-pyridin-2-yl-1H-1,2,4-triazol-3-yl)piperidin-1-yl]methyl}phenyl)pyrazolo[1,5-a]pyrimidine with (E)-butenedioic acid The butenoate can be obtained by adding to a solution of 3-Ethyl-6-phenyl-5-(4-{[4-(5-pyridin-2-yl-1H-1,2,4-triazol-3-yl)piperidin-1-yl]methyl}phenyl)pyrazolo[1,5-a]pyrimidine in acetone an adequate amount of (E)-butenedioic acid. After stirring at room temperature for 5-24 h the product can be filtered and dried.

Example 35

7-[4-({4-[5-(4-Methylpyridin-2-yl)-1H-1,2,4-triazol-3-yl]piperidin-1-yl}methyl)phenyl]-6-phenylimidazo[1,2-a]pyrimidine Example 35 is synthesized in a manner according to example 1 by using 4-methyl-2-(3-piperidin-4-yl-1H-1,2,4-triazol-5-yl)pyridine instead of 2-(5-piperidin-[1,2,4]triazol-3-yl)-pyridine, which is synthesized from tert-butyl 4-(hydrazinocarbonyl)piperidine-1-carboxylate and 4-methylpyridine-2-carbonitrile according to a procedure described in U.S. Pat. No. 4,011,218 or WO2005100344.

MS (M+1): 527

Characteristic 1H NMR (dDMSO, 400 MHz) signals: 9.0 ppm (s, 1H); 8.5 ppm (m, 1H); 7.8 ppm (d, 1H); 3.5 ppm (s, 2H); 2.4 ppm (s, 3H)

Example 36

7-[4-({4-[5-(6-Methylpyridin-2-yl)-1H-1,2,4-triazol-3-yl]piperidin-1-yl}methyl)phenyl]-6-phenylimidazo[1,2-a]pyrimidine Example 36 is synthesized in a manner according to example 1 by using 2-methyl-6-(5-piperidin-4-yl-1H-1,2,4-triazol-3-yl)pyridine instead of 2-(5-piperidin-[1,2,4]triazol-3-yl)-pyridine, which is synthesized from tert-butyl 4-(hydrazinocarbonyl)piperidine-1-carboxylate and 6-methylpyridine-2-carbonitrile according to a procedure described in U.S. Pat. No. 4,011,218 or WO2005100344.

MS (M+1): 527

Characteristic 1H NMR (dDMSO, 400 MHz) signals: 9.0 ppm (s, 1H); 7.9 ppm (d, 1H); 3.5 ppm (s, 2H); 2.6 ppm (s, 3H)

Example 37

2-Methyl-6-phenyl-5-(4-{[4-(5-pyridin-2-yl-1,2,4-triazol-3-yl)piperidin-1-yl]methyl}phenyl)[1,2,4]triazolo[1,5-a]pyrimidine

Step 1: 2-methyl-6-phenyl[1,2,4]triazolo[1,5-a]pyrimidine-5,7-diol

A solution of 25.0 g 3-amino-5-methyltriazole and 66.0 ml diethyl phenylmalonate in 100 ml N,N-dibutylbutan-1-amine is stirred at 185° C. for 20 h. The reaction mixture consists of two layers after cooling to room temperature. The top layer is removed and the lower layer is diluted with 10% w/w NaOH solution and water. The aqueous layer is extracted with diethyl ether and acidified with concentrated HCl until precipition of the product is complete. The precipitate is collected by filtration to yield the product, which is used without further purification.

MS (M+1): 243

Characteristic 1H NMR (200 MHz, dDMSO) signals: 7.4 ppm (m, 2H); 7.3 ppm (m, 2H); 7.2 ppm (m, 1H); 2.4 ppm (s, 3H)

Step 2: 5,7-dichloro-2-methyl-6-phenyl[1,2,4]triazolo[1,5-a]pyrimidine 35.0 g 2-methyl-6-phenyl[1,2,4]triazolo[1,5-a]pyrimidine-5,7-diol is suspended in 80 ml $POCl_3$ and 27.47 ml N,N-dimethylaniline are added. The mixture is stirred at 100° C. for 1 h. The excess of $POCl_3$ is removed and the residue is dissolved in a mixture of dichloromethane, water and ice. The organic phase is separated and the water-phase is extracted with dichloromethane. The combined organic layers are dried over $Na_2SO_4$ and the solvent is evaporated. The crude product is used without further purification.

MS (M+1): 279

Step 3: 5-chloro-2-methyl-6-phenyl[1,2,4]triazolo[1,5-a]pyrimidine 34.5 g 5,7-dichloro-2-methyl-6-phenyl[1,2,4]triazolo[1,5-a]pyrimidine is dissolved in 500 ml dichloromethane. 500 ml brine, 250 ml ammonia solution 25% w/w and 34.0 g zinc powder are added and the mixture is stirred at room temperature for 1 h. The reaction mixture is filtrated over kieselgur and is washed with dichloromethane and water. The organic phase is separated and the water phase is extracted with dichloromethane. The combined dichloromethane phase is dried over $Na_2SO_4$ and the solvent is evaporated. The crude product is purified by chromatography on silica gel (dichloromethane/ethyl acetate) to yield the desired compound.

MS (M+1): 245

Characteristic 1H NMR (300 MHz, dDMSO) signals: 9.45 ppm (s, 1H); 2.6 ppm (s, 3H)

Step 4: 4-(2-methyl-6-phenyl[1,2,4]triazolo[1,5-a]pyrimidin-5-yl)benzaldehyde To a mixture of 6.90 g 5-chloro-2-methyl-6-phenyl[1,2,4]triazolo[1,5-a]pyrimidine and 4.65 g 4-formylphenylboronic acid in 100 ml 1,2-dimethoxyethane are added 55 ml of a 10% w/w sodium carbonate solution and 1.03 g dichloro[1,1'-bis(diphenylphosphino)ferrocene]palladium (II). The resulting mixture is heated to 90° C. under an inert gas atmosphere for 18 h. The work up is performed by diluting the reaction mixture with water and dichloromethane, separating the phases and extraction of the aqueous phase with dichloromethane. The combined organic layers are dried over sodium sulphate and the solvent is evaporated. The residue is purified by chromatography on silica gel (dichloromethane/methanol) to yield the desired product.

MS (M+1): 315

Characteristic 1H NMR (300 MHz, dDMSO) signals: 10.0 ppm (s, 1H); 9.4 ppm (s, 1H); 7.8 ppm (m, 2H); 7.6 ppm (m, 2H); 2.6 ppm (s, 3H)

Step 5: 2-Methyl-6-phenyl-5-(4-{[4-(5-pyridin-2-yl-1,2,4-triazol-3-yl)piperidin-1-yl]methyl}phenyl)[1,2,4]triazolo[1,5-a]pyrimidine 8.03 ml triethylamine is added to a solution of 9.13 g 2-(5-piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 150 ml methanol. To this solution a solution of 7.90 g 4-(2-methyl-6-phenyl[1,2,4]triazolo[1,5-a]pyrimidin-5-yl)benzaldehyde in 150 ml DMF is added, followed by 4.14 ml glacial acetic acid and 10.65 g NaBH(OAc)$_3$. The resulting mixture is stirred at room temperature. Five additional portions of 2 equivalents NaBH(OAc)$_3$ are added after 1.5, 2.5, 3.5, 4.5 and 6 hours. The solvent is removed by evaporation after 8 hours and the residue is purified by chromatography on silica gel (dichloromethane/[dichloromethane+7M NH$_3$ in methanol]). The solid residue is suspended in diethylether/methanol (9:1) and stirred at ambient temperature for 18 hours. The desired product is collected by filtration and dried.

MS (M+1): 528

Characteristic 1H NMR (400 MHz, dDMSO) signals: 9.3 ppm (s, 1H); 8.7 ppm (m, 1H) 3.5 ppm (s, 2H); 2.6 ppm (s, 3H)

Step 6: 2-Methyl-6-phenyl-5-(4-{[4-(5-pyridin-2-yl-1,2,4-triazol-3-yl)piperidin-1-yl]methyl}phenyl)[1,2,4]triazolo[1,5-a]pyrimidine with (E)-butenedioic acid To 2.0 g 2-methyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine in 40 ml acetone are added 0.484 g (E)-butenedioic acid. The reaction mixture is stirred at ambient temperature for 18 h. The desired compound is collected by filtration and dried. Characteristic 1H NMR (dDMSO, 400 MHz) signals: 9.3 ppm (s, 1H); 8.7 ppm (m, 1H); 6.6 ppm (s, 2H); 3.5 ppm (s, 2H); 2.6 ppm (s, 3H)

Step 7: Analogously 2-Methyl-6-phenyl-5-(4-{[4-(5-pyridin-2-yl-1,2,4-triazol-3-yl)piperidin-1-yl]methyl}phenyl)[1,2,4]triazolo[1,5-a]pyrimidine with (Z)-butenedioic acid can be obtained.

Step 8: 2-Methyl-6-phenyl-5-(4-{[4-(5-pyridin-2-yl-1,2,4-triazol-3-yl)piperidin-1-yl]methyl}phenyl)[1,2,4]triazolo[1,5-a]pyrimidine with propanedioic acid To 3.0 g 2-methyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine (prepared as described under example 37) in 50 ml acetone is added a solution of 0.725 g propanedioic acid in 10 ml acetone dropwise. The reaction mixture is stirred at ambient temperature for 18 h. The desired compound is collected by filtration and dried.

Characteristic 1H NMR (dDMSO, 400 MHz) signals: 9.4 ppm (s, 1H); 8.7 ppm (m, 1H); 6.0 ppm (s, 2H); 2.6 ppm (s, 3H)

Example 38

3-Methyl-6-phenyl-5-(4-{[4-(5-pyridin-2-yl-1H-1,2,4-triazol-3-yl)piperidin-1-yl]methyl}phenyl)pyrazolo[1,5-a]pyrimidine

Step 1: 4-(3-Methyl-6-phenylpyrazolo[1,5-a]pyrimidin-5-yl)benzaldehyde

To a mixture of 0.50 g 4-(3-bromo-6-phenylpyrazolo[1,5-a]pyrimidin-5-yl)benzaldehyde (prepared as described under example 31) and 0.12 g methylboronic acid in 17 ml toluene are added 0.83 g potassium phosphate tribasic, 0.029 g palladium acetate and 0.11 g S-PHOS. The reaction mixture is heated for 1 h under microwave irradiation to 120° C. This mixture is worked up by diluting with water and extraction with dichloromethane. The organic layers are dried over Na$_2$SO$_4$ and concentrated to yield the crude product, which is purified by chromatography on silica gel (ethyl acetate/dichloromethane).

MS (M+1): 314

Characteristic 1H NMR (300 MHz, dDMSO) signals: 10.0 ppm (s, 1H); 9.1 ppm (s, 1H); 7.8 ppm (m, 2H); 7.6 ppm (m, 2H); 2.4 ppm (s, 3H)

Step 2: 3-Methyl-6-phenyl-5-(4-{[4-(5-pyridin-2-yl-1H-1,2,4-triazol-3-yl)piperidin-1-yl]methyl}phenyl)pyrazolo[1,5-a]pyrimidine 0.36 ml triethylamine is added to a solution of 0.41 g 2-(5-piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 10 ml methanol. To this solution a solution of 0.35 g 4-(3-methyl-6-phenylpyrazolo[1,5-a]pyrimidin-5-yl)benzaldehyde in 10 ml DMF is added, followed by 0.17 ml glacial acetic acid and 0.48 g NaBH(OAc)$_3$. The resulting mixture is stirred at room temperature. Additional portions of 2 equivalents NaBH(OAc)$_3$ are added after 1, 2, 4, 5, 8 and 24 hours. The solvent is removed by evaporation after 27 h and the residue is purified by chromatography on silica gel (dichloromethane/[dichloromethane+7M NH$_3$ in methanol]) to yield the desired compound, witch is precipitated by the addition of methanol.

MS (M+1): 527

Characteristic 1H NMR (300 MHz, dDMSO) signals: 9.0 ppm (s, 1H); 8.6 ppm (m, 1H); 8.1 ppm (s, 1H); 3.5 ppm (s, 2H); 2.4 ppm (s, 3H)

Example 39

2,7-Dimethyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine Step 1: 2,7-Dimethyl-6-phenyl[1,2,4]triazolo[1,5-a]pyrimidin-5-ol A solution of 1.5 g 3-amino-5-methyltriazole and 3.3 g ethyl 3-oxo-2-phenylbutanoate is dissolved in a mixture of 21 ml DMF and 21 ml N,N-dibutylbutan-1-amine and heated by microwave irradiation to 180° C. for 6 h. The reaction mixture forms two phases. The DMF phase is separated and concentrated. The crude product is purified by column chromatography on silica gel (dichloromethane/methanol).

MS (M+1): 241

Characteristic 1H NMR (dDMSO, 300 MHz) signals: 13.0 ppm (m, 1H); 2.3 ppm (m, 6H)

Step 2: 5-Chloro-2,7-dimethyl-6-phenyl[1,2,4]triazolo[1,5-a]pyrimidine 1.34 g of the product of step 1 are suspended in 20 ml POCl$_3$. 1.06 ml N,N-dimethylaniline is added and the mixture is heated to 100° C. for 45 min. The excess of POCl$_3$ is removed by distillation and the residue is treated with ice. The desired product precipitates and is collected by filtration.

MS (M+1): 259

Characteristic 1H NMR (dDMSO, 300 MHz) signals: 7.6 ppm (m, 3H); 7.4 ppm (m, 2H); 2.6 ppm (s, 3H); 2.6 ppm (s, 3H)

Step 3: 4-(2,7-Dimethyl-6-phenyl[1,2,4]triazolo[1,5-a]pyrimidin-5-yl)benzaldehyde To a mixture of 1.25 g 5-chloro-2,7-dimethyl-6-phenyl[1,2,4]triazolo[1,5-a]pyrimidine and 0.87 g 4-formylphenylboronic acid in 25 ml 1,2-dimethoxyethane are added 0.18 g dichloro[1,1'-bis(diphenylphosphino)ferrocene]palladium (II) dichloromethane adduct and 9.30 ml of a 10% w/w sodium carbonate solution. The resulting mixture is heated to 110° C. by microwave irradiation under an inert gas atmosphere for 45 min. The work up is performed by diluting the reaction mixture with water and dichloromethane, separating the phases and extraction of the aqueous phase with dichloromethane. The combined organic layers are dried over sodium sulphate and the solvent is evaporated. The residue is purified by chromatography on silica gel (dichloromethane/methanol). The desired product is suspended in ethyl acetate/petrolether and isolated by filtration.

MS (M+1): 329

Characteristic 1H NMR (dDMSO, 300 MHz) signals: 10.0 ppm (s, 1H); 7.8 ppm (m, 2H); 7.5 ppm (m, 2H); 2.6 ppm (s, 3H); 2.6 ppm (s, 3H)

Step 4: 2,7-Dimethyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine 0.49 ml triethylamine is added to a solution of 0.55 g 2-(5-piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 15 ml methanol. To this solution a solution of 0.50 g 4-(2,7-dimethyl-6-phenyl[1,2,4]triazolo[1,5-a]pyrimidin-5-yl)benzaldehyde in 15 ml DMF is added, followed by 0.23 ml glacial acetic acid and 0.64 g NaBH(OAc)$_3$. The resulting mixture is stirred at room temperature. Additional portions of 2 equivalents NaBH(OAc)$_3$ are added after 1, 2, 3, 5 and 7 h. The solvent is removed by evaporation after 20 h and the residue is purified by chromatography on silica gel (dichloromethane/[dichloromethane+7M NH$_3$ in methanol]) to yield the desired compound.

MS (M+1): 542

Characteristic 1H NMR (300 MHz, dDMSO) signals: 8.7 ppm (m, 1H); 3.5 ppm (m, 1H); 2.6 ppm (s, 3H); 2.6 ppm (s, 3H)

Example 40

2-Ethyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine Step 1: 2-Ethyl-6-phenyl[1,2,4]triazolo[1,5-a]pyrimidine-5,7-diol A solution of 5.00 g 3-amino-5-ethyl-1,2,4-triazole and 15.00 g diethyl phenylmalonate in 18 ml N,N-dibutylbutan-1-amine is stirred at 185° C. over night. The solution is diluted with 5N NaOH solution, the resulting mixture is stirred for 30 min. The aqueous layer is washed with diethylether, acidified at 0° C. with concentrated HCl until precipitation of the product is complete. The precipitate is collected by filtration to yield the product, which is used without further purification.

MS (M+1): 257

Characteristic 1H NMR (300 MHz, dDMSO) signals: 7.4 ppm (m, 2H); 7.3 ppm (m, 2H); 7.1 ppm (m, 1H); 2.8 ppm (q, 2H); 1.3 ppm (t, 3H)

Step 2: 5,7-Dichloro-2-ethyl-6-phenyl[1,2,4]triazolo[1,5-a]pyrimidine 5.7 g 2-ethyl-6-phenyl[1,2,4]triazolo[1,5-a]pyrimidine-5,7-diol is suspended in 12 ml POCl$_3$. 4.30 ml N,N-dimethylanilin is added and the mixture is stirred at 100° C. for 20 h. The solvent is removed, the residue is treated with ice and water until precipitation of the product. The precipitate is collected by filtration to yield the product, which is used without further purification

MS (M+1): 293

Characteristic 1H NMR (300 MHz, dDMSO) signals: 2.9 ppm (q, 2H); 1.4 ppm (t, 3H)

Step 3: 5-Chloro-2-ethyl-6-phenyl[1,2,4]triazolo[1,5-a]pyrimidine 6.00 g 5,7-dichloro-2-ethyl-6-phenyl[1,2,4]triazolo[1,5-a]pyrimidine is dissolved in 180 ml dichloromethane. 180 ml saturated brine, 120 ml ammonia solution 25% w/w and 6.00 g zinc powder are added and the mixture is stirred at room temperature for 3 h. The reaction mixture is filtrated over kieselgur and is washed with dichloromethane and water. The organic phase is separated and the water phase is extracted with dichloromethane. The combined organic layers are dried over $Na_2SO_4$ and the solvent is evaporated. The residue contained 2-ethyl-6-phenyl[1,2,4]triazolo[1,5-a]pyrimidine. This mixture is used without further purification for the next reaction.

MS (M+1): 259

Characteristic 1H NMR (300 MHz, dDMSO) signals: 9.5 ppm (s, 1H); 2.9 ppm (q, 2H); 1.4 ppm (t, 3H)

Step 4: 4-(2-Ethyl-6-phenyl[1,2,4]triazolo[1,5-a]pyrimidin-5-yl)benzaldehyde To a mixture of 3.90 g of the crude product obtained in step 3 and 3.00 g 4-formylphenylboronic acid in 180 ml 1,2-dimethoxyethane are added 0.55 g dichloro[1,1'-bis(diphenylphosphino)ferrocene]palladium (II) and 25 ml of a 10% w/w sodium carbonate solution. The resulting mixture is heated to 90° C. under an inert gas atmosphere for 20 h. The work up is performed by diluting the reaction mixture with water and dichloromethane, separating the phases and extraction of the aqueous phase with dichloromethane. The combined organic layers are dried over sodium sulphate, the solvent is evaporated and the residue is suspended in ethyl acetate. The crude product is isolated by filtration, witch is purified on silica gel (dichloromethane/methanol).

MS (M+1): 329

Characteristic 1H NMR (300 MHz, dDMSO) signals: 10.0 ppm (s, 1H); 9.5 ppm (s, 1H); 2.9 ppm (q, 2H); 1.4 ppm (t, 3H)

Step 5: 2-Ethyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine 3.5 ml triethylamine is added to a solution of 3.51 g 2-(5-piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 100 ml methanol. To this solution a solution of 2.30 g 4-(2-ethyl-6-phenyl[1,2,4]triazolo[1,5-a]pyrimidin-5-yl)benzaldehyde in 100 ml DMF is added, followed by 1.44 ml glacial acetic acid and 4.1 g $NaBH(OAc)_3$. The resulting mixture is stirred at room temperature. Four additional portions of 2 equivalents $NaBH(OAc)_3$ are added after 2, 4.5 and 8 hours. The solvent is removed by evaporation after 20 h and the residue is purified by chromatography on silica gel (dichloromethane/[dichloromethane+7M $NH_3$ in methanol]) to yield the product.

MS (M+1): 542

Characteristic 1H NMR (dDMSO, 400 MHz) signals: 9.3 ppm (s, 1H); 8.6 ppm (m, 1H); 3.5 ppm (s, 2H); 1.4 ppm (t, 3H)

Step 6: 2-Ethyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine with (E)-butenedioic acid The product can be obtained by adding to a solution of 2-Ethyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine in acetone an adequate amount of E)-butenedioic acid. After stirring at room temperature for 5-24 h the product can be filtered and dried.

Example 41

2-Cyclopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine hydrochloride To 8.08 g 2-Cyclopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine (prepared as described under example 4) in 77 ml methanol are added 2.50 ml hydrochloride solution (5.84N in methanol). The mixture is stirred at room temperature for 1 h. The solvent is removed to yield the desired product.

MS (M+1): 554

Characteristic 1H NMR (dDMSO, 300 MHz) signals: 9.3 ppm (s, 1H); 8.7 ppm (m, 1H)

Example 42

2-Methyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine hydrochloride To 8.79 g 2-methyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine (prepared as described under example 37) in 88 ml methanol are added 2.85 ml hydrochloric acid solution (5.84N in methanol). The mixture is stirred at room temperature for 1 h. The solvent is removed to yield the desired product.

MS (M+1): 528

Characteristic 1H NMR (dDMSO, 300 MHz) signals: 9.4 ppm (s, 1H); 8.7 ppm (m, 1H); 2.6 ppm (s, 3H)

Example 43

2-Methyl-6-phenyl-5-[4-({4-[5-(1,3-thiazol-2-yl)-1H-1,2,4-triazol-3-yl]piperidin-1-yl}methyl)phenyl][1,2,4]triazolo[1,5-a]pyrimidine

Step 1: 2-Trimethylsilanyl-thiazole

To a mixture of 40.6 ml n-butyl lithium (1.6M in hexane) and 18 ml diethylether is added dropwise at −70° C. a solution of 5.03 g thiazole dissolved in 59 ml diethylether. After 30 min 6.41 g trimethylsilylchloride dissolved in 59 ml diethylether is added at −70° C. The reaction mixture is stirred at −70° C. for 1 h and allowed to warm up to room temperature. The mixture is washed with saturated $NaHCO_3$ solution, dried over $Na_2SO_4$ and the solvent is evaporated. The residue is distilled, to yield the desired product.

Step 2: Thiazole-2-yl-iminocarbonylhydrazine 10.0 g 2-trimethylsilanyl-thiazole and 11.5 g tolylsulfonylcyanid are stirred at 70° C. for 5 h. The mixture is diluted with THF and 9.83 g hydrazinhydrate is added at 1° C. The reaction mixture is stirred at room temperature over night. The solvent is removed by evaporation and the residue is purified by chromatography on silica gel (dichloromethane/methanol) to yield the desired product.

Step 3: 4-[N'-(imino-thiazol-2-yl-methyl)-hydrazinocarbonyl]-piperidine-1-carboxylic acid tert-butyl ester 8.65 g piperidine-1,4-dicarboxylic acid mono-tert-butyl ester is dissolved in dichloromethane, 6.12 g 1,1-carbonyldiimidazole is added portionwise. 5.45 g thiazole-2-yl-iminocarbonylhydrazine are added slowly and the mixture is stirred at room temperature for 18 hours. The solvent is removed by evaporation and the residue is washed with water. The crude product is dried and used without further purification.

Step 4: 4-(5-Thiazol-2-yl-1H-[1,2,4]triazol-3-yl)-piperidine-1-carboxylic acid tert-butyl ester 8.00 g 4-[N'-(imino-thiazol-2-yl-methyl)-hydrazinocarbonyl]-piperidine-1-carboxylic acid tert-butyl ester is heated to 220° C. The clear melting is stirred at this temperature for 15 min. The melting is cooled to 80° C. and 42 ml ethanol are added carefully. The solvent is removed to obtain the crude product, a mixture of the desired product and 4-(5-thiazol-2-yl-1H-[1,2,4]triazol-3-yl)-piperidine. This mixture is used for the next reaction without further purification.

Step 5: 4-(5-Thiazol-2-yl-1H-[1,2,4]triazol-3-yl)-piperidine hydrochloride

The mixture of 7.59 g of the crude product obtained in step 4 is dissolved in dioxane and 68 ml hydrogen chloride 4M sol. in dioxane is added slowly. The product appears as an oil. After addition of 542 ml methanol the oil is dissolved. The solution is stirred over night until precipitation of the crystalline product.

Step 6: 2-Methyl-6-phenyl-5-[4-({4-[5-(1,3-thiazol-2-yl)-1H-1,2,4-triazol-3-yl]piperidin-1-yl}methyl)phenyl][1,2,4]triazolo[1,5-a]pyrimidine 0.25 ml triethylamine is added to a solution of 225 mg 4-(5-thiazol-2-yl-1H-[1,2,4]triazol-3-yl)-piperidine hydrochloride in 7.6 ml methanol. To this solution a solution of 250 mg 4-(2-methyl-6-phenyl[1,2,4]triazolo[1,5-a]pyrimidin-5-yl)benzaldehyde (prepared as described under example 37) in 7.6 ml DMF is added, followed by 0.11 ml glacial acetic acid and 337 mg NaBH(OAc)$_3$. The resulting mixture is stirred at room temperature. Six additional portions of 2 equivalents NaBH(OAc)$_3$ are added over 3 days. The solvent is removed by evaporation and the residue is purified by chromatography on silica gel (dichloromethane/[dichloromethane+7M NH$_3$ in methanol]) to yield the desired compound.

MS (M+1): 534

Characteristic 1H NMR (300 MHz, dDMSO) signals: 9.3 ppm (s, 1H); 7.9 ppm (m, 1H); 7.8 ppm (m, 1H); 3.5 ppm (s, 2H); 2.6 ppm (s, 3H)

Step 7: 2-Methyl-6-phenyl-5-[4-({4-[5-(1,3-thiazol-2-yl)-1H-1,2,4-triazol-3-yl]piperidin-1-yl}methyl)phenyl][1,2,4]triazolo[1,5-a]pyrimidine hydrochloride The hydrochloride can be obtained by adding to a solution of 2-Methyl-6-phenyl-5-[4-({4-[5-(1,3-thiazol-2-yl)-1H-1,2,4-triazol-3-yl]piperidin-1-yl}methyl)phenyl][1,2,4]-triazolo[1,5-a]pyrimidine in methanol an adequate amount of hydrochloric acid solution (5.84N in methanol). After stirring for 1 h the hydrochloride can be filtered and dried.

Example 44

2-Methyl-6-phenyl-5-(4-{[4-(5-pyridin-2-yl-1H-1,2,4-triazol-3-yl)piperidin-1-yl]methyl}phenyl)pyrazolo[1,5-a]pyrimidine

Step 1: 2-Methyl-6-phenylpyrazolo[1,5-a]pyrimidine-5,7-diol

A solution of 4.5 g 5-amino-3-methylpyrazole and 12.2 ml diethyl phenylmalonate in N,N-dibutylbutan-1-amine is stirred at 185° C. over night. After cooling to room temperature the reaction mixture forms two layers. The top layer is removed and the lower layer is diluted with dichloromethane and methanol. The resulting solution is concentrated and extracted with a mixture of diethyl ether and 10% w/w NaOH solution. The organic layer is discarded and aqueous layer acidified with concentrated HCl. The precipitated product is collected by filtration.

MS (M−1): 240

Characteristic 1H NMR (dDMSO, 300 MHz) signals: 5.9 ppm (s, 1H); 2.3 ppm (s, 3H)

Step 2: 5,7-Dichloro-2-methyl-6-phenylpyrazolo[1,5-a]pyrimidine 6.1 g 2-methyl-6-phenylpyrazolo[1,5-a]pyrimidine-5,7-diol is suspended in 15 ml POCl$_3$. 5.00 ml N,N-dimethylaniline is added and the mixture is stirred at 100° C. for 3 h. The excess of POCl$_3$ is removed and the residue is treated with ice and water until precipitation of the product. The precipitate is collected by filtration and purified on silica gel (dichloromethane/ethyl acetate) to yield the desired product.

MS (M+1): 278

Characteristic 1H NMR (300 MHz, dDMSO) signals: 7.5 ppm (m, 5H); 6.7 ppm (s, 1H)

Step 3: 5-Chloro-2-methyl-6-phenylpyrazolo[1,5-a]pyrimidine 2.47 g 5,7-dichloro-2-methyl-6-phenylpyrazolo[1,5-a]pyrimidine is dissolved in 80 ml dichloromethane. 80 ml brine, 40 ml ammonia solution 25% w/w and 2.47 g zinc powder are added and the mixture is stirred at room temperature for 2 d. Four additional portions of 4.2 equivalents zinc powder are added over 4 days. The reaction mixture is filtrated over kieselgur and washed with dichloromethane and water. The organic phase is separated and the water phase extracted with dichloromethane. The combined dichloromethane phase is dried over Na$_2$SO$_4$ and the solvent is evaporated. The residue is purified on silica gel (dichloromethane/ethyl acetate) to yield the desired product.

MS (M+1): 244

Characteristic 1H NMR (300 MHz, dDMSO) signals: 9.1 ppm (s, 1H); 6.6 ppm (s, 1H); 2.4 ppm (s, 3H)

Step 4: 4-(2-Methyl-6-phenylpyrazolo[1,5-a]pyrimidin-5-yl)benzaldehyde

To a mixture of 1.35 g of 5-chloro-2-methyl-6-phenylpyrazolo[1,5-a]pyrimidine and 1.04 g 4-formylphenylboronic acid in 20 ml 1,2-dimethoxyethane are added 10.8 ml of a 10% w/w sodium carbonate solution and 120 mg dichloro[1,1'-bis(diphenylphosphino)ferrocene]palladium (II). The resulting mixture is heated to 100° C. by microwave irradiation under an inert gas atmosphere for 75 min. The work up is performed by diluting the reaction mixture with water and dichloromethane, separating the phases and extraction of the aqueous phase with dichloromethane. The combined organic layers are dried over sodium sulphate and evaporated. The crude product is purified by chromatography on silica gel (dichloromethane/methanol) to yield the desired product.

MS (M+1): 314

Characteristic 1H NMR (300 MHz, dDMSO) signals: 10.0 ppm (s, 1H); 9.1 ppm (s, 1H); 7.8 ppm (m, 2H); 7.5 ppm (m, 2H);

Step 5: 6-Phenyl-5-(4-{[4-(5-pyridin-2-yl-1H-1,2,4-triazol-3-yl)piperidin-1-yl]methyl}phenyl)pyrazolo[1,5-a]pyrimidine 0.51 ml triethylamine is added to a solution of 581 mg 2-(5-piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 15 ml methanol. To this solution a solution of 500 mg 4-(2-methyl-6-phenylpyrazolo[1,5-a]pyrimidin-5-yl)benzaldehyde in 15 ml DMF is added, followed by 0.23 ml glacial acetic acid and 676 mg NaBH(OAc)$_3$. The resulting mixture is stirred at room temperature. Fife additional portions of 2 equivalents NaBH(OAc)$_3$ are added over 8 h. The solvent is removed by evaporation after 24 h and the residue is purified by chromatography on silica gel (dichloromethane/[dichloromethane+7M NH3 in methanol]) to yield the desired compound.

MS (M+1): 527

Characteristic 1H NMR (dDMSO, 300 MHz) signals: 9.0 ppm (s, 1H); 8.7 ppm (m, 1H); 6.6 ppm (s, 1H); 3.5 ppm (s, 2H); 2.4 ppm (s, 3H)

Step 6: 6-Phenyl-5-(4-{[4-(5-pyridin-2-yl-1H-1,2,4-triazol-3-yl)piperidin-1-yl]methyl}phenyl)pyrazolo[1,5-a]pyrimidine hydrochloride The hydrochloride can be obtained by adding to a solution of 6-Phenyl-5-(4-{[4-(5-pyridin-2-yl-1H-1,2,4-triazol-3-yl)piperidin-1-yl]methyl}phenyl)pyrazolo[1,5-a]pyrimidine in methanol a hydrochloric acid solution (5.84N in methanol). After stirring the mixture for 1 h the hydrochloride can be filtered and dried.

Example 45

2-Methyl-6-phenyl-5-(4-{[4-(5-pyrimidin-2-yl-1H-1,2,4-triazol-3-yl)piperidin-1-yl]methyl}phenyl)[1,2,4]triazolo[1,5-a]pyrimidine Example 45 is synthesized in a manner according to example 37 by using 2-(3-piperidin-4-yl-1H-1,2,4-triazol-5-yl)pyrimidine instead of 2-(5-piperidin-[1,2,4]triazol-3-yl)-pyridine, which is synthesized from tert-butyl 4-(hydrazinocarbonyl)piperidine-1-carboxylate and pyrimidine-2-carbonitrile according to a procedure described in U.S. Pat. No. 4,011,218 or WO2005100344.

MS (M+1): 529

Characteristic 1H NMR (dDMSO, 300 MHz) signals: 9.3 ppm (s, 1H); 8.9 ppm (m, 1H); 3.5 ppm (s, 2H); 2.6 ppm (s, 3H)

Example 46

2-Methyl-6-phenyl-5-(4-{[4-(3-pyridin-2-yl-1H-pyrazol-5-yl)piperidin-1-yl]methyl}phenyl)[1,2,4]triazolo[1,5-a]pyrimidine Example 45 is synthesized in a manner according to example 37 by using 2-(3-piperidin-4-yl-pyrazol-3-yl)pyridine*HCl instead of 2-(3-Piperidin-[1,2,4]triazol-3-yl)-pyridine in the last step which was prepared as described in Bioorg. Med. Chem. Lett.; EN; 12; 3; 2002; 383-386.

MS (M+1): 527

Characteristic 1H NMR (300 MHz, dDMSO) signals: 9.3 ppm (s, 1H); 8.5 ppm (m, 1H); 6.6 ppm (m, 1H); 3.5 ppm (s, 2H); 2.6 ppm (s, 3H)

Example 47

2-Methyl-6-phenyl-5-(4-{[4-(5-pyridin-4-yl-1H-1,2,4-triazol-3-yl)piperidin-1-yl]methyl}phenyl)[1,2,4]triazolo[1,5-a]pyrimidine Example 47 is synthesized in a manner according to example 37 by using 4-(5-piperidin-4-yl-1H-1,2,4-triazol-3-yl)pyridine instead of 2-(5-piperidin-[1,2,4]triazol-3-yl)-pyridine, which is synthesized from tert-butyl 4-(hydrazinocarbonyl)piperidine-1-carboxylate and pyridine-4-carbonitrile according to a procedure described in U.S. Pat. No. 4,011,218 or WO2005100344.

MS (M+1): 528

Characteristic 1H NMR (300 MHz, dDMSO) signals: 9.3 ppm (s, 1H); 8.7 ppm (d, 2H); 7.9 ppm (d, 2H); 3.5 ppm (s, 2H); 2.6 ppm (s, 3H)

Example 48

2-Cyclopropyl-6-phenyl-5-(4-{[4-(5-pyridin-2-yl-1H-1,2,4-triazol-3-yl)piperidin-1-yl]methyl}phenyl)pyrazolo[1,5-a]pyrimidine This compound is prepared in a manner according to example 45 by using 3-cyclopropyl-1H-pyrazol-5 amine in the first step.

MS (M+1): 553

Characteristic 1H NMR (dDMSO, 300 MHz) signals: 9.0 ppm (s, 1H); 8.7 ppm (m, 1H); 6.5 ppm (s, 1H); 3.5 ppm (s, 2H); 1.1 ppm (m, 2H); 0.9 ppm (m, 2H)

Example 49

2,7-Dimethyl-6-phenyl-5-(4-{[4-(5-pyridin-2-yl-1H-1,2,4-triazol-3-yl)piperidin-1-yl]methyl}phenyl)pyrazolo[1,5-a]pyrimidine This compound is prepared in a manner according to example 40 by using 3-amino-5-methylpyrazol in the first step.

MS (M+1): 541
Characteristic 1H NMR (dDMSO, 300 MHz) signals: 8.7 ppm (m, 1H); 6.6 ppm (s, 1H); 2.6 ppm (s, 3H); 2.6 ppm (s, 3H)

Example 50

5-(4-{[4-(5-Pyridin-2-yl-1H-1,2,4-triazol-3-yl)piperidin-1-yl]methyl}phenyl)-6-(3-thienyl)pyrazolo[1,5-a]pyrimidine Step 1: 5,7-Dichloro-6-thiophen-3-yl-pyrazolo[1,5-a]pyrimidine To 3.80 g 3-aminopyrazol and 8.50 g 3-thienyl malonic acid are added dropwise over 2 minutes 106 ml POCl$_3$ and stirred at 90° C. for 48 hours. The mixture is poured on ice and stirred for 1 hour. The precipitate is collected by filtration, washed with water and dissolved in warm ethanol. The mother liquor is added with sodium hydroxide and ethyl acetate. The organic phase is separated and the water phase is extracted with ethyl acetate. The organic layers are dried over Na$_2$SO$_4$ and the solvent is evaporated.

Step 2: 5-Chloro-6-thiophen-3-yl-pyrazolo[1,5-a]pyrimidine 2.450 g 5,7-dichloro-2-methyl-6-phenylpyrazolo[1,5-a]pyrimidine are dissolved in 79 ml dichloromethane. 79 ml brine, 40 ml ammonia solution 25% w/w and 2.54 g zinc powder are added and the mixture is stirred at 60° C. for 1.5 h. The reaction mixture is filtrated over sand and washed with dichloromethane and water. The organic phase is separated and the aqueous phase is extracted with dichloromethane. The combined dichloromethane phase is dried over Na$_2$SO$_4$ and the solvent is evaporated. The residue is purified on silica gel (dichloromethane/ethyl acetate) to yield the desired product.

Step 3: 4-[6-(3-Thienyl)pyrazolo[1,5-a]pyrimidin-5-yl]benzaldehyde

To a mixture of 276 mg 5-chloro-6-thiophen-3-yl-pyrazolo[1,5-a]pyrimidine and 228 mg 4-formylphenylboronic acid in 13 ml 1,2-dimethoxyethane are added 1.8 ml of a 10% w/w sodium carbonate solution and 48 mg dichloro[1,1'-bis(diphenylphosphino)ferrocene]palladium (II). The resulting mixture is heated to 80° C. under an inert gas atmosphere for 7 h. An additional portion of 228 mg 4-formylphenylboronic acid and 48 mg dichloro[1,1'-bis(diphenylphosphino)ferrocene]palladium (II) is added and the mixture is heated to 80° C. for 2 h. The work up is performed by diluting the reaction mixture with water and dichloromethane, separating the phases and extraction of the aqueous phase with dichloromethane. The combined organic layers are dried over sodium sulphate and the solvent is evaporated. The solid residue is stirred in diethylether, filtered and dried to yield the desired product.

Step 4: 2,7-Dimethyl-6-phenyl-5-(4-{[4-(5-pyridin-2-yl-1H-1,2,4-triazol-3-yl)piperidin-1-yl]methyl}phenyl)pyrazolo[1,5-a]pyrimidine 175 mg 2-(5-piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344), 0.19 ml triethylamine, 148 mg 4-[6-(3-thienyl)pyrazolo[1,5-a]pyrimidin-5-yl]benzaldehyde and 0.038 ml titanium(IV) isopropylate is stirred in 12 ml abs. THF over night. 62 mg sodium cyanoborohydride are added to this solution and the mixture is stirred at room temperature for 1 h. The solvent is evaporated and the residue is purified on silica gel (chloroform/methanol) to yield the desired product.
MS (M+1): 519
Characteristic 1H NMR (dDMSO, 300 MHz) signals: 9.1 ppm (s, 1H); 8.6 ppm (m, 1H); 6.8 ppm (m, 1H); 3.5 ppm (s, 2H)

Step 5: 2,7-Dimethyl-6-phenyl-5-(4-{[4-(5-pyridin-2-yl-1H-1,2,4-triazol-3-yl)piperidin-1-yl]methyl}phenyl)pyrazolo[1,5-a]pyrimidine with (E)-butenedioic acid The product can be obtained by adding to a solution of 2,7-Dimethyl-6-phenyl-5-(4-{[4-(5-pyridin-2-yl-1H-1,2,4-triazol-3-yl)piperidin-1-yl]methyl}phenyl)pyrazolo-[1,5-a]pyrimidine in acetone an adequate amount of (E)-butenedioic acid. After stirring for 5-24 h the product can be isolated.

Example 51

7-(4-{[4-(5-Pyridin-2-yl-1H-1,2,4-triazol-3-yl)piperidin-1-yl]methyl}phenyl)-6-(3-thienyl)imidazo[1,2-a]pyrimidine This compound is prepared in a manner according to example 50 by using 2-aminoimidazol in the first step.
MS (M+1): 519
Characteristic 1H NMR (dDMSO, 300 MHz) signals: 9.2 ppm (s, 1H); 8.6 ppm (m, 1H); 6.8 ppm (m, 1H); 3.5 ppm (s, 2H)

Example 52

2-Bromo-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine Step 1: 2-Amino-6-phenyl[1,2,4]triazolo[1,5-a]pyrimidine-5,7-diol A solution of 9.0 g 3,5-diamino-1,2,4-triazole and 22.4 ml diethyl phenylmalonate in N,N-dibutylbutan-1-amine is heated under microwave irradiation to 180° C. for 8 h. The reaction mixture forms two layers after cooling to room temperature. The top layer is removed and the solvent of the lower layer is evaporated. The residue is treated with water and acidified with 5N HCl. The precipitated product is collected by filtration and dried. The crude product is used without further purification.
MS (M+1): 244

Step 2: 5,7-Dichloro-6-phenyl[1,2,4]triazolo[1,5-a]pyrimidin-2-amine 29 g 2-amino-6-phenyl[1,2,4]triazolo[1,5-a]pyrimidine-5,7-diol is suspended in 150 ml POCl$_3$. 17.14 ml N,N-dimethylaniline are added and the mixture is stirred at 100° C. for 2 h. The excess of POCl$_3$ is removed by evaporation and the residue is treated with ice and a mixture of water/ethanol (9:1) until precipitation of the product. The precipitate is collected by filtration and dried to yield the desired product.

MS (M+1): 280

Characteristic 1H NMR (200 MHz, dDMSO) signals: 7.6 ppm (m, 3H); 7.4 ppm (m, 2H)

Step 3: 2,7-Dibromo-5-chloro-6-phenyl[1,2,4]triazolo[1,5-a]pyrimidine 25.0 g 5,7-dichloro-6-phenyl[1,2,4]triazolo[1,5-a]pyrimidin-2-amine are suspended in 250 ml hydrobromic acid (48% w/w). A solution of 18.4 g sodium nitrite in 60 ml water is added dropwise over 20 min. The resulting mixture is heated to 65° C. After 1 and 2.5 h additional portions of 3.1 g sodium nitrite dissolved in 10 ml water are added. The reaction mixture is diluted with 500 ml water and 1 l ethyl acetate after 3 h. The organic phase is separated and the water phase is extracted with ethyl acetate. The combined organic layers are washed with 1N NaOH solution, with saturated $Na_2CO_3$ solution and brine. The combined organic layers are dried over $Na_2SO_4$ and the solvent is evaporated. The solid residue is stirred in ethanol for 2 h. The crude product is filtered, dried and is used without further purification.

MS (M+1): 389

Characteristic 1H NMR (300 MHz, dDMSO) signals: 7.6 ppm (m, 3H); 7.4 ppm (m, 2H)

Step 4: 2-Bromo-5-chloro-6-phenyl[1,2,4]triazolo[1,5-a]pyrimidine

A mixture of 29.4 g 2,7-dibromo-5-chloro-6-phenyl[1,2,4]triazolo[1,5-a]pyrimidine, 125 ml methanol, 500 ml THF, 12.9 ml glacial acetic acid and 14.7 g of Zn/Cu pair are stirred at 45° C. After 3 and 5 hours additional portions of 7.3 g Zn/Cu pair are added. The mixture is filtered through celite and the filtrate is diluted with water and ethyl acetate. The phases are separated and the water layer is extracted with ethyl acetate. The combined organic layers are washed with saturated $Na_2CO_3$ solution, dried over $Na_2SO_4$ and the solvent is evaporated. The solid residue is stirred in a mixture of 2-propanol/ethanol (3:1) for 2 h. The crude product is filtered and dried and is used without further purification.

MS (M+1): 355

Characteristic 1H NMR (300 MHz, dDMSO) signals: 9.6 ppm (s, 1H); 7.6 ppm (m, 1H)

Step 5: 4-(2-Bromo-6-phenyl[1,2,4]triazolo[1,5-a]pyrimidin-5-yl)benzaldehyde To a mixture of 1.0 g 2-bromo-5-chloro-6-phenyl[1,2,4]triazolo[1,5-a]pyrimidine and 0.48 g 4-formylphenylboronic acid in 10 ml 1,2-dimethoxyethane are added 6.2 ml of a 10% w/w sodium carbonate solution and 118 mg dichloro[1,1'-bis(diphenylphosphino)ferrocene]palladium (II) and the resulting mixture is heated to 100° C. by microwave irradiation under a inert gas atmosphere for 50 min. The work up is performed by diluting the reaction mixture with water and dichloromethane, separating the phases and extraction of the aqueous phase with dichloromethane. The combined organic layers are dried over $Na_2SO_4$ and the solvent is evaporated. The crude product is purified by chromatography on silica gel (dichloromethane/ethyl acetate) to yield the desired product.

MS (M+1): 379/380

Characteristic 1H NMR (300 MHz, dDMSO) signals: 10.0 ppm (s, 1H); 9.6 ppm (s; 1H); 7.9 ppm (m, 2H); 7.6 ppm (m, 2H)

Step 6: 2-Bromo-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine 0.84 ml triethylamine is added to a solution of 960 mg 2-(5-piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 20 ml methanol. To this solution a solution of 1 g 4-(2-bromo-6-phenyl[1,2,4]triazolo[1,5-a]pyrimidin-5-yl)benzaldehyde in 20 ml DMF is added, followed by 0.40 ml glacial acetic acid and 1.12 g $NaBH(OAc)_3$. The resulting mixture is stirred at room temperature. Two additional portions of 2 equivalents $NaBH(OAc)_3$ are added after 1 and 2 hours. The solvent is removed by evaporation after 3 h and the residue is purified by chromatography on silica gel (dichloromethane/[dichloromethane+7M $NH_3$ in methanol]) to yield the desired compound.

MS (M+1): 592/594

Characteristic 1H NMR (dDMSO, 300 MHz) signals: 9.4 ppm (s, 1H); 8.7 ppm (m, 1H); 3.5 ppm (s, 2H);

Example 53

2-Ethynyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine

Step 1: 4-{6-Phenyl-2-[(trimethylsilyl)ethynyl][1,2,4]triazolo[1,5-a]pyrimidin-5-yl}benzaldehyde 300 mg 4-(2-bromo-6-phenyl[1,2,4]triazolo[1,5-a]pyrimidin-5-yl)benzaldehyde (prepared as described under example 53), 613 mg trimethyl[(tributylstannyl)ethynyl]silane and 46 mg $Pd(PPh_3)_4$ are suspended in 12 ml toluene under a nitrogen atmosphere. The mixture is heated (microwave irradiation) to 120° C. for 1 h. This mixture is worked up by diluting with water and extraction with dichloromethane. The organic layers are dried over $Na_2SO_4$ and concentrated to yield the crude product, which is purified by chromatography on silica gel (ethyl acetate/dichloromethane).

MS (M+1): 397

Characteristic 1H NMR (300 MHz, dDMSO) signals: 10.0 ppm (s, 1H); 9.5 ppm (s, 1H); 7.9 ppm (m, 2H); 7.6 ppm (m, 2H); 0.3 ppm (s, 9H)

Step 2: 2-Ethynyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine 0.12 ml triethylamine are added to a solution of 137 mg 2-(5-piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 5 ml methanol. To this solution a solution of 150 mg 4-{6-phenyl-2-[(trimethylsilyl)ethynyl][1,2,4]triazolo[1,5-a]pyrimidin-5-yl}benzaldehyde in 5 ml DMF is added, followed by 0.057 ml glacial acetic acid and 161 mg $NaBH(OAc)_3$. The resulting mixture is stirred at room temperature. Additional portions of 2 equivalents $NaBH(OAc)_3$ are added after 1, 2, 4 and 6 hours. The solvent is removed by evaporation after 22 h. The residue is dissolved in methanol and potassium carbonate is added. The mixture is stirred over night. The solvent is evaporated and the residue is purified by chromatography on silica gel (dichloromethane/[dichloromethane+7M NH₃ in methanol]) to yield the desired compound.

MS (M+1): 538

Characteristic 1H NMR (300 MHz, dDMSO) signals: 9.4 ppm (s, 1H); 8.7 ppm (m, 1H); 4.7 ppm (s, 1H); 3.5 ppm (s, 2H)

Example 54

2-Methyl-5-(4-{[4-(5-pyridin-2-yl-1H-1,2,4-triazol-3-yl)piperidin-1-yl]methyl}phenyl)-6-(3-thienyl)[1,2,4]triazolo[1,5-a]pyrimidine This compound is prepared in a manner according to example 51 by using 5-methyl-1,2,4-triazol-3-amine in the first step.

MS (M+1): 534

Characteristic 1H NMR (dDMSO, 400 MHz) signals: 9.4 ppm (s, 1H); 8.6 ppm (m, 1H); 6.8 ppm (s, 1H); 3.5 ppm (s, 2H)

Example 55

2-Methyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine with 4-methylbenzenesulfonic acid To 0.20 g 2-methyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine (prepared as described under example 37) in 4 ml acetone are added 0.079 g 4-methylbenzenesulfonic acid monohydrate. The mixture is stirred at ambient temperature for 18 h. The desired compound is collected by filtration and dried.

MS (M+1): 528

Characteristic 1H NMR (dDMSO, 400 MHz) signals: 9.4 ppm (s, 1H); 8.7 ppm (m, 1H); 2.5 ppm (s, 3H); 2.3 ppm (s, 3H)

mp: 175° C.-185° C.

Example 56

2-Methyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine with 2-hydroxypropane-1,2,3-tricarboxylic acid Method A:

To 0.20 g 2-methyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine (prepared as described under example 37) in 4 ml acetone are added 0.080 g 2-hydroxypropane-1,2,3-tricarboxylic acid. The mixture stirred at ambient temperature for 18 h. The desired compound is collected by filtration and dried.

MS (M+1): 528

Characteristic 1H NMR (dDMSO, 300 MHz) signals: 9.4 ppm (s, 1H); 8.7 ppm (m, 1H); 2.6 ppm (s, 3H)

mp: 240° C.-250° C.

Method B:

To 0.20 g 2-methyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine (prepared as described under example 37) in 8 ml THF are added 0.080 g 2-hydroxypropane-1,2,3-tricarboxylic acid. The mixture is stirred at ambient temperature for 18 h. The desired compound is collected by filtration and dried.

MS (M+1): 528

Characteristic 1H NMR (dDMSO, 300 MHz) signals: 9.4 ppm (s, 1H); 8.7 ppm (m, 1H); 2.6 ppm (s, 3H)

mp: 235° C.-240° C.

Example 57

2-Cyclopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine with (E)-butenedioic acid To 0.20 g 2-Cyclopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine (prepared as described under example 4) in 4 ml acetone are added 0.046 g (E)-butenedioic acid. The mixture is stirred at ambient temperature for 18 h. The desired compound is collected by filtration and dried.

MS (M+1): 554

Characteristic 1H NMR (dDMSO, 300 MHz) signals: 9.3 ppm (s, 1H); 8.7 ppm (m, 1H); 6.6 ppm (s, 2H); 3.6 ppm (s, 2H)

mp: 215° C.-225° C.

Example 58

2-Cyclopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine with methanesulfonic acid To 0.20 g 2-Cyclopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine (prepared as described under example 4) in 4 ml acetone are added 0.038 g methanesulfonic acid. The mixture is stirred at ambient temperature for 18 h. The desired compound is collected by filtration and dried.

MS (M+1): 554

Characteristic 1H NMR (dDMSO, 300 MHz) signals: 9.3 ppm (s, 1H); 8.7 ppm (m, 1H); 3.6 ppm (s, 2H); 2.3 ppm (s, 3H)

mp: 180° C.-190° C.

Example 59

2-Cyclopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine with 2,3-dihydroxybutanedioic acid To 0.20 g 2-Cyclopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine (prepared as described under example 4) in 4 ml acetone are added 0.060 g 2,3-dihydroxybutanedioic acid. The mixture is stirred at ambient temperature for 18 h. The desired compound is collected by filtration and dried.

MS (M+1): 554

Characteristic 1H NMR (dDMSO, 300 MHz) signals: 9.3 ppm (s, 1H); 8.7 ppm (m, 1H); 4.2 ppm (s, 2H); 3.6 ppm (s, 2H)

mp: 180° C.-190° C.

Example 60

2-Cyclopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine with 4-methylbenzenesulfonic acid To 0.206 g 2-Cyclopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine (prepared as described under example 4) in 4.12 ml acetone are added 0.078 g 4-methylbenzenesulfonic acid monohydrate. The mixture is stirred at ambient temperature for 18 h. The desired compound is collected by filtration and dried.

MS (M+1): 554

Characteristic 1H NMR (dDMSO, 300 MHz) signals: 9.3 ppm (s, 1H); 8.7 ppm (m, 1H); 2.3 ppm (s, 3H)

mp: 170° C.-180° C.

Example 61

2-Cyclopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine with 2-hydroxypropane-1,2,3-tricyboxylic acid To 0.206 g 2-Cyclopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine (prepared as described under example 4) in 4.12 ml acetone are added 0.078 g citric acid. The mixture is stirred at ambient temperature for 18 h. The desired compound is collected by filtration and dried.

MS (M+1): 554

Characteristic 1H NMR (dDMSO, 300 MHz) signals: 9.3 ppm (s, 1H); 8.7 ppm (m, 1H)

mp: 180° C.-190° C.

Example 62

N,N-Dimethyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidin-2-amine Step 1: 4-[2-(dimethylamino)-6-phenyl[1,2,4]triazolo[1,5-a]pyrimidin-5-yl]benzaldehyde To 200 mg 4-(2-bromo-6-phenyl[1,2,4]triazolo[1,5-a]pyrimidin-5-yl)benzaldehyde (prepared as described under example 52) in 6 ml DMF are added 0.24 ml of a dimethylamin solution (60% in water). The mixture is heated under microwave irradiation to 100° C. for 2.5 hours. The solvent is removed and the solid residue is treated with ethyl acetate/petrolether (1:1) and stirred for 2 hours. The desired product is filtered, dried and is used without further purification.

MS (M+1): 344

Characteristic 1H NMR (dDMSO, 300 MHz) signals: 10.0 ppm (s, 1H); 9.2 ppm (s, 1H); 7.8 ppm (m, 2H); 7.5 ppm (m, 2H); 3.1 (s, 6H); 2.6 ppm (s, 3H)

Step 2: N,N-dimethyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidin-2-amine 0.138 ml triethylamine are added to a solution of 207 mg 2-(5-piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 10 ml methanol. To this solution a solution of 196 mg 4-[2-(dimethylamino)-6-phenyl[1,2,4]triazolo[1,5-a]pyrimidin-5-yl]benzaldehyde in 10 ml DMF is added, followed by 0.09 ml glacial acetic acid and 242 mg NaBH(OAc)₃. The resulting mixture is stirred at room temperature. Two additional portions of 2 equivalents NaBH(OAc)₃ are added after 1 and 2 hours. The solvent is removed by evaporation after 3 h and the residue is dissolved in dichloromethane and water. The phases are separated and the water phase is extracted with dichloromethane. The combined organic layers are dried over Na₂SO₄ and the solvent is evaporated. The crude product is purified by RP HPLC (water, 10 mM NH₄COOH, pH 3.7/ACN) to yield the desired compound.

MS (M+1): 557

Characteristic 1H NMR (dDMSO, 300 MHz) signals: 9.1 ppm (s, 1H); 8.7 ppm (m, 1H); 3.5 ppm (s, 2H); 3.1 ppm (s, 6H)

Example 63

6-Phenyl-5-(4-{[4-(5-pyridin-2-yl-1H-1,2,4-triazol-3-yl)piperidin-1-yl]methyl}phenyl)-2-(trifluoromethyl)[1,2,4]triazolo[1,5-a]pyrimidine This compound is prepared in a manner according to example 2 by using 5-trifluormethyl-4H-2-aminotriazole in the first step.

MS (M+1): 582

Characteristic 1H NMR (dDMSO, 300 MHz) signals: 9.6 ppm (s, 1H); 8.7 ppm (m, 1H); 3.5 ppm (s, 2H)

Example 64

N,N,2-Trimethyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidin-7-amine Step 1: 5-Chloro-N,N,2-trimethyl-6-phenyl[1,2,4]triazolo[1,5-a]pyrimidin-7-amine To 500 mg 5,7-dichloro-2-methyl-6-phenyl[1,2,4]triazolo[1,5-a]pyrimidine (prepared as described under example 37) in 25 ml DMF are added 0.8 ml of a dimethylamin solution (60% in water). The mixture is stirred at room temperature for 45 minutes. The reaction mixture is diluted with water and dichloromethane. The phases are separated and the water layer is extracted with dichloromethane. The combined organic layers are dried over Na₂SO₄ and the solvent is removed by evaporation. The residue is suspended in diethylether and stirred for 5 hours. The desired product is filtered, dried and is used without further purification for the next step.

MS (M+1): 288

Characteristic 1H NMR (dDMSO, 300 MHz) signals: 2.8 ppm (s, 6H); 2.4 ppm (s, 3H)

Step 2: 4-[7-(Dimethylamino)-2-methyl-6-phenyl[1,2,4]triazolo[1,5-a]pyrimidin-5-yl]benzaldehyde To a mixture of 370 mg 5-chloro-N,N,2-trimethyl-6-phenyl[1,2,4]triazolo[1,5-a]pyrimidin-7-amine and 231 mg 4-formylphenylboronic acid in 7 ml 1,2-dimethoxyethane are added 2.5 ml of a 10% w/w sodium carbonate solution and 47 mg dichloro[1,1'-bis(diphenylphosphino)ferrocene]palladium (II). The resulting mixture is heated to 130° C. by microwave irradiation under a inert gas atmosphere for 1 hour. The work up is performed by diluting the reaction mixture with water and dichloromethane, separating the phases and extraction of the aqueous phase with dichloromethane. The combined organic layers are dried over sodium sulphate and the solvent is evaporated. The crude product is purified by chromatography on silica gel (dichloromethane/methanol) to yield the desired product.

MS (M+1): 358

Characteristic 1H NMR (300 MHz, dDMSO) signals: 10.0 ppm (s, 1H); 7.7 ppm (m, 2H); 7.4 ppm (m, 2H); 2.8 ppm (s, 6H)

Step 3: N,N,2-trimethyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidin-7-amine 0.28 ml triethylamine are added to a solution of 317 mg 2-(5-piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 5 ml methanol. To this solution a solution of 390 mg 4-[7-(dimethylamino)-2-methyl-6-phenyl[1,2,4]triazolo[1,5-a]pyrimidin-5-yl]benzaldehyde in 5 ml DMF is added, followed by 0.13 ml glacial acetic acid and 445 mg NaBH(OAc)$_3$. The resulting mixture is stirred at room temperature. Additional portions of 2 equivalents NaBH(OAc)$_3$ are added after 1 and 2 hours. The solvent is removed by evaporation after 3 h and the residue is purified by chromatography on silica gel (dichloromethane/[dichloromethane+ 7M NH$_3$ in methanol]) to yield the desired compound.

MS (M+1): 571

Characteristic 1H NMR (dDMSO, 300 MHz) signals: 8.7 ppm (m, 1H); 3.5 ppm (s, 2H); 2.8 ppm (s, 6H);

Example 65

N-Methyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidin-2-amine 150 mg 2-bromo-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine (prepared as described under example 52) is dissolved in 8 ml of a methylamine solution (2M in THF). The reaction mixture is heated under microwave irradiation to 110° C. for 8 hours. The solvent is evaporated and the residue is purified by RP HPLC (water, 10 mM NH$_4$COOH, pH 3.7/ACN) to yield the desired compound.

MS (M+1): 543

Characteristic 1H NMR (dDMSO, 400 MHz) signals: 9.0 ppm (s, 1H); 8.7 ppm (m, 1H); 6.9 ppm (q, 1H); 3.5 ppm (s, 2H); 2.9 ppm (d, 3H);

Example 66

2-Methoxy-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine To 110 mg 2-bromo-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine (prepared as described under example 53) in 5 ml methanol are added 1.11 ml of a sodium methoxide solution (25% in methanol). The reaction mixture is heated to 55° C. for 3.5 hours and diluted with water and dichloromethane. The phases are separated and the water layer is extracted with dichloromethane. The combined organic layers are dried over Na$_2$SO$_4$ and the solvent are removed by evaporation. The residue is purified by RP HPLC (water, 10 mM NH$_4$COOH, pH 3.7/ACN) to yield the desired compound.

MS (M+1): 544

Characteristic 1H NMR (dDMSO, 400 MHz) signals: 9.3 ppm (s, 1H); 8.7 ppm (s, 1H); 4.1 ppm (s, 1H); 3.5 ppm (s, 2H);

Example 67

6-Phenyl-5-(4-{[4-(5-pyridin-2-yl-1H-1,2,4-triazol-3-yl)piperidin-1-yl]methyl}phenyl)[1,2,4]triazolo[1,5-a]pyrimidin-2-amine To 500 mg 2-bromo-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine (prepared as described under example 53) in 3 ml THF and 5 ml ethanol are added 8 ml of a ammonia solution (25% in water). The reaction mixture is heated to 140° C. for 22 hours. The solvent is evaporated and the solid residue is stirred in diethyl ether/ethanol (9:1). The product is filtrated, dried and further purified by RP HPLC (water, 10 mM NH$_4$COOH, pH 3.7/ACN) to yield the desired compound.

MS (M+1): 529

Characteristic 1H NMR (dDMSO, 300 MHz) signals: 9.1 ppm (s, 1H); 8.7 (m, 1H);

Example 68

6-Phenyl-7-[4-({4-[3-(1H-pyrrol-2-yl)-1H-1,2,4-triazol-5-yl]piperidin-1-yl}methyl)phenyl]imidazo[1,2-a]pyrimidine

Step 1: 1H-pyrrole-2-carbohydrazonamide

A solution of 10 g 1H-pyrrole-2-carbonitrile and 1 eq sodium methoxide in 20 ml ethanol and stirred for 10 min. Hydrazine hydrate (3 eq.) is then added and resulting reaction mixture is stirred at room temperature for 18 h. The Reaction mixture is then diluted with water, extracted with ethyl acetate, dried over Na$_2$SO$_4$ and concentrated under vacuum to yield desired compound.

Step 3 to 5: 4-[5-(1H-pyrrol-2-yl)-1H-1,2,4-triazol-3-yl]piperidine

The further synthesis is similar to example 43 from step 3 to step 5 by using 1H-pyrrole-2-carbohydrazonamide instead of thiazole-2-yl-iminocarbonylhydrazine.

Step 6: 6-Phenyl-7-[4-({4-[3-(1H-pyrrol-2-yl)-1H-1,2,4-triazol-5-yl]piperidin-1-yl}methyl)phenyl]imidazo[1,2-a]pyrimidine Example 68 is synthesized in a manner according to example 2 by using 4-[5-(1H-pyrrol-2-yl)-1H-1,2,4-triazol-3-yl]piperidine instead of 2-(3-piperidin-[1,2,4]triazol-3-yl)-pyridine,
MS (M+1): 501
Characteristic 1H NMR (dDMSO, 300 MHz) signals: 9.0 ppm (s, 1H); 7.9 ppm (d, 1H); 7.8 ppm (d, 1H); 6.1 ppm (m, 1H); 3.5 ppm (s, 2H)

Example 69

6-Phenyl-5-(4-{[4-(3-pyrimidin-2-yl-1H-1,2,4-triazol-5-yl)piperidin-1-yl]methyl}phenyl)pyrazolo[1,5-a]pyrimidine Example 69 is synthesized in a manner according to example 19 by using 2-(3-piperidin-4-yl-1H-1,2,4-triazol-5-yl)pyrimidine instead of 2-(5-piperidin-[1,2,4]triazol-3-yl)-pyridine, which is synthesized from tert-butyl 4-(hydrazinocarbonyl)piperidine-1-carboxylate and pyrimidine-2-carbonitrile according to a procedure described in U.S. Pat. No. 4,011,218 or WO2005100344.
MS (M+1): 514
Characteristic 1H NMR (dDMSO, 300 MHz) signals: 9.1 ppm (s, 1H); 8.9 (m, 2H); 8.3 ppm (d, 1H); 6.8 ppm (d, 1H); 3.5 ppm (s, 2H)

Example 70

6-Phenyl-5-[4-({4-[3-(1,3-thiazol-2-yl)-1H-1,2,4-triazol-5-yl]piperidin-1-yl}methyl)phenyl]pyrazolo[1,5-a]pyrimidine Example 70 is synthesized in a manner according to example 19 by using 4-(5-Thiazol-2-yl-1H-[1,2,4]triazol-3-yl)-piperidine hydrochloride instead of 2-(5-piperidin-[1,2,4]triazol-3-yl)-pyridine, which synthesis is described in example 44.
MS (M+1): 519
Characteristic 1H NMR (dDMSO, 300 MHz) signals: 9.1 ppm (s, 1H); 8.3 ppm (d, 1H); 8.0 ppm (d, 1H); 7.8 ppm (d, 1H); 6.8 ppm (d, 1H); 3.5 ppm (s, 2H)

Example 71

6-Phenyl-5-(4-{[4-(3-pyridin-4-yl-1H-1,2,4-triazol-5-yl)piperidin-1-yl]methyl}phenyl)pyrazolo[1,5-a]pyrimidine Example 71 is synthesized in a manner according to example 19 by using 4-(5-piperidin-4-yl-1H-1,2,4-triazol-3-yl)pyridine instead of 2-(5-piperidin-[1,2,4]triazol-3-yl)-pyridine, which is synthesized from tert-butyl 4-(hydrazinocarbonyl)piperidine-1-carboxylate and pyridine-4-carbonitrile according to a procedure described in U.S. Pat. No. 4,011,218 or WO2005100344.

MS (M+1): 513
Characteristic 1H NMR (300 MHz, dDMSO) signals: 9.1 ppm (s, 1H); 8.7 ppm (m, 2H); 8.3 ppm (d, 1H); 7.9 ppm (m, 2H); 6.8 ppm (d, 1H)

Example 72

6-Phenyl-5-[4-({4-[3-(1H-pyrrol-2-yl)-1H-1,2,4-triazol-5-yl]piperidin-1-yl}methyl)phenyl]pyrazolo[1,5-a]pyrimidine Example 72 is synthesized in a manner according to example 19 by using 4-[5-(1H-pyrrol-2-yl)-1H-1,2,4-triazol-3-yl]piperidine (prepared as described under example 69) instead of 2-(5-piperidin-[1,2,4]triazol-3-yl)-pyridine.
MS (M+1): 501
Characteristic 1H NMR (dDMSO, 300 MHz) signals: 9.1 ppm (s, 1H); 8.3 ppm (d, 1H); 7.8 ppm (m, 2H); 6.1 (m, 1H); 3.5 ppm (s, 2H)

Example 73

2-Methyl-6-phenyl-5-[4-({4-[3-(1H-pyrrol-2-yl)-1H-1,2,4-triazol-5-yl]piperidin-1-yl}methyl)phenyl][1,2,4]triazolo[1,5-a]pyrimidine Example 73 is synthesized in a manner according to example 37 by using 4-[5-(1H-pyrrol-2-yl)-1H-1,2,4-triazol-3-yl]piperidine (prepared as describe under example 68) instead of 2-(5-piperidin-[1,2,4]triazol-3-yl)-pyridine.
MS (M+1): 516
Characteristic 1H NMR (dDMSO, 300 MHz) signals: 9.3 ppm (s, 1H); 6.8 ppm (m, 1H); 6.1 ppm (m, 1H)

Example 74

2-Methyl-5-[4-({4-[3-(6-methylpyridin-2-yl)-1H-1,2,4-triazol-5-yl]piperidin-1-yl}methyl)phenyl]-6-phenyl[1,2,4]triazolo[1,5-a]pyrimidine Example 74 is synthesized in a manner according to example 37 by using 2-methyl-6-(5-piperidin-4-yl-1H-1,2,4-triazol-3-yl)pyridine instead of 2-(5-piperidin-[1,2,4]triazol-3-yl)-pyridine, which is synthesized from tert-butyl 4-(hydrazinocarbonyl)piperidine-1-carboxylate and 6-methylpyridine-2-carbonitrile according to a procedure described in U.S. Pat. No. 4,011,218 or WO2005100344.
MS (M+1): 542
Characteristic 1H NMR (dDMSO, 300 MHz) signals: 9.3 ppm (s, 1H); 7.8 ppm (m, 2H); 3.5 ppm (s, 2H); 2.6 ppm (m, 6H)

Example 75

5-[4-({4-[3-(6-Methylpyridin-2-yl)-1H-1,2,4-triazol-5-yl]piperidin-1-yl}methyl)phenyl]-6-phenylpyrazolo[1,5-a]pyrimidine Example 75 is synthesized in a manner according to example 19 by using 2-methyl-6-(5-piperidin-4-yl-1H-1,2,4-triazol-3-yl)pyridine instead of 2-(5-piperidin-[1,2,4]triazol-3-yl)-pyridine, which is synthesized from tert-butyl 4-(hydrazinocarbonyl)piperidine-1-carboxylate and 6-methylpyridine-2-carbonitrile according to a procedure described in U.S. Pat. No. 4,011,218 or WO2005100344.

MS (M+1): 527
Characteristic 1H NMR (dDMSO, 400 MHz) signals: 9.1 ppm (s, 1H); 8.3 ppm (d, 1H); 6.8 ppm (d, 1H)

Example 76

6-Phenyl-5-(4-{[4-(3-pyridin-2-yl-1H-pyrazol-5-yl)piperidin-1-yl]methyl}phenyl)pyrazolo[1,5-a]pyrimidine Example 76 is synthesized in a manner according to example 19 by using 2-(3-piperidin-4-yl-pyrazol-3-yl)pyridine*HCl instead of 2-(3-Piperidin-[1,2,4]triazol-3-yl)-pyridine in the last step which was prepared as described in *Bioorg. Med. Chem. Lett.*; 2002, 12, 383-386.

MS (M+1): 512
Characteristic 1H NMR (300 MHz, dDMSO) signals: 9.1 ppm (s, 1H); 8.6 ppm (m, 1H); 8.3 ppm (d, 1H); 6.8 ppm (d, 1H); 6.6 ppm (m, 1H); 3.5 ppm (s, 2H)

Example 77

Methyl 6-phenyl-5-(4-{[4-(5-pyridin-2-yl-1H-1,2,4-triazol-3-yl)piperidin-1-yl]methyl}phenyl)pyrazolo[1,5-a]pyrimidine-2-carboxylate Step 1: Methyl 3-nitro-1H-pyrazole-5-carboxylate 9.0 g 5-nitro-3-pyrazolo carboxylic acid are dissolved in abs. methanol and 7.6 ml thionylchloride are added dropwise at −10° C. The reaction mixture is stirred at room temperature and refluxed for 4 h. The solvent is evaporated and the crude product is used without further purification for the next step.

MS (M+1): 171
Characteristic 1H NMR (300 MHz, dDMSO) signals: 7.5 ppm (s, 1H); 3.9 ppm (s, 3H)

Step 2: Methyl 3-amino-1H-pyrazole-5-carboxylate

To 14.0 g methyl 3-nitro-1H-pyrazole-5-carboxylate in 200 ml methanol are added 1.2 g Pd/C (10% w/w). The mixture is stirred under $H_2$-atmosphere at room temperature for 18 h. The mixture is filtrated over kieselgur. The filtrate is concentrated and the crude product is used without further purification.

MS (M+1): 141
Characteristic 1H NMR (300 MHz, dDMSO) signals: 5.7 ppm (s, 1H); 3.8 ppm (s, 3H)

Step 3: Methyl 5,7-dihydroxy-6-phenylpyrazolo[1,5-a]pyrimidine-2-carboxylate

A solution of 5.0 g Methyl 3-amino-1H-pyrazole-5-carboxylate, 8.3 ml diethyl-phenylmalonate and 50 ml diisopropylethylamine in 50 ml DMF is heated to 150° C. for 40 h. The solvent is removed, the solid residue is dissolved in 2-propanol the mixture is stirred for 3 hours. The desired product is filtrated, dried and is used without further purification.

MS (M+1): 286
Characteristic 1H NMR (300 MHz, dDMSO) signals: 6.0 (s, 1H); 3.8 (s, 3H)

Step 4: Methyl 5,7-dichloro-6-phenylpyrazolo[1,5-a]pyrimidine-2-carboxylate 6.4 g methyl 5,7-dihydroxy-6-phenylpyrazolo[1,5-a]pyrimidine-2-carboxylate is suspended in 60 ml $POCl_3$. The mixture is heated to 100° C. for 30 min. The solvent is removed, the residue is treated with ice and water until precipitation of the product. The precipitate is collected by filtration, which is purified by recrystallization from ethanol.

MS (M+1) 322
Characteristic 1H NMR signals (300 MHz, dDMSO): 7.4 ppm (s, 1H); 3.9 ppm (s, 3H)

Step 5: Methyl 5-chloro-6-phenylpyrazolo[1,5-a]pyrimidine-2-carboxylate 2.00 g methyl 5,7-dichloro-6-phenylpyrazolo[1,5-a]pyrimidine-2-carboxylate are dissolved in 40 ml dichloromethane. 40 ml brine, 20 ml ammonia solution 25% w/w and 1.22 g zinc powder are added and the mixture is stirred at 60° C. for 3 h. The reaction mixture is filtrated over kieselgur and is washed with dichloromethane and water. The organic phase is separated and the water phase is extracted with dichloromethane. The combined dichloromethane phase is dried over $Na_2SO_4$ and evaporated. The crude product contains methyl 5,7-dichloro-6-phenylpyrazolo[1,5-a]pyrimidine-2-carboxylate. The crude product is dissolved again in 20 ml dichloromethane. 20 ml brine, 10 ml ammonia solution 25% w/w and 0.60 g zinc powder are added and the mixture is stirred at 60° C. for 45 min. The reaction mixture is filtrated over kieselgur and washed with dichloromethane and water. The organic phase is separated and the water phase is extracted with dichloromethane. The combined dichloromethane phase is dried over $Na_2SO_4$, the solvent is evaporated and the residue is purified by chromatography on silica gel (dichloromethane/ethyl acetate) to yield the desired compound.

MS (M+1): 287
Characteristic 1H NMR (300 MHz, dDMSO) signals: 9.4 ppm (s, 1H); 7.2 ppm (s, 1H); 3.9 ppm (s, 3H)

Step 6: Methyl 5-(4-formylphenyl)-6-phenylpyrazolo[1,5-a]pyrimidine-2-carboxylate and 5-(4-formylphenyl)-6-phenylpyrazolo[1,5-a]pyrimidine-2-carboxylic acid To a mixture of 1.0 g methyl 5-chloro-6-phenylpyrazolo[1,5-a]pyrimidine-2-carboxylate and 670 mg 4-formylphenylboronic acid in 14 ml 1,2-dimethoxyethane are added 6.7 ml of a 10% w/w sodium carbonate solution and 130 mg dichloro[1,1'-bis(diphenylphosphino)ferrocene]-palladium (II). The resulting mixture is heated to 110° C. by microwave irradiation under an inert gas atmosphere for 1 hour. The work up is performed by diluting the reaction mixture with water and dichlormethane, separating the phases and extraction of the aqueous phase with dichlormethane. The combined organic layers are dried over sodium sulphate and the solvent is evaporated. The crude product is purified by chromatography on silica gel (dichloromethane/ethyl acetate) to yield the desired product (methyl 5-(4-formylphenyl)-6-phenylpyrazolo[1,5-a]pyrimidine-2-carboxylate). The water phase contained the free acid of the desired product (5-(4-formylphenyl)-6-phenylpyrazolo[1,5-a]pyrimidine-2-carboxylic acid), which is isolated by acidification of the water layer and extraction with dichloromethane. The combined organic layers are dried over $Na_2SO_4$ and the solvent is evaporated. The residue is suspended in ethyl acetate and petrol ether (1:1) for 2 hours. The product is collected by filtration and used without further purification. Methyl 5-(4-formylphenyl)-6-phenylpyrazolo[1,5-a]pyrimidine-2-carboxylate:

MS (M+1): 358
Characteristic 1H NMR (300 MHz, dDMSO) signals: 10.0 ppm (s, 1H); 9.4 ppm (s, 1H); 7.9 ppm (m, 2H); 7.6 ppm (m, 2H); 3.9 ppm (s, 3H)

5-(4-formylphenyl)-6-phenylpyrazolo[1,5-a]pyrimidine-2-carboxylic acid:
MS (M+1): 344
Characteristic 1H NMR (300 MHz, dDMSO) signals: 10.0 ppm (s, 1H); 9.3 ppm (s, 1H); 7.9 ppm (m, 2H); 7.6 ppm (m, 2H)

Step 7: Methyl 6-phenyl-5-(4-{[4-(5-pyridin-2-yl-1H-1,2,4-triazol-3-yl)piperidin-1-yl]methyl}phenyl)pyrazolo[1,5-a]pyrimidine-2-carboxylate 0.36 ml triethylamine is added to a solution of 406 mg 2-(5-piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 15 ml methanol. To this solution a solution of 400 mg methyl 5-(4-formylphenyl)-6-phenylpyrazolo[1,5-a]pyrimidine-2-carboxylate in 15 ml DMF is added, followed by 0.17 ml glacial acetic acid and 473 mg NaBH(OAc)$_3$. The resulting mixture is stirred at room temperature. Additional portions of 2 equivalents NaBH(OAc)$_3$ are added after 1 and 2 hours. The solvent is removed by evaporation after 3 h and the residue is purified by chromatography on silica gel (dichloromethane/[dichloromethane+7M NH$_3$ in methanol]) to yield the desired compound.
MS (M+1): 571
Characteristic 1H NMR (dDMSO, 300 MHz) signals: 9.3 ppm (s, 1H); 8.7 ppm (m, 1H); 3.9 ppm (s, 3H); 3.5 ppm (s, 2H)

Example 78

6-Phenyl-5-(4-{[4-(5-pyridin-2-yl-1H-1,2,4-triazol-3-yl)piperidin-1-yl]methyl}phenyl)pyrazolo[1,5-a]pyrimidine-2-carboxamide 100 mg methyl 6-phenyl-5-(4-{[4-(5-pyridin-2-yl-1H-1,2,4-triazol-3-yl)piperidin-1-yl]methyl}phenyl)pyrazolo[1,5-a]pyrimidine-2-carboxylate (prepared as described under example 78) are dissolved in 5 ml 7N ammonia solution in methanol and heated under microwave irradiation to 120° C. for 50 minutes. The solvent is evaporated and the residue is purified by RP HPLC (water, 10 mM NH$_4$COOH, pH 3.7/ACN) to yield the desired compound.
MS (M+1): 556
Characteristic 1H NMR (dDMSO, 300 MHz) signals: 9.1 ppm (s, 1H); 8.7 ppm (m, 1H); 7.1 ppm (s, 1H); 3.5 ppm (s, 2H)

Example 79

6-Phenyl-5-(4-{[4-(5-pyridin-2-yl-1H-1,2,4-triazol-3-yl)piperidin-1-yl]methyl}phenyl)pyrazolo[1,5-a]pyrimidine-2-carboxylic acid 0.14 ml triethylamine are added to a solution of 101 mg 2-(5-piperidin-4H[1,2,4]triazol-3-yl)-pyridine*2HCl (prepared from tert-butyl 4-(hydrazinocarbonyl)piperidine-1-carboxylate and pyridine-2-carbonitrile according to a procedure described in U.S. Pat. No. 4,011,218 or WO2005100344) in 5 ml methanol. To this solution a solution of 150 mg 5-(4-formylphenyl)-6-phenylpyrazolo[1,5-a]pyrimidine-2-carboxylic acid (prepared as described under example 78) in 15 ml DMF is added, followed by 0.07 ml glacial acetic acid and 186 mg NaBH(OAc)$_3$. The resulting mixture is stirred at room temperature. Additional portions of 2 equivalents NaBH(OAc)$_3$ are added after 1, 2 and 3 hours. The solvent is removed by evaporation after 20 h and the residue is purified by RP HPLC (water, 10 mM NH$_4$COOH, pH 3.7/ACN) to yield the desired compound.
MS (M+1): 557
Characteristic 1H NMR (dDMSO, 300 MHz) signals: 9.2 ppm (s, 1H); 8.7 ppm (m, 1H); 7.1 ppm (s, 1H); 3.5 ppm (s, 2H);

Example 80

5-[4-({4-[3-(2-furyl)-1H-1,2,4-triazol-5-yl]piperidin-1-yl}methyl)phenyl]-2-methyl-6-phenyl[1,2,4]triazolo[1,5-a]pyrimidine Example 80 is synthesized in a manner according to example 37 by using 4-[5-(furan-2-yl)-1H-1,2,4-triazol-3-yl]piperidine instead of 2-(5-piperidin-[1,2,4]triazol-3-yl)-pyridine, which is synthesized from tert-butyl 4-(hydrazinocarbonyl)piperidine-1-carboxylate and 2-furonitrile according to a procedure described in U.S. Pat. No. 4,011,218 or WO2005100344.
MS (M+1): 517
Characteristic 1H NMR (dDMSO, 300 MHz) signals: 9.3 ppm (s, 1H); 7.8 ppm (m, 1H); 6.9 ppm (m, 1H); 6.6 ppm (m, 1H); 3.5 ppm (s, 2H); 2.6 ppm (s, 3H)

Example 81

5-[4-({4-[3-(2-furyl)-1H-1,2,4-triazol-5-yl]piperidin-1-yl}methyl)phenyl]-6-phenylpyrazolo[1,5-a]pyrimidine Example 81 is synthesized in a manner according to example 19 by using 4-[5-(furan-2-yl)-1H-1,2,4-triazol-3-yl]piperidine instead of 2-(5-piperidin-[1,2,4]triazol-3-yl)-pyridine, which is synthesized from tert-butyl 4-(hydrazinocarbonyl)piperidine-1-carboxylate and 2-furonitrile according to a procedure described in U.S. Pat. No. 4,011,218 or WO2005100344.
MS (M+1): 502
Characteristic 1H NMR (dDMSO, 300 MHz) signals: 9.1 ppm (s, 1H); 8.3 ppm (d, 1H); 7.8 ppm (m, 1H); 6.9 ppm (m, 1H); 6.7 ppm (d, 1H); 6.6 ppm (m, 1H); 3.5 ppm (s, 2H)

Example 82

7-[4-({4-[3-(2-furyl)-1H-1,2,4-triazol-5-yl]piperidin-1-yl}methyl)phenyl]-6-phenylimidazo[1,2-a]pyrimidine Example 82 is synthesized in a manner according to example 1 by using 4-[5-(furan-2-yl)-1H-1,2,4-triazol-3-yl]piperidine instead of 2-(5-piperidin-[1,2,4]triazol-3-yl)-pyridine, which is synthesized from tert-butyl 4-(hydrazinocarbonyl)piperidine-1-carboxylate and 2-furonitrile according to a procedure described in U.S. Pat. No. 4,011,218 or WO2005100344.
MS (M+1): 502
Characteristic 1H NMR (dDMSO, 300 MHz) signals: 9.0 ppm (s, 1H); 7.9 ppm (m, 1H); 6.9 ppm (m, 1H); 6.6 ppm (m, 1H)

Example 83

2-methyl-6-phenyl-5-(4-{[4-(3-phenyl-1H-1,2,4-triazol-5-yl)piperidin-1-yl]methyl}phenyl)[1,2,4]triazolo[1,5-a]pyrimidine Example 75 is synthesized in a manner according to example 37 by using 4-(5-phenyl-1H-1,2,4-triazol-3-yl)piperidine instead of 2-(5-piperidin-[1,2,4]triazol-3-yl)pyridine, which is prepared similar example 69 step 1 to step 5 by using benzonitril instead of 1H-pyrrole-2-carbonitrile

MS (M+1): 527

Characteristic 1H NMR (dDMSO, 300 MHz) signals: 9.3 ppm (s, 1H); 3.5 ppm (s, 2H); 2.6 ppm (s, 3H)

Example 84

7-[4-({4-[5-(4-methoxypyridin-2-yl)-1H-1,2,4-triazol-3-yl]piperidin-1-yl}methyl)phenyl]-6-phenylimidazo[1,2-a]pyrimidine Example 84 is synthesized in a manner according to example 1 by using 4-methoxy-2-(3-piperidin-4-yl-1H-1,2,4-triazol-5-yl)pyridine instead of 2-(5-piperidin-[1,2,4]triazol-3-yl)-pyridine, which is synthesized from tert-butyl 4-(hydrazinocarbonyl)piperidine-1-carboxylate and 4-methoxypyridine-2-carbonitrile according to a procedure described in U.S. Pat. No. 4,011,218 or WO2005100344.

MS (M+1): 543

Characteristic 1H NMR (dDMSO, 300 MHz) signals: 9.0 ppm (s, 1H); 8.5 ppm (m, 1H); 7.9 ppm (d, 1H); 7.8 ppm (d, 1H); 3.9 ppm (s, 3H); 3.5 ppm (s, 2H)

Example 85

6-phenyl-7-{4-[4-(5-pyridin-2-yl-1H-[1,2,4]triazol-3-yl)-piperidin-1-ylmethyl]-phenyl}-imidazo[1,2-a]pyrimidine Example 85 was prepared by analogy.
MS (M+1): 513.1
Characteristic 1H NMR (400 MHz, dDMSO) signals: 9.0 (s, 1H), 8.65 ppm (s, 1H)

COMMERCIAL UTILITY

The compounds of formula (I) and the stereoisomers of the compounds of formula (I) according to the invention are hereinafter referred to as the compounds of the invention. In particular, the compounds of the invention are pharmaceutically acceptable. The compounds according to the invention have valuable pharmaceutical properties, which make them commercially utilizable. In particular, they inhibit the Pi3K/Akt pathway and exhibit cellular activity. They are expected to be commercially applicable in the therapy of diseases (e.g. diseases dependent on overactivated Pi3K/Akt.

Cellular activity and analogous terms in the present invention is used as known to persons skilled in the art, as an example, induction of apoptosis or chemosensitization.

Chemosensitization and analogous terms in the present invention is used as known to persons skilled in the art. These stimuli include, for example, effectors of death receptor and survival pathways as well as cytotoxic/chemotherapeutic and targeted agents and finally radiation therapy. Induction of apoptosis and analogous terms according to the present invention are used to identify a compound which executes programmed cell death in cells contacted with that compound or in combination with other compounds routinely used for therapy.

Apoptosis in the present invention is used as known to persons skilled in the art. Induction of apoptosis in cells contacted with the compound of this invention might not necessarily be coupled with inhibition of cell proliferation. Preferably, the inhibition of proliferation and/or induction of apoptosis are specific to cells with aberrant cell growth.

Further on, the compounds according to the present invention inhibit protein kinase activity in cells and tissues, causing a shift towards dephosphorylated substrate proteins and as functional consequence, for example the induction of apoptosis, cell cycle arrest and/or sensitization towards chemotherapeutic and target-specific cancer drugs. In a preferred embodiment, inhibition of Pi3K/Akt pathway induces cellular effects as mentioned herein alone or in combination with standard cytotoxic or targeted cancer drugs.

Compounds according to the present invention exhibit anti-proliferative and/or pro-apoptotic and/or chemosensitizing properties. Accordingly, the compounds of the present invention are useful for treatment of hyperproliferative disorders, in particular cancer. Therefore the compounds of the present invention are used in the production of an anti-proliferative and/or pro-apoptotic and/or chemosensitizing effect in mammals such as human being suffering from a hyperproliferative disorders, like cancer.

Compounds according to the present invention exhibit anti-proliferative and/or pro-apoptotic properties in mammals such as humans due to inhibition of metabolic activity of cancer cells which are able to survive despite of unfavourable growth conditions such as glucose depletion, hypoxia or other chemo stress.

Thus, the compounds according to the present invention are for treating, ameliorating or preventing diseases of benign or malignant behaviour as described herein, such as e.g. for inhibiting cellular neoplasia.

Neoplasia in the present invention is used as known to persons skilled in the art. A benign neoplasia is described by hyperproliferation of cells, incapable of forming an aggressive, metastasizing tumor in-vivo. In contrast, a malignant neoplasia is described by cells with multiple cellular and biochemical abnormalities, capable of forming a systemic disease, for example forming tumor metastasis in distant organs.

The compounds according to the present invention can be preferably used for the treatment of malignant neoplasia. Examples of malignant neoplasia treatable with the compounds according to the present invention include solid and hematological tumors. Solid tumors can be exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasias include inherited cancers exemplified by Retinoblastoma and Wilms tumor. In addition, malignant neoplasias include primary tumors in said organs and corresponding secondary tumors in distant organs ("tumor metastases"). Hematological tumors can be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

It is noted that a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function and death.

Drug resistance is of particular importance for the frequent failure of standard cancer therapeutics. This drug resistance is caused by various cellular and molecular mechanisms. One aspect of drug resistance is caused by constitutive activation of anti-apoptotic survival signals with PKB/Akt as a key signalling kinase. Inhibition of the Pi3K/Akt pathway leads to a resensitization towards standard chemotherapeutic or target specific cancer therapeutics. As a consequence, the commercial applicability of the compounds according to the present invention is not limited to $1^{st}$ line treatment of cancer patients. In a preferred embodiment, cancer patients with resistance to cancer chemotherapeutics or target specific anti-cancer drugs are also amenable for treatment with these compounds for e.g. $2^{nd}$ or $3^{rd}$ line treatment cycles. In particular, the compounds according to the present invention might be used in combination with standard chemotherapeutic or targeted drugs to resensitize tumors towards these agents.

In the context of their properties, functions and utilities mentioned herein, the compounds according to the present invention are distinguished by unexpected valuable and desirable effects related therewith, such as e.g. superior therapeutic window, superior bioavailability (such as e.g. good oral absorption), low toxicity and/or further beneficial effects related with their therapeutic and pharmaceutical qualities.

Compounds according to the present invention are for treatment, prevention or amelioration of the diseases of benign and malignant behavior as described before, such as e.g. benign or malignant neoplasia, particularly cancer, especially a cancer that is sensitive to Pi3K/Akt pathway inhibition.

The present invention further includes a method for treating, prevention or amelioration mammals, including humans, which are suffering from one of the above-mentioned conditions, illnesses, disorders or diseases. The method is characterized in that a pharmacologically active and therapeutically effective and tolerable amount of one or more of compounds according to the present invention is administered to the subject in need of such treatment.

The present invention further includes a method for treating, preventing or ameliorating diseases responsive to inhibition of the Pi3K/Akt pathway, in a mammal, including human, comprising administering a pharmacologically active and therapeutically effective and tolerable amount of one or more of the compounds according to the present invention to said mammal.

The present invention further includes a method for treating hyperproliferative diseases of benign or malignant behaviour and/or disorders responsive to induction of apoptosis, such as e.g. cancer, particularly any of those cancer diseases described above, in a mammal, comprising administering a pharmacologically active and therapeutically effective and tolerable amount of one or more of the compounds according to the present invention to said mammal.

The present invention further includes a method for inhibiting cellular hyperproliferation or arresting aberrant cell growth in a mammal, comprising administering a pharmacologically active and therapeutically effective and tolerable amount of one or more of the compounds according to the present invention to said mammal.

The present invention further includes a method for inducing apoptosis in the therapy of benign or malignant neoplasia, particularly cancer, comprising administering a pharmacologically active and therapeutically effective and tolerable amount of one or more of the compounds according to the present invention to a subject in need of such therapy.

The present invention further includes a method for inhibiting protein kinase activity in cells comprising administering a pharmacologically active and therapeutically effective and tolerable amount of one or more of the compounds according to the present invention to a patient in need of such therapy.

The present invention further includes a method for sensitizing towards chemotherapeutic or target-specific anti-cancer agents in a mammal, comprising administering a pharmacologically active and therapeutically effective and tolerable amount of one or more of the compounds according to the present invention to said mammal.

The present invention further includes a method for treating benign and/or malignant neoplasia, particularly cancer, in a mammal, including human, comprising administering a pharmacologically active and therapeutically effective and tolerable amount of one or more of the compounds according to the present invention to said mammal.

The present invention further relates to the use of the compounds for the production of pharmaceutical compositions, which are employed for the treatment, prophylaxis, and/or amelioration of one or more of the illnesses mentioned.

The present invention further relates to the use of the compounds for the manufacture of pharmaceutical compositions for treating, preventing or ameliorating hyperproliferative diseases and/or disorders responsive to the induction of apoptosis, such as e.g. benign or malignant neoplasia, in particular cancer.

The present invention further relates to the use of the compounds according to this invention for the production of pharmaceutical compositions for treating, preventing or ameliorating benign or malignant neoplasia, particularly cancer, such as e.g. any of those cancer diseases described above.

The invention further relates to a compound according to the invention or a pharmaceutically acceptable salt thereof, for the treatment and/or prophylaxis of (hyper)proliferative diseases and/or disorders responsive to induction of apoptosis, which include benign neoplasia and malignant neoplasia, including cancer.

The invention further relates to a pharmaceutical composition, comprising a compound according to the invention or a pharmaceutically acceptable salt thereof, for the treatment and/or prophylaxis of (hyper)proliferative diseases and/or disorders responsive to induction of apoptosis, which include benign neoplasia and malignant neoplasia, including cancer.

The present invention further relates to the use of compounds and pharmaceutically acceptable salts according to the present invention for the manufacture of pharmaceutical compositions, which can be used for sensitizing towards chemotherapeutic and/or target specific anti-cancer agents.

The present invention further relates to the use of compounds according to the present invention for the manufacture of pharmaceutical compositions, which can be used for sensitizing towards radiation therapy of those diseases mentioned herein, particularly cancer.

The present invention further relates to the use of the compounds according to the present invention for the manufacture of pharmaceutical compositions, which can be used in the treatment of diseases sensitive to protein kinase inhibitor therapy and different to cellular neoplasia. These non-malignant diseases include, but are not limited to benign prostate hyperplasia, neurofibromatosis, dermatoses, and myelodysplastic syndromes.

The present invention further relates to pharmaceutical compositions comprising one or more of the compounds according to this invention and a pharmaceutically acceptable carrier or diluent.

The present invention further relates to pharmaceutical compositions comprising one or more of the compounds according to this invention and pharmaceutically acceptable auxiliaries and/or excipients.

The pharmaceutical compositions according to this invention are prepared by processes, which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, dragees, pills, cachets, granules, capsules, caplets, suppositories, patches (e.g. as TTS), emulsions (such as e.g. micro-emulsions or lipid emulsions), suspensions (such as e.g. nano suspensions), gels, solubilisates or solutions (e.g. sterile solutions), or encapsulated in liposomes or as beta-cyclodextrine or beta-cyclodextrin derivative inclusion complexes or the like, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers (such as e.g. polyoxyethylenglyceroltriricinoleat 35, PEG 400, Tween 80, Captisol, Solutol HS15 or the like), colorants, complexing agents, permeation promoters, stabilizers, fillers, binders, thickeners, disintegrating agents, buffers, pH regulators (e.g. to obtain neutral, alkaline or acidic formulations), polymers, lubricants, coating agents, propellants, tonicity adjusting agents, surfactants, flavorings, sweeteners or dyes, can be used.

In particular, auxiliaries and/or excipients of a type appropriate to the desired formulation and the desired mode of administration are used.

The administration of the compounds, pharmaceutical compositions or combinations according to the invention may be performed in any of the generally accepted modes of administration available in the art. Illustrative examples of suitable modes of administration include intravenous, oral, nasal, parenteral, topical, trans-dermal and rectal delivery. Oral and intravenous deliveries are preferred.

Generally, the pharmaceutical compositions according to the invention can be administered such that the dose of the active compound is in the range customary for Pi3K/Akt pathway inhibitors. In particular, a dose in the range of from 0.01 to 4000 mg of the active compound per day is preferred for an average adult patient having a body weight of 70 kg. In this respect, it is to be noted that the dose is dependent, for example, on the specific compound used, the species treated, age, body weight, general health, sex and diet of the subject treated, mode and time of administration, rate of excretion, severity of the disease to be treated and drug combination.

The pharmaceutical composition can be administered in a single dose per day or in multiple subdoses, for example, 2 to 4 doses per day. A single dose unit of the pharmaceutical composition can contain e.g. from 0.01 mg to 4000 mg, preferably 0.1 mg to 2000 mg, more preferably 0.5 to 1000 mg, most preferably 1 to 500 mg, of the active compound. Furthermore, the pharmaceutical composition can be adapted to weekly, monthly or even more infrequent administration, for example by using an implant, e.g. a subcutaneous or intramuscular implant, by using the active compound in form of a sparingly soluble salt or by using the active compound coupled to a polymer.

The choice of the optimal dosage regime and duration of medication, particularly the optimal dose and manner of administration of the active compounds necessary in each case can be determined by a person skilled in the art.

The present invention further relates to combinations comprising one or more first active ingredients selected from the compounds of the invention and one or more second active ingredients selected from chemotherapeutic anti-cancer agents and target-specific anti-cancer agents e.g. for treating, preventing or ameliorating diseases responsive or sensitive to inhibition of the Pi3K/Akt pathway, such as hyperproliferative diseases of benign or malignant behaviour and/or disorders responsive to the induction of apoptosis, particularly cancer, such as e.g. any of those cancer diseases described above.

The invention further relates to the use of a pharmaceutical composition comprising one or more of the compounds according to this invention as sole active ingredient(s) and a pharmaceutically acceptable carrier or diluent in the manufacture of pharmaceutical products for the treatment and/or prophylaxis of the illnesses mentioned above.

Depending upon the particular disease, to be treated or prevented, additional therapeutic active agents, which are normally administered to treat or prevent that disease, may optionally be coadministered with the compounds according to this invention. As used herein, additional therapeutic agents that are normally administered to treat or prevent a particular disease are known as appropriate for the disease being treated.

The above mentioned second active ingredient, which is a chemotherapeutic anti-cancer agents, includes but is not limited to (i) alkylating/carbamoylating agents such as Cyclophosphamid (Endoxan®), Ifosfamid (Holoxan®), Thiotepa (Thiotepa Lederle®), Melphalan (Alkeran®), or chloroethylnitrosourea (BCNU); (ii) platinum derivatives like cis-platin (Platinex® BMS), oxaliplatin (Eloxatin®), satraplatin or carboplatin (Cabroplat® BMS); (iii) antimitotic agents/tubulin inhibitors such as vinca alkaloids (vincristine, vinblastine, vinorelbine), taxanes such as Paclitaxel (Taxol®), Docetaxel (Taxotere®) and analogs as well as new formulations and conjugates thereof (like the nanoparticle formulation Abraxane® with paclitaxel bound to albumin), epothilones such as Epothilone B (Patupilone®), Azaepothilone (Ixabepilone®) or ZK-EPO, a fully synthetic epothilone B analog; (iv) topoisomerase inhibitors such as anthracyclines (exemplified by Doxorubicin/Adriblastin®), epipodophyllotoxines (exemplified by Etoposide/Etopophos®) and camptothecin and camptothecin analogs (exemplified by Irinotecan/Camptosar® or Topotecan/Hycamtin®); (v) pyrimidine antagonists such as 5-fluorouracil (5-FU), Capecitabine (Xeloda®), Arabinosylcytosine/Cytarabin (Alexan®) or Gemcitabine (Gemzar®); (vi) purin antagonists such as 6-mercaptopurine (Puri-Nethol®), 6-thioguanine or fludarabine (Fludara®) and (vii) folic acid antagonists such as methotrexate (Farmitrexat®) or premetrexed (Alimta®).

The above mentioned second active ingredient, which is a target specific anti-cancer agent, includes but is not limited to (i) kinase inhibitors such as e.g. Imatinib (Glivec®), ZD-1839/Gefitinib (Iressa®), Bay43-9006 (Sorafenib, Nexavar®), SU11248/Sunitinib (Sutent®), OSI-774/Erlotinib (Tarceva®), Dasatinib (Sprycel®), Lapatinib (Tykerb®), or, see also below, Vatalanib, Vandetanib (Zactima®) or Pazopanib; (ii) proteasome inhibitors such as PS-341/Bortezumib (Velcade®); (iii) histone deacetylase inhibitors like SAHA (Zolinza®), PXD101, MS275, MGCD0103, Depsipeptide/FK228, NVP-LBH589, Valproic acid (VPA), CRA/PCI-24781, ITF2357, SB939 and butyrates (iv) heat shock protein 90 inhibitors like 17-allylaminogeldanamycin (17-AAG) or 17-dimethylaminogeldanamycin (17-DMAG); (v) vascular targeting agents (VTAs) like combretastin A4 phosphate or AVE8062/AC7700 and anti-angiogenic drugs like the VEGF antibodies, such as Bevacizumab (Avastin®), or KDR tyrosine kinase inhibitors such as PTK787/ZK222584 (Vatalanib®) or Vandetanib (Zactima®) or Pazopanib; (vi) monoclonal antibodies such as Trastuzumab (Herceptin®), Rituximab (MabThera/Rituxan®), Alemtuzumab (Campath®), Tositumomab (Bexxar®), C225/Cetuximab (Erbitux®), Avastin (see above) or Panitumumab (Vectibix®) as well as mutants and conjugates of monoclonal antibodies, e.g. Gemtuzumab ozogamicin (Mylotarg®) or Ibritumomab tiuxetan (Zevalin®), and antibody fragments; (vii) oligonucleotide based therapeutics like G-3139/Oblimersen (Genasense®) or the DNMT1 inhibitor MG98; (viii) Toll-like receptor/TLR 9 agonists like Promune®, TLR 7 agonists like Imiquimod (Aldara®) or Isatoribine and analogues thereof, or TLR 7/8 agonists like Resiquimod as well as immunostimulatory RNA as TLR 7/8 agonists; (ix) protease inhibitors; (x) hormonal therapeutics such as anti-estrogens (e.g. Tamoxifen or Raloxifen), anti-androgens (e.g. Flutamide or Casodex), LHRH analogs (e.g. Leuprolide, Goserelin or Triptorelin) and aromatase inhibitors (e.g. Femara, Arimedex or Aromasin).

Other target specific anti-cancer agents includes bleomycin, retinoids such as all-trans retinoic acid (ATRA), DNA methyltransferase inhibitors such as 5-Aza-2'-deoxycytidine (Decitabine, Dacogen®) and 5-azacytidine (Vidaza®), alanosine, cytokines such as interleukin-2, interferons such as interferon α2 or interferon-γ, bcl2 antagonists (e.g. ABT-737 or analogs), death receptor agonists, such as TRAIL, DR4/5 agonistic antibodies, FasL and TNF-R agonists (e.g. TRAIL receptor agonists like mapatumumab or lexatumumab).

Specific examples of the second active ingredient include, but is not limited 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BEVACIZUMAB, BEXXAR, BICALUTAMIDE, BLEOMYCIN, BORTEZOMIB, BROXURIDINE, BUSULFAN, CAMPATH, CAPECITABINE, CARBOPLATIN, CARBOQUONE, CARMUSTINE, CETRORELIX, CHLORAMBUCIL, CHLORMETHINE, CISPLATIN, CLADRIBINE, CLOMIFENE, CYCLOPHOSPHAMIDE, DACARBAZINE, DACLIZUMAB, DACTINOMYCIN, DASATINIB, DAUNORUBICIN, DECITABINE, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ERLOTINIB, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GENASENSE, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, IXABEPILONE, LANREOTIDE, LAPATINIB, LETROZOLE, LEUPRORELIN, LOBAPLATIN, LOMUSTINE, LUPROLIDE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, MYLOTARG, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PANITUMUMAB, PATUPILONE, PAZOPANIB, PEGASPARGASE, PEGFILGRASTIM, PEMETREXED, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALOXIFEN, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLIMUS, SOBUZOXANE, SORAFENIB, SPIROMUSTINE, STREPTOZOCIN, SUNITINIB, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRAIL, TRASTUZUMAB, TREOSULFAN, TRIAZIQUONE, TRIMETREXATE, TRIPTORELIN, TROFOSFAMIDE, UREDEPA, VALRUBICIN, VATALANIB, VANDETANIB, VERTEPORFIN, VINBLASTINE, VINCRISTINE, VINDESINE, VINORELBINE, VOROZOLE, ZEVALIN and ZOLINZA.

The anti-cancer agents mentioned herein above as combination partners of the compounds according to this invention are meant to include pharmaceutically acceptable derivatives thereof, such as e.g. their pharmaceutically acceptable salts.

The person skilled in the art is aware of the total daily dosage(s) and administration form(s) of the additional therapeutic agent(s) coadministered. Said total daily dosage(s) can vary within a wide range.

In practicing the present invention, the compounds according to this invention may be administered in combination therapy separately, sequentially, simultaneously, concurrently or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics (chemotherapeutic and/or target specific anti-cancer agents), in particular art-known anti-cancer agents, such as any of e.g. those mentioned above.

In this context, the present invention further relates to a combination comprising a first active ingredient, which is at least one compound according to this invention, and a second active ingredient, which is at least one art-known anti-cancer agent, such as e.g. one or more of those mentioned herein above, for separate, sequential, simultaneous, concurrent or chronologically staggered use in therapy, such as e.g. in therapy of any of those diseases mentioned herein.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The present invention further relates to a pharmaceutical composition comprising a first active ingredient, which is at least one compound according to this invention, and a second active ingredient, which is at least one art-known anti-cancer agent, such as e.g. one or more of those mentioned herein above, and, optionally, a pharmaceutically acceptable carrier or diluent, for separate, sequential, simultaneous, concurrent or chronologically staggered use in therapy.

The present invention further relates to a combination product comprising a.) at least one compound according to this invention formulated with a pharmaceutically acceptable carrier or diluent, and b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a compound according to this invention, and a pharmaceutically acceptable carrier or diluent; a preparation of a second active ingredient, which is an art-known anti-cancer agent, such as one of those mentioned above, and a pharmaceutically acceptable carrier or diluent; for simultaneous, concurrent, sequential, separate or chronologically staggered use in therapy. Optionally, said kit comprises instructions for its use in therapy, e.g. to treat hyperproliferative diseases and diseases responsive or sensitive to inhibition of the Pi3K/Akt pathway, such as e.g. benign or malignant neoplasia, particularly cancer, more precisely, any of those cancer diseases described above.

The present invention further relates to a combined preparation comprising at least one compound according to this invention and at least one art-known anti-cancer agent for simultaneous, concurrent, sequential or separate administration.

The present invention further relates to combinations, compositions, formulations, preparations or kits according to the present invention having Pi3K/Akt pathway inhibitory activity.

In addition, the present invention further relates to a method for treating in combination therapy hyperproliferative diseases and/or disorders responsive to the induction of apoptosis, such as e.g. cancer, in a patient comprising administering a combination, composition, formulation, preparation or kit as described herein to said patient in need thereof.

In addition, the present invention further relates to a method for treating hyperproliferative diseases of benign or malignant behaviour and/or disorders responsive to the induction of apoptosis, such as e.g. cancer, in a patient comprising administering in combination therapy separately, simultaneously, concurrently, sequentially or chronologically staggered a pharmaceutically active and therapeutically effective and tolerable amount of a pharmaceutical composition, which comprises a compound according to this invention and a pharmaceutically acceptable carrier or diluent, and a pharmaceutically active and therapeutically effective and tolerable amount of one or more art-known anti-cancer agents, such as e.g. one or more of those mentioned herein, to said patient in need thereof.

In further addition, the present invention relates to a method for treating, preventing or ameliorating hyperproliferative diseases and/or disorders responsive to induction of apoptosis, such as e.g. benign or malignant neoplasia, e.g. cancer, particularly any of those cancer diseases mentioned herein, in a patient comprising administering separately, simultaneously, concurrently, sequentially or chronologically staggered to said patient in need thereof an amount of a first active compound, which is a compound according to the present invention, and an amount of at least one second active compound, said at least one second active compound being a standard therapeutic agent, particularly at least one art-known anti-cancer agent, such as e.g. one or more of those chemotherapeutic and target-specific anti-cancer agents mentioned herein, wherein the amounts of the first active compound and said second active compound result in a therapeutic effect.

In yet further addition, the present invention relates to a method for treating, pre-venting or ameliorating hyperproliferative diseases and/or disorders responsive to induction of apoptosis, such as e.g. benign or malignant neoplasia, e.g. cancer, particularly any of those cancer diseases mentioned herein, in a patient comprising administering a combination according to the present invention.

In addition, the present invention further relates to the use of a composition, combination, formulation, preparation or kit according to this invention in the manufacture of a pharmaceutical product, such as e.g. a commercial package or a medicament, for treating, preventing or ameliorating hyperproliferative diseases, such as e.g. cancer, and/or disorders responsive to the induction of apoptosis, particularly those diseases mentioned herein, such as e.g. malignant or benign neoplasia.

The present invention further relates to a commercial package comprising one or more compounds of the present invention together with instructions for simultaneous, concurrent, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, concurrent, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, concurrent, sequential or separate use with one or more compounds according to the present invention.

The compositions, combinations, preparations, formulations, kits or packages mentioned in the context of the combination therapy according to this invention may also include more than one of the compounds according to this invention and/or more than one of the art-known anti-cancer agents mentioned.

The first and second active ingredient of a combination or kit-of-parts according to this invention may be provided as separate formulations (i.e. independently of one another), which are subsequently brought together for simultaneous, concurrent, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a combination or kit-of-parts according to this invention can be according, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a hyperproliferative diseases and/or a disorder responsive to the induction of apoptosis, particularly one of those diseases mentioned herein, such as e.g. malignant or benign neoplasia, especially cancer, like any of those cancer diseases mentioned herein.

In addition, compounds according to the present invention can be used in the pre- or post-surgical treatment of cancer.

In further addition, compounds of the present invention can be used in combination with radiation therapy.

A combination according to this invention can refer to a composition comprising both the compound(s) according to this invention and the other active anti-cancer agent(s) in a fixed combination (fixed unit dosage form), or a medicament pack comprising the two or more active ingredients as discrete separate dosage forms (non-fixed combination). In case of a medicament pack comprising the two or more active ingredients, the active ingredients are preferably packed into blister cards, which are suited for improving compliance.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

Biological Investigations

Cellular PI3K/Akt Pathway Assay

In order to study the cellular activity of the compounds according to the present invention, an Enzyme Linked Immunosorbent Assay (ELISA)-based assay has been used specific phospho-AKT. The assay is based on a Sandwich ELISA kit (PathScan™ Phospho-Akt1 (Ser473); Cell Signaling, USA; #7160). The ELISA Kit detects endogenous levels of phosphorylated Akt protein. A phospho-Akt (Ser473) antibody (Cell Signaling, USA; #9271) has been coated onto the microwells. After incubation with cell lysates, the coated antibody captures the phosphorylated Akt protein. Following extensive washing, Akt1 monoclonal antibody (Cell Signaling, USA; #2967) is added to detect the captured phospho-Akt1 protein. HRP-linked anti-mouse antibody (HRP: horseradish peroxidase; Cell Signaling, USA; #7076) is then used to recognize the bound detection antibody. HRP substrate (=3,3',5,5'-tetramethylbenzidine (TMB); Cell Signaling, USA; #7160) is added to develop colour. The magnitude of optical density for this developed color is proportional to the quantity of phosphorylated Akt protein.

MCF7 cells (ATCC HTB-22) are seeded into 96 well fate bottom plates at a density of 10000 cells/well. 24 hours after seeding, the cells are serum starved using low-serum medium (IMEM media including 0.1% charcoal treated FCS (FCS: fetal calf serum)). After 24 hours 1 µl each of the compound dilutions (test compounds were dissolved as 10 mM solutions in dimethylsulfoxide (DMSO) and subsequently diluted) are added into each well of the 96 well plates and incubated for 48 h at 37° C. in a humidified atmosphere containing 5% $CO_2$. To stimulate Akt phosphorylation, β-Heregulin (20 ng/ml β-HRG) is added in parallel to the compounds. Wells containing unstimulated control cells (no β-Heregulin stimulation) are incubated with or without the diluted compound. Wells containing untreated control cells (no compound) are filled with medium containing 0.5% v:v DMSO and are or are not stimulated with β-Heregulin.

Cells are harvested and lysed with brief sonification in 1× cell lysis buffer (20 mM Tris (pH7.5), 150 mM NaCl, 1 mM ethylene diaminetetraacetate (EDTA), 1 mM ethylene glycol-bis(2-aminoethyl)-N,N,N',N'-tetraacetic acid (EGTA), 1 vol % Triton X-100, 2.5 mM sodium pyrophosphate, 1 mM β-glycerolphosphate, 1 mM $Na_3VO_4$, 1 µg/ml leupeptin). The lysate is centrifuged for 10 min. at 4° C. and the supernatant is transferred to a new tube. 100 µl of sample diluent (0.1 vol % Tween-20, 0.1 vol % sodium azide in phosphate buffered saline (PBS)) are added to a microcentrifuge tube and 100 µl of cell lysate are transferred into the tube and vortexed. 100 µl of each diluted cell lysate are added to the appropriate ELISA well, and incubated overnight at 4° C. The plates are washed 4 times with 1× wash buffer (1 vol % tween-20, 0.33 vol % thymol, in PBS). Next 100 µl of detection antibody (Akt1 (2H10) monoclonal detection antibody; Cell Signaling, USA; #2967) are added to each well and incubation continued for 1 h at 37° C. The washing procedure is repeated between each step. 100 µl of secondary antibody (anti-mouse IgG HRP-linked antibody; Cell Signaling, USA; #7076) are added to each well and incubated for 30 min. at 37° C. Than, 100 µl of TMB substrate (0.05% 3,3',5,5' tetramethylbenzidine, 0.1% hydrogen peroxide, complex polypeptides in a buffered solution; Cell Signaling, USA; #7160) are added to each well and incubated for 30 min. at 25° C. Finally 100 µl of STOP solution (0.05 vol % α and β unsaturated carbonyl compound) are added to each well and the plate are shaked gently. The absorbance is measured at λ=450 nm (Wallac Victor2; Perkin Elmer, USA) within 30 min. after adding the STOP solution. The analysis of the data is performed using a statistical program (Excel; Microsoft, USA). Preferred compounds show an inhibitory activity towards Akt phosphorylation below 10 μM.

Cellular pGSK3 Assay:

In order to study the cellular activity of the compounds according to the present invention, an ELISA-based assay has been established for the phosphorylated protein glycogen synthetase kinase 3 (GSK3). The assay is based on a solid phase sandwich ELISA that detects endogenous levels of phosphorylated GSK3 using a phospho-GSK3 (Ser9) specific antibody (BioSource International, Inc.; Catalog #KHO0461). After incubation with cell lysates, the coated antibody captures the phosphorylated GSK3 protein. Following extensive washing, GSK3 polyclonal antibody is added to detect the captured phospho-GSK3 protein. Secondary antibody (anti-rabbit IgG-HRP) is then used to recognize the bound detection antibody. After the second incubation and washing to remove all the excess anti-rabbit IgG-HRP, a substrate solution is added, which is acted upon by the bound enzyme to produce color. The intensity of this colored product is directly proportional to the concentration of GSK-3β [pS9] present in the original specimen.

MCF7 cells (ATCC HTB-22) were seeded into 96 well fate bottom plates at a density of 10000 cells/well. After 24 h 1 μl each of the compound dilutions (test compounds were dissolved as 10 mM solutions in dimethylsulfoxide (DMSO) and subsequently diluted) were added into each well of the 96 well plates and incubated for 48 h at 37° C. in a humidified atmosphere containing 5% $CO_2$.

Cells were harvested and lysed in cell extraction buffer (10 mM Tris, pH 7.4, 100 mM NaCl, 1 mM EDTA, 1 mM EGTA, 1 mM NaF, 20 mM $Na_4P_2O_7$, 2 mM $Na_3VO_4$, 1% Triton X-100, 10 vol % glycerol, 0.1 vol % SDS, 0.5 vol % deoxycholate, 1 mM phenylmethylsulfonylfluoride (PMSF)). The lysate were centrifuged for 10 min. at 4° C. and the supernatant were transferred to a new tube. 50 μl of sample diluent (standard diluent buffer, Biosource) were added and 100 μl of cell lysate transferred into the tube and vortexed. 100 μl of each diluted cell lysate were added to the appropriate ELISA well plate and incubated for 3 h at room temperature. The plates were washed 4 times with 1× wash buffer (Biosource). 50 μl of detection antibody (GSK3 (Ser9) detection antibody; BioSource) were added to each well and incubated for 30 min. at room temperature. The washing procedure was repeated between each step. 100 μl of HRP-linked secondary antibody (anti-mouse IgG HRP-linked antibody) were added to each well and incubated for 30 min. at room temperature. 100 μl of TMB substrate (0.05 vol % 3,3',5,5' tetramethylbenzidine, 0.1 vol % hydrogen peroxide, complex polypeptides in a buffered solution; Biosource) were added to each well and incubated for 30 min. at room temperature. Finally 100 μl of Stop solution (0.05 vol % α and β unsaturated carbonyl compound) were added to each well and the plate were shaked gently for a few seconds. The absorbance was measured at λ=450 nm (Wallac Victor2; Perkin Elmer, USA) within 30 min. after adding the stop solution.

The analysis of the data was performed using a statistical program (Excel; Microsoft, USA) and the IC50 of pGSK3 inhibition was determined.

TABLE

Cellular PI3K/Akt pathway inhibition - Cellular pGSK3 assay

| Example No. | Cellular PI3K/Akt pathway assay | Cellular pGSK3 pathway assay |
|---|---|---|
| 1 | +++ | +++ |
| 2 | +++ | ++ |
| 3 | +++ | ++ |
| 4 | +++ | ++ |
| 5 | +++ | ++ |
| 6 | +++ | ++ |
| 7 | +++ | +++ |
| 8 | +++ | ++ |
| 9 | +++ | ++ |
| 10 | ++ | +++ |
| 11 | +++ | +++ |
| 12 | +++ | ++ |
| 13 | +++ | ++ |
| 14 | +++ | ++ |
| 15 | +++ | ++ |
| 16 | +++ | +++ |
| 17 | +++ | ++ |
| 18 | ++ | ++ |
| 19 | +++ | ++ |
| 20 | +++ | ++ |
| 21 | +++ | ++ |
| 22 | +++ | ++ |
| 23 | +++ | + |
| 24 | +++ | ++ |
| 25 | +++ | + |
| 26 | +++ | |
| 27 | + | ++ |
| 28 | | ++ |
| 29 | | ++ |
| 30 | +++ | +++ |
| 31 | +++ | +++ |
| 32 | +++ | +++ |
| 33 | +++ | ++ |
| 34 | +++ | ++ |
| 35 | +++ | ++ |
| 36 | +++ | +++ |
| 37 | | |
| 38 | | |
| 39 | +++ | |
| 40 | +++ | +++ |
| 41 | | |
| 42 | | |
| 43 | | |
| 44 | | |
| 45 | +++ | |
| 46 | | |
| 47 | | |
| 48 | | |
| 49 | +++ | |
| 50 | +++ | |
| 51 | | |
| 52 | | |
| 53 | | |
| 54 | | |
| 55 | | |
| 56 | | |
| 57 | | |
| 58 | | |
| 59 | | |
| 60 | | |
| 61 | | |
| 62 | | |
| 63 | | |
| 64 | | |
| 65 | | |
| 66 | | |
| 67 | | |
| 68 | | |
| 69 | | |
| 70 | | |
| 71 | | |
| 72 | | |
| 73 | | |
| 74 | | |

TABLE-continued

Cellular PI3K/Akt pathway inhibition - Cellular pGSK3 assay

| Example No. | Cellular PI3K/Akt pathway assay | Cellular pGSK3 pathway assay |
|---|---|---|
| 75 | | |
| 76 | | |
| 77 | | |
| 78 | | |
| 79 | | |
| 80 | | |
| 81 | | |
| 82 | | |
| 83 | | |
| 84 | | |
| 85 | | |

IC50 > 10 μM +
10 μM > IC50 > 1 μM ++
1 μM > IC50 +++

Cellular Proliferation/Cytotoxicity Assay:

The anti-proliferative activity of the compounds as described herein, is evaluated using the OvCAR3, HCT116 and A549 cell lines and the Alamar Blue (Resazurin) cell viability assay (O'Brien et al. Eur J Biochem 267, 5421-5426, 2000). Resazurin is reduced to the fluorescent resorufin by cellular dehydrogenase activity, correlating with viable, proliferating cells. Test compounds are dissolved as 10 mM solutions in DMSO and subsequently diluted. Cells like HCT116 or A549 cells were seeded into 96 well flat bottom plates at a density of 10000 cells/well (OvCAR3 cells), 1000 cells/well (HCT116 cells) or 2000 cells/well (A549 cells) in a volume of 200 μl/well. 24 hours after seeding, 1 μl each of the compound dilutions are added into each well of the 96 well plates. Each compound dilution is tested as at least as duplicates. Wells containing untreated control cells were filled with 200 μl DMEM (Dulbecco's Modified Eagle Medium) containing 0.5 vol % v:v DMSO. The cells are then incubated with the substances for 72 h at 37° C. in a humidified atmosphere containing 5 vol % CO2. To determine the viability of the cells, 20 μl of a Resazurin solution (90 mg/l) are added. After 4 h incubation at 37° C., the fluorescence is measured by extinction at λ=544 nm and an emission of λ=590 nm (Wallac Victor2; Perkin Elmer, USA). For the calculation of the cell viability, the emission value from untreated cells is set as 100% viability and the fluorescence intensity of treated cells are set in relation to the values of untreated cells. Viabilities are expressed as % values. The corresponding IC50 values of the compounds for cytotoxic activity are determined from the concentration-effect curves by means of non-linear regression. The analysis of the data is performed using a biostatistical program (GraphPad Prism, USA).

Representative IC50 values for anti-proliferative/cytotoxic potency determined in the aforementioned assay follow from the following table, in which the numbers of the compound correspond to the numbers of the examples.

TABLE

Anti-proliferative/Cytotoxic activity (OvCAR3 cells and A549 cells)

| Example No. | Anti-proliferative/ Cytotoxic activity (A549 cells) | Anti-proliferative/ Cytotoxic activity (OvCAR3 cells) |
|---|---|---|
| 1 | + | ++ |
| 2 | + | ++ |
| 3 | ++ | ++ |
| 4 | ++ | ++ |
| 5 | ++ | ++ |
| 6 | ++ | ++ |
| 7 | + | ++ |
| 8 | + | ++ |
| 9 | + | ++ |
| 10 | + | ++ |
| 11 | + | ++ |
| 12 | ++ | ++ |
| 13 | ++ | ++ |
| 14 | ++ | ++ |
| 15 | + | ++ |
| 16 | + | ++ |
| 17 | ++ | ++ |
| 18 | + | ++ |
| 19 | + | ++ |
| 20 | + | ++ |
| 21 | + | ++ |
| 22 | + | ++ |
| 23 | + | |
| 24 | + | |
| 25 | + | |
| 26 | ++ | |
| 27 | | |
| 28 | ++ | |
| 29 | + | |
| 30 | ++ | |
| 31 | ++ | |
| 32 | + | |
| 33 | ++ | |
| 34 | ++ | |
| 35 | ++ | |
| 36 | ++ | |
| 37 | ++ | |
| 38 | | |
| 39 | ++ | |
| 40 | ++ | |
| 41 | ++ | |
| 42 | ++ | |
| 43 | ++ | |
| 44 | + | |
| 45 | + | |
| 46 | + | |
| 47 | ++ | |
| 48 | ++ | |
| 49 | ++ | |
| 50 | ++ | |
| 51 | ++ | |
| 52 | ++ | |
| 53 | ++ | |
| 54 | ++ | |
| 55 | ++ | |
| 56 | ++ | |
| 57 | ++ | |
| 58 | ++ | |
| 59 | ++ | |
| 60 | ++ | |
| 61 | ++ | |
| 62 | ++ | |
| 63 | + | |
| 64 | ++ | |
| 65 | ++ | |
| 66 | ++ | |
| 67 | ++ | |
| 68 | ++ | |
| 69 | + | |
| 70 | + | |
| 71 | + | |
| 72 | ++ | |
| 73 | ++ | |
| 74 | ++ | |

TABLE-continued

Anti-proliferative/Cytotoxic activity
(OvCAR3 cells and A549 cells)

| Example No. | Anti-proliferative/ Cytotoxic activity (A549 cells) | Anti-proliferative/ Cytotoxic activity (OvCAR3 cells) |
|---|---|---|
| 75 | ++ | |
| 76 | + | |
| 77 | ++ | |
| 78 | + | |
| 79 | ++ | |
| 80 | + | |
| 81 | ++ | |
| 82 | + | |
| 83 | + | |
| 84 | ++ | |
| 85 | + | |

IC50 > 10 µM +
10 µM > IC50 ++

Chemosensitization Assay

The herein disclosed compounds are evaluated for the ability to sensitize cancer cells towards apoptotic stimuli. Inhibitors of Akt are tested alone and in combination with chemotherapeutic and targeted cancer therapeutics to determine the effect on apoptosis induction.

Cancer cells are seeded in 96 well plates at concentrations ranging from $2 \times 10^3$ to $1 \times 10^4$ cells per well in their respective growth media. 48-72 hours later, the apoptosis assay are set up as follows:

For combination assays with a chemotherapeutic agent especially preferred topoisomerase inhibitors (such as doxorubicin, etoposide, camptothecin or mitoxantrone) or antimitotic agents/tubulin inhibitors (such as vincristine), compounds are added at respective concentrations indicated and plates incubated at 37° C. in a $CO_2$ incubator for 18 hours. For standard combination assays utilizing treatment with chemotherapeutic agent are added at the same time at the respective concentrations indicated.

For combinations assays involving addition of targeted pro-apoptotic agents like the death receptor ligand TRAIL/Apo2L (Research Diagnostics) compounds are added for 1.5 hours prior to addition of TRAIL and plates incubated an additional 3 to 4 hours post TRAIL addition. In the case of the time course, plates are incubated for 2, 3, 4 and 6 hours with TRAIL ligand before ending the assay. For both procedures, total final volumes do not exceed 250 µl. At the end of the incubation time, the cells are pelleted by centrifugation (200× g; 10 min. at RT) and the supernatant is discarded. The cells are resuspended and incubated using lysis buffer for 30 min. at RT (Cell Death Detection ELISA$^{PLUS}$, Roche, Cat. No. 11774425001). After the centrifugation is repeated (200×g; 10 min. at RT) an aliquot of the supernatant is transferred to a streptavidin-coated well of a microplate. Followed by the incubation (2 h, RT) and binding of nucleosomes in the supernatant with, anti-histone antibody (biotin-labeled) and anti-DNA antibody (peroxidase-conjugated; Cell Death Detection ELISA$^{PLUS}$, Roche, Cat. No. 11774425001). The antibody-nucleosome complexes are bound to the microplate. The immobilized antibody-histone complexes are washed three times at RT to remove cell components that are not immunoreactive. The substrate solution (2,2'-AZINO-bis[3-ethyl-benziazoline-6-sulfonic acid (ABTS); Cell Death Detection ELISA$^{PLUS}$, Roche, Cat. No. 11 774 425 001) is added and the samples were incubated for 15 min., RT. The amount of colored product is determined spectrophotometrically (absorbance at λ=405 nm). Data are expressed as percent activity of control with cisplatin used as a positive control. Apoptosis induction by 50 µM cisplatin is arbitrarily defined as 100 cisplatin units (100 CPU).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding Indian application No. 1572/MUM/2007, filed Aug. 14, 2007, and of corresponding European application No. 07 118 736.3-2117, filed Oct. 18, 2007, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula (I)

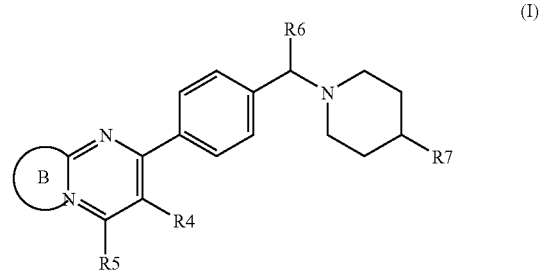

wherein ring B and the pyrimidine to which it is fused form a ring system selected from the group consisting of

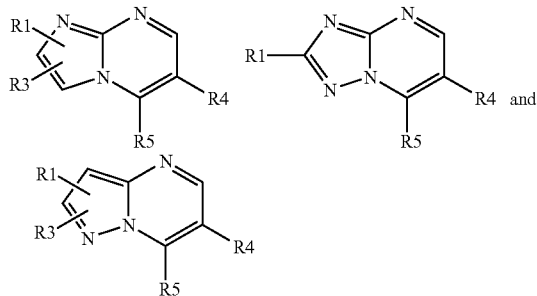

wherein
R1 is hydrogen, 1-4C-alkyl, halogen, amino, 1-4G-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl, R2 is hydrogen or 1-4C-alkyl,
R3 is hydrogen, 1-4C-alkyl or halogen,
R4 is phenyl or thienyl,
R5 is hydrogen, 1-4C-alkoxy, amino, mono- or di-1-4C-alkylamino, 1-4C-alkyl or 3-7C-cycloalkyl,
R6 is hydrogen or 1-4C-alkyl,
R7 is —W—Y,
W is a monocyclic 5-membered heteroarylene comprising 1 nitrogen atom and optionally 1 or 2 further heteroatoms independently selected from the group consisting of oxygen, nitrogen and sulphur,
and wherein the heteroarylene is optionally substituted by R8,
R8 is 1-4C-alkyl or 3-7C-cycloalkyl,
Y is phenyl or a monocyclic 5 or 6 membered heteroaryl comprising 1 nitrogen oxygen or sulfur atom and optionally 1 or 2 further heteroatoms independently selected from the group consisting of oxygen, nitrogen and sulphur,
and wherein the heteroaryl is optionally substituted by R9,
R9 is 1-4C-alkyl, 1-4C-alkoxy or halogen,
or a salt, a tautomer, or a stereoisomer thereof, or a salt of said tautomer or said stereoisomer.

2. The compound according to claim 1, wherein ring B and the pyrimidine to which it is fused form a ring system selected from the group consisting of

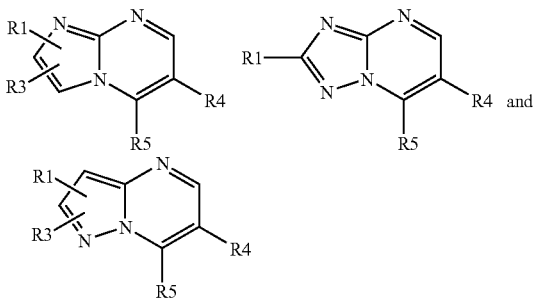

wherein
R1 is hydrogen, 1-4C-alkyl, halogen, amino, 1-4C-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl,
R2 is hydrogen or 1-4C-alkyl,
R3 is hydrogen,
R4 is phenyl or thienyl,
R5 is hydrogen, 1-4C-alkoxy, amino, mono- or di-1-4C-alkylamino, 1-4C-alkyl or 3-7C—cycloalkyl,
R6 is hydrogen or 1-4-C-alkyl,
R7 is —W—Y,
W is triazolylene, pyrazolylene or imidazolylene,
each of which is optionally substituted by R8,
R8 is 1-4C-alkyl or 3-7C-cycloalkyl,
Y is phenyl, pyrrolyl, furanyl, thienyl, thiazolyl, oxazolyl, thiadiazolyl, oxadiazolyl, pyridinyl, pyrimidinyl, pyrazinyl or pyridazinyl, wherein each of pyrrolyl, furanyl, thienyl, thiazolyl, oxazolyl, thiadiazolyl, oxadiazolyl, pyridinyl, pyrimidinyl, pyrazinyl or pyridazinyl is optimally substituted by R9,
R9 is 1-4C-alkyl, 1-4C-alkoxy or halogen,
or a salt, a tautomer, or a stereoisomer thereof, or a salt of said tautomer or said stereoisomer.

3. The compound according to claim 1, wherein ring B and the pyrimidine to which it is fused form a ring system selected from the group consisting of

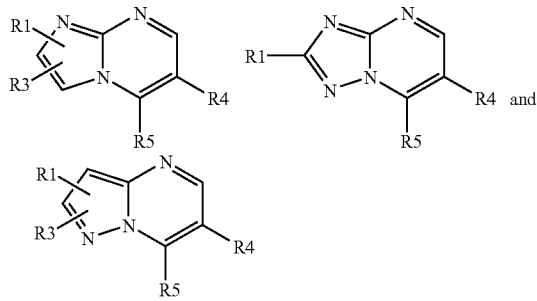

wherein
R1 is hydrogen, 1-4C-alkyl, halogen, amino, 1-4C-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl,
R2 is hydrogen or 1-4C-alkyl,
R3 is hydrogen,
R4 is phenyl or thienyl,
R5 is hydrogen, 1-4C-alkoxy, amino, mono- or di-1-4C-alkylamino, 1-4C-alkyl or 3-7C-cycloalkyl,
R6 is hydrogen or methyl,
R7 is —W—Y,
W is 1,2,4-triazolylene, pyrazolylene or imidazolylene,
Y is phenyl, furan-2-yl, pyrrol-2-yl, thien-2-yl, thiazol-2-yl, thiazol-4-yl, oxazol-2-yl, oxazol-4-yl, 1,3,4-thiadiazol-2-yl, 1,3,4-oxadiazol-2-yl, pyridin-2-yl, pyridin-4-yl, pyrimidin-2-yl, pyrimidin-4-yl, pyrazin-2-yl or pyridazin-3-yl, wherein each of furan-2-yl, pyrrol-2-yl, thien-2-yl, thiazol-2-yl, thiazol-4-yl, oxazol-2-yl, oxazol-4-yl, 1,3,4-thiadiazol-2-yl, 1,3,4-oxadiazol-2-yl, pyridin-2-yl, pyridin-4-yl, pyrimidin-2-yl, pyrimidin-4-yl, pyrazin-2-yl or pyridazin-3-yl is optionally substituted by R9,
R9 is 1-4C-alkyl, 1-4C-alkoxy or halogen,
or a salt, a tautomer, or a stereoisomer thereof, or a salt of said tautomer or said stereoisomer.

4. The compound according to claim 1, wherein ring B and the pyrimidine to which it is fused form a ring system selected from the group consisting of

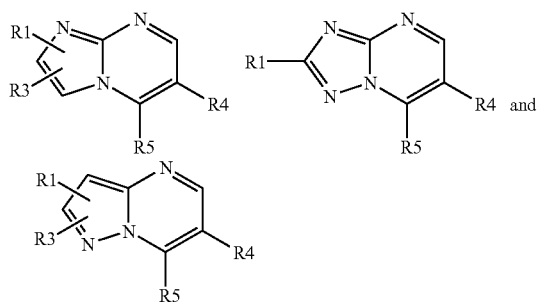

wherein
R1 is hydrogen, 1-4C-alkyl, halogen, amino, 1-4C-alkoxy, cyano, 3-7C-cycloalkyl, 2-4C-alkenyl, 2-4C-alkynyl, mono- or di-1-4C-alkylamino, —C(O)OR2 or trifluoromethyl, R2 is 1-4C-alkyl, R3 is hydrogen, R4 is phenyl or thienyl, R5 is hydrogen, 1-4C-alkoxy, mono- or di-1-4C-alkylamino or 1-4C-alkyl, R6 is hydrogen or methyl, R7 is —W—Y, W is 1,2,4-triazolylene or pyrazolylene, Y is phenyl, furan-2-yl, pyrrol-2-yl, pyridin-4-yl, thiazol-2-yl, pyridin-2-yl, pyrimidin-2-yl, pyrazin-2-yl, pyrimidin-4-yl or pyridazin-3-yl, wherein each of furan-2-yl, pyrrol-2-yl, pyridin-4-yl, thiazol-2-yl, pyridin-2-yl, pyrimidin-2-yl, pyrazin-2-yl, pyrimidin-4-yl or pyridazin-3-yl is optionally substituted by R9, R9 is 1-4C-alkyl, 1-4C-alkoxy or halogen, or a salt, a tautomer, or a stereoisomer thereof, or a salt of said tautomer or said stereoisomer.

5. A compound, which is 6-phenyl-7-(4-{[4-(3-pyridin-2-yl-1,2,4-triazol-5-yl)piperidin-1-yl]methyl}phenyl)imidazo[1,2a]-pyrimidine;

6-phenyl-5-(4-{[4-(5-pyridin-2-yl-1,2,4-triazol-3-yl)piperidin-1-yl]methyl}phenyl)[1,2,4]triazolo[1,5-a]-pyrimidine;

2-methyl-6-phenyl-5-(4-{[4-(5-pyridin-2-yl-1,2,4-triazol-3-yl)piperidin-1-yl]methyl}phenyl)[1,2,4]-triazolo[1,5-a]pyrimidine;

2-cyclopropyl-6-phenyl-5-(4-{[4-(5-pyridin-2-yl-1,2,4-triazol-3-yl)piperidin-1-yl]methyl}phenyl)[1,2,4]-triazolo[1,5-a]pyrimidine;

6-phenyl-7-(4-{[4-(3-pyridin-2-yl-pyrazol-5-yl)piperidin-1-yl]methyl}phenyl)imidazo[1,2-a]pyrimidine;

6-phenyl-7-(4-{[4-(5-pyridin-4-yl-1,2,4-triazol-3-yl)piperidin-1-yl]methyl}phenyl)imidazo[1,2-a]-pyrimidine;

2-cyclobutyl-6-phenyl-5-(4-{[4-(5-pyridin-2-yl-1,2,4-triazol-3-yl)piperidin-1-yl]methyl}phenyl)[1,2,4]-triazolo[1,5-a]pyrimidine;

6-phenyl-7-(4-{[4-(5-pyridin-2-yl-1,2,4-triazol-3-yl)piperidin-1-yl]methyl}phenyl)imidazo[1,2-a]-pyrimidine-3-carbonitrile;

3-fluoro-6-phenyl-7-(4-{[4-(5-pyridin-2-yl-1H-1,2,4-triazol-3-yl)piperidin-1-yl]methyl}phenyl)-imidazo[1,2-a]pyrimidine;

N-methyl-6-phenyl-7-(4-{[4-(5-pyridin-2-yl-1,2,4-triazol-3-yl)piperidin-1-yl]methyl}phenyl)-imidazo[1,2-a]pyrimidin-5-amine;

3-bromo-6-phenyl-7-(4-{[4-(5-pyridin-2-yl-1,2,4-triazol-3-yl)piperidin-1-yl]methyl}phenyl)-imidazo[1,2-a]pyrimidine;

3-chloro-6-phenyl-7-(4-{[4-(5-pyridin-2-yl-1,2,4-triazol-3-yl)piperidin-1-yl]methyl}phenyl)imidazo[1,2-a]pyrimidine;

3-ethynyl-6-phenyl-7-(4-{[4-(5-pyridin-2-yl-1,2,4-triazol-3-yl)piperidin-1-yl]methyl}-phenyl)imidazo[1,2-a]pyrimidine;

3-methyl-6-phenyl-7-(4-{[4-(5-pyridin-2-yl-1,2,4-triazol-3-yl)piperidin-1-yl]methyl}phenyl)imidazo[1,2-a]pyrimidine;

6-phenyl-7-(4-{[4-(5-pyridin-2-yl-1,2,4-triazol-3-yl)piperidin-1-yl]methyl}phenyl)-3-vinylimidazo[1,2-a]pyrimidine;

Ethyl-6-phenyl-7-(4-{[4-(5-pyridin-2-yl-1,2,4-triazol-3-yl)piperidin-1-yl]methyl}phenyl)imidazo[1,2-a]pyrimidine-2-carboxylate;

2-ethyl-6-phenyl-7-(4-{[4-(5-pyridin-2-yl-1,2,4-triazol-3-yl)piperidin-1-yl]methyl}phenyl)imidazo[1,2-a]pyrimidine;

6-phenyl-7-(4-{[4-(5-pyrimidin-2-yl-1,2,4-triazol-3-yl)piperidin-1-yl]methyl}phenyl)imidazo[1,2-a]pyrimidine;

6-phenyl-5-(4-{[4-(5-pyridin-2-yl-1,2,4-triazol-3-yl)piperidin-1-yl]methyl}phenyl)pyrazolo[1,5-a]pyrimidine;

6-phenyl-7-(4-{[4-(4-pyridin-2-yl-imidazol-1-yl)piperidin-1-yl]methyl}phenyl)imidazo[1,2-a]pyrimidine;

6-phenyl-7-(4-{[4-(5-pyrazin-2-yl-1,2,4-triazol-3-yl)piperidin-1-yl]methyl}phenyl)imidazo[1,2-a]pyrimidine;

3-ethyl-6-phenyl-7-(4-{[4-(5-pyridin-2-yl-1,2,4-triazol-3-yl)piperidin-1-yl]methyl}phenyl)imidazo[1,2-a]pyrimidine;

6-phenyl-7-(4-{1-[4-(5-pyridin-2-yl-1H-1,2,4-triazol-3-yl)piperidin-1-yl]ethyl}phenyl)imidazo[1,2-a]pyrimidine;

3-fluoro-6-phenyl-7-(4-{[4-(5-pyrazin-2-yl-1,2,4-triazol-3-yl)piperidin-1-yl]methyl}phenyl)imidazo[1,2-a]pyrimidine;

3-fluoro-6-phenyl-7-(4-{[4-(5-pyrimidin-2-yl-1H-1,2,4-triazol-3-yl)piperidin-1-yl]methyl}phenyl)-imidazo[1,2-a]pyrimidine;

6-phenyl-7-(4-{[4-(5-pyridin-2-yl-1H-1,2,4-triazol-3-yl)piperidin-1-yl]methyl}phenyl)-2-(trifluoromethyl)imidazo[1,2-a]pyrimidine;

5-methyl-6-phenyl-7-(4-{[4-(5-pyridin-2-yl-1H-1,2,4-triazol-3-yl)piperidin-1-yl]methyl}phenyl)-imidazo[1,2-a]pyrimidine;

2-Isopropyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine;

7-Methoxy-6-phenyl-5-(4-{[4-(5-pyridin-2-yl-1H-1,2,4-triazol-3-yl)piperidin-1-yl]methyl}phenyl)pyrazolo[1,5-a]pyrimidine;

3-Chloro-6-phenyl-5-(4-{[4-(5-pyridin-2-yl-1H-1,2,4-triazol-3-yl)piperidin-1-yl]methyl}phenyl)pyrazolo[1,5-a]pyrimidine;

3-Bromo-6-phenyl-5-(4-{[4-(5-pyridin-2-yl-1H-1,2,4-triazol-3-yl)piperidin-1-yl]methyl}phenyl)pyrazolo[1,5-a]pyrimidine;

6-Phenyl-5-(4-{[4-(5-pyridin-2-yl-1H-1,2,4-triazol-3-yl)piperidin-1-yl]methyl}phenyl)pyrazolo[1,5-a]pyrimidine-3-carbonitrile;

3-Ethynyl-6-phenyl-5-(4-{[4-(5-pyridin-2-yl-1H-1,2,4-triazol-3-yl)piperidin-1-yl]methyl}phenyl)pyrazolo[1,5-a]pyrimidine;

3-Ethyl-6-phenyl-5-(4-{[4-(5-pyridin-2-yl-1H-1,2,4-triazol-3-yl)piperidin-1-yl]methyl}phenyl)pyrazolo[1,5-a]pyrimidine;

7-[4-({4-[5-(4-Methylpyridin-2-yl)-1H-1,2,4-triazol-3-yl]piperidin-1-yl}methyl)phenyl]-6-phenylimidazo[1,2-a]pyrimidine;

7-[4-({4-[5-(6-Methylpyridin-2-yl)-1H-1,2,4-triazol-3-yl]piperidin-1-yl}methyl)phenyl]-6-phenylimidazo[1,2-a]pyrimidine;

3-Methyl-6-phenyl-5-(4-{[4-(5-pyridin-2-yl-1H-1,2,4-triazol-3-yl)piperidin-1-yl]methyl}phenyl)pyrazolo[1,5-a]pyrimidine;

2,7-Dimethyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine;

2-Ethyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine;
2-Methyl-6-phenyl-5-[4-({4-[5-(1,3-thiazol-2-yl)-1H-1,2,4-triazol-3-yl]piperidin-1-yl}methyl)phenyl][1,2,4]triazolo[1,5-a]pyrimidine;
2-Methyl-6-phenyl-5-(4-{[4-(5-pyridin-2-yl-1H-1,2,4-triazol-3-yl)piperidin-1-yl]methyl}phenyl)pyrazolo[1,5-a]pyrimidine;
2-Methyl-6-phenyl-5-(4-{[4-(5-pyrimidin-2-yl-1H-1,2,4-triazol-3-yl)piperidin-1-yl]methyl}phenyl)[1,2,4]triazolo[1,5-a]pyrimidine;
2-Methyl-6-phenyl-5-(4-{[4-(3-pyridin-2-yl-1H-pyrazol-5-yl)piperidin-1-yl]methyl}phenyl)[1,2,4]triazolo[1,5-a]pyrimidine;
2-Methyl-6-phenyl-5-(4-{[4-(5-pyridin-4-yl-1H-1,2,4-triazol-3-yl)piperidin-1-yl]methyl}phenyl)[1,2,4]triazolo[1,5-a]pyrimidine;
2-Cyclopropyl-6-phenyl-5-(4-{[4-(5-pyridin-2-yl-1H-1,2,4-triazol-3-yl)piperidin-1-yl]methyl}phenyl)pyrazolo[1,5-a]pyrimidine;
2,7-Dimethyl-6-phenyl-5-(4-{[4-(5-pyridin-2-yl-1H-1,2,4-triazol-3-yl)piperidin-1-yl]methyl}phenyl)pyrazolo[1,5-a]pyrimidine;
5-(4-{[4-(5-Pyridin-2-yl-1H-1,2,4-triazol-3-yl)piperidin-1-yl]methyl}phenyl)-6-(3-thienyl)pyrazolo[1,5-a]pyrimidine;
7-(4-{[4-(5-Pyridin-2-yl-1H-1,2,4-triazol-3-yl)piperidin-1-yl]methyl}phenyl)-6-(3-thienyl)imidazo[1,2-a]pyrimidine;
2-Bromo-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine;
2-Ethynyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine;
2-Methyl-5-(4-{[4-(5-pyridin-2-yl-1H-1,2,4-triazol-3-yl)piperidin-1-yl]methyl}phenyl)-6-(3 thienyl)[1,2,4]triazolo[1,5-a]pyrimidine;
N,N-Dimethyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidin-2-amine;
6-Phenyl-5-(4-{[4-(5-pyridin-2-yl-1H-1,2,4-triazol-3-yl)piperidin-1-yl]methyl}phenyl)-2-(trifluoromethyl)[1,2,4]triazolo[1,5-a]pyrimidine;
N,N,2-Trimethyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidin-7-amine;
N-Methyl-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidin-2-amine;
2-Methoxy-6-phenyl-5-(4-{[4-(5-pyridin-2-yl-1H-1,2,4-triazol-3-yl)piperidin-1-yl]methyl}phenyl)[1,2,4]triazolo[1,5-a]pyrimidine;
6-Phenyl-5-(4-{[4-(5-pyridin-2-yl-1H-1,2,4-triazol-3-yl)piperidin-1-yl]methyl}phenyl)[1,2,4]triazolo[1,5-a]pyrimidin-2-amine;
6-Phenyl-7-[4-({4-[3-(1H-pyrrol-2-yl)-1H-1,2,4-triazol-5-yl]piperidin-1-yl}methyl}phenylimidazo[1,2-a]pyrimidine;
6-Phenyl-5-(4-{[4-(3-pyrimidin-2-yl-1H-1,2,4-triazol-5-yl)piperidin-1-yl]methyl}phenyl)pyrazolo[1,5-a]pyrimidine;
6-Phenyl-5-[4-({4-[3-(1,3-thiazol-2-yl)-1H-1,2,4-triazol-5-yl]piperidin-1-yl}methyl)phenyl]pyrazolo[1,5-a]pyrimidine;
6-Phenyl-5-(4-{[4-(3-pyridin-4-yl-1H-1,2,4-triazol-5-yl)piperidin-1-yl]methyl}phenyl)pyrazolo[1,5-a]pyrimidine;
6-Phenyl-5-[4-({4-[3-(1H-pyrrol-2-yl)-1H-1,2,4-triazol-5-yl]piperidin-1-yl}methyl)phenyl]pyrazolo[1,5-a]pyrimidine;
2-Methyl-6-phenyl-5-[4-({4-[3-(1H-pyrrol-2-yl)-1H-1,2,4-triazol-5-yl]piperidin-1-yl}methyl)phenyl][1,2,4]triazolo[1,5-a]pyrimidine;
2-Methyl-5-({4-[3-(6-methylpyridin-2-yl)-1H-1,2,4-triazol-5 piperidin-1-yl}methyl)phenyl]-6-phenyl[1,2,4]triazolo[1,5-a]pyrimidine;
5-[4-({4-[3-(6-Methylpyridin-2-yl)-1H-1,2,4-triazol-5-yl]piperidin-1-yl}methyl)phenyl]-6-phenylpyrazolo[1,5-a]pyrimidine;
6-Phenyl-5-(4-{[4-(3-pyridin-2-yl-1H-pyrazol-5-yl)piperidin-1-yl]methyl}phenyl)pyrazolo[1,5-a]pyrimidine;
Methyl 6-phenyl-5-(4-{[4-(5-pyridin-2-yl-1H-1,2,4-triazol-3-yl)piperidin-1-yl]methyl}phenyl)pyrazolo[1,5-a]pyrimidine-2-carboxylate;
6-Phenyl-5-(4-{[4-(5-pyridin-2-yl-1H-1,2,4-triazol-3-yl)piperidin-1-yl]methyl}phenyl)pyrazolo[1,5-a]pyrimidine-2-carboxamide;
6-Phenyl-5-(4-{[4-(5-pyridin-2-yl-1H-1,2,4-triazol-3-yl)piperidin-1-yl]methyl}phenyl)pyrazolo[1,5-a]pyrimidine-2-carboxylic acid;
5-[4-({4-[3-(2-furyl)-1H-1,2,4-triazol-5-yl]piperidin-1-yl}methyl)phenyl]-2-methyl-6-phenyl[1,2,4]triazolo[1,5-a]pyrimidine;
5-[4-({4-[3-(2-furyl)-1H-1,2,4-triazol-5-yl]piperidin-1-yl}methyl)phenyl]-6-phenylpyrazolo[1,5-a]pyrimidine;
7-[4-({4-[3-(2-furyl)-1H-1,2,4-triazol-5-yl]piperidin-1-yl}methyl)phenyl]-6-phenylimidazo[1,2-a]pyrimidine;
2-methyl-6-phenyl-5-(4-{[4-(3-phenyl-1H-1,2,4-triazol-5-yl)piperidin-1-yl]methyl}phenyl)[1,2,4]triazolo[1,5-a]pyrimidine;
7-[4-({4-[5-(4-methoxypyridin-2-yl)-1H-1,2,4-triazol-3-yl]piperidin-1-yl}methyl)phenyl]-6-phenylimidazo[1,2-a]pyrimidine; and
6-phenyl-7-{4-[4-(5-pyridin-2-yl-1H-[1,2,4]-triazol-3-yl)-piperidin-1-ylmethyl]-phenyl}-imidazo[1,2-a]pyrimidine;

or a salt, a tautomer, or a stereoisomer thereof, or a salt of said tautomer or said stereoisomer.

6. A compound, a tautomer thereof or a stereoisomer thereof, or a pharmaceutically acceptable salt of said compound, tautomer or stereoisomer according to claim 1 for use in the treatment of diseases.

7. A compound, a tautomer thereof or a stereoisomer thereof, or a pharmaceutically acceptable salt of said compound, tautomer or stereoisomer according to claim 1, or a pharmaceutical composition comprising a compound, a tautomer of said compound or a stereoisomer of said compound, or a pharmaceutically acceptable salt of said compound, tautomer or stereoisomer according to, claim 1, for the treatment of hyperproliferative diseases and/or disorders responsive to induction of apoptosis.

8. A pharmaceutical composition comprising at least one compound, tautomer of said compound or stereoisomer of said compound, or a pharmaceutically acceptable salt of said compound, tautomer or stereoisomer according to claim 1, together with at least one pharmaceutically acceptable auxiliary.

9. A combination comprising one or more first active ingredients selected from the group consisting of compounds, tautomers of said compounds, stereoisomers of said compounds, pharmaceutically acceptable salts of said compounds, tautomers and stereoisomers according to claim 1, and one or more second active ingredients selected from the group consisting of chemotherapeutic anti-cancer agents and target-specific anti-cancer agents.

10. A compound according to claim 1 or a pharmaceutically acceptable salt thereof.

11. A compound according to claim 2 or a pharmaceutically acceptable salt thereof.

12. A compound according to claim 3 or a pharmaceutically acceptable salt thereof.

13. A compound according to claim 4 or a pharmaceutically acceptable salt thereof.

14. A compound according to claim 5 or a pharmaceutically acceptable salt thereof.

15. A pharmaceutical composition comprising at least one compound according to claim 1 or a pharmaceutically acceptable salt of said compound together with at least one pharmaceutically acceptable auxiliary.

16. A combination comprising one or more first active ingredients selected from the group consisting of compounds according to claim 1 and pharmaceutically acceptable salts of said compounds, and one or more second active ingredients selected from the group consisting of chemotherapeutic anti-cancer agents and target-specific anti-cancer agents.

17. A compound according to claim 1, in which Y phenyl.

18. A compound of formula (I)

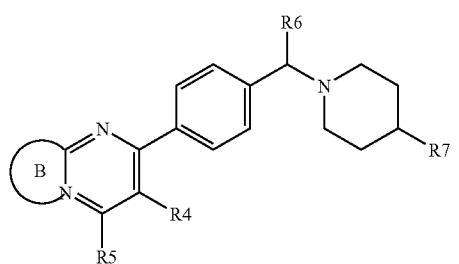

(I)

wherein ring B and the pyrimidine to which it is fused form a ring system selected from the group consisting of

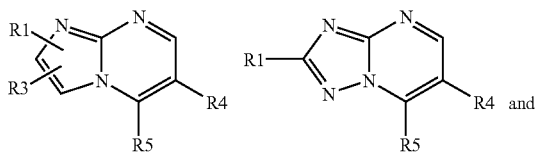

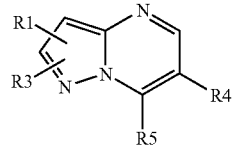

-continued wherein

R1 is hydrogen, 1-4C-alkyl, halogen, amino, 1-4C-alkoxy, cyano, 3-7C-cycloalkyl, 2-4C-alkenyl, 2-4C-alkynyl, 3-7C-cycloalkoxy, mono- or di-1-4C-alkylamino, mono- or di-1-4C-alkylaminocarbonyl, —C(O)NH2, —C(O)OR2 or trifluoromethyl, R2 is hydrogen or 1-4C-alkyl, R3 is hydrogen, 1-4C-alkyl or halogen, R4 is phenyl or thienyl, R5 is hydrogen, 1-4C-alkoxy, amino, mono- or di- 1-4C-alkylamino, 1-4C-alkyl or 3-7C-cycloalkyl, R6 is hydrogen or 1-4C-alkyl, R7 is —W—Y.

W is a monocyclic 5-membered heteroarylene comprising 1 nitrogen atom and optionally 1 or 2 further heteroatoms independently selected from the group consisting of oxygen, nitrogen and sulphur, and wherein the heteroarylene is optionally substituted by R8, R8 is 1-4C-alkyl or 3-7C-cycloalkyl, Y is a monocyclic 5 or 6 membered heteroaryl comprising 1 nitrogen atom and optionally 1 or 2 further heteroatoms independently selected from the group consisting of oxygen, nitrogen, and sulphur, and wherein the heteroaryl is optionally substituted by R9, R9 is 1-4C-alkyl, 1-4C-alkoxy or halogen, or a salt, a tautomer, or a stereoisomer thereof, or a salt of said tautomer or said stereoisomer.

19. A compound according to claim 18 or a pharmaceutically acceptable salt thereof.

20. A pharmaceutical composition comprising at least one compound according to claim 18 or a pharmaceutically acceptable salt of said compound together with at least one pharmaceutically acceptable auxiliary.

* * * * *

UNITED STATES PATENT AND TRADEMARK OFFICE
CERTIFICATE OF CORRECTION

PATENT NO. : 7,776,864 B2  Page 1 of 1
APPLICATION NO. : 12/191703
DATED : August 17, 2010
INVENTOR(S) : Swen Holder It is certified that error appears in the above-identified patent and that said Letters Patent is hereby corrected as shown below:

Column 102, line 63 reads: "R1 is hydrogen, 1-4C-alkyl, halogen, amino, 1-4-G-"
Should read: -- R1 is hydrogen, 1-4C-alkyl, halogen, amino, 1-4-C- --

Column 107, line 60 reads: "5-yl]piperidin-1-yl]methyl}phenylimidazol[1,2-a]pyri-"
Should read: -- 5-yl]piperidin-1-yl]methyl}phenyl]imidazol[1,2-a]pyri- --

Column 108, line 11 reads: "zol-5 piperidin-1-yl}methyl)phenyl]-6-phenyl[1,2,4]"
Should read: -- zol-5-yl]piperidin-1-yl}methyl)phenyl]-6-phenyl[1,2,4] --

Signed and Sealed this

Twelfth Day of October, 2010

David J. Kappos
*Director of the United States Patent and Trademark Office*